US006864365B1

(12) United States Patent
White et al.

(10) Patent No.: US 6,864,365 B1
(45) Date of Patent: Mar. 8, 2005

(54) BACTERIAL FIMBRIAL SYSTEM FOR PRESENTATION OF HETEROLOGOUS PEPTIDE SEQUENCES

(75) Inventors: Aaron P. White, Victoria (CA); James L. Doran, Brentwood Bay (CA); S. Karen Collinson, Brentwood Bay (CA); William W. Kay, Victoria (CA)

(73) Assignee: Innovation and Development Corporation, University of Victoria, Victoria (CA)

( * ) Notice: Subject to any disclaimer, the term of this patent is extended or adjusted under 35 U.S.C. 154(b) by 0 days.

(21) Appl. No.: 09/543,407

(22) Filed: Apr. 5, 2000

Related U.S. Application Data

(60) Provisional application No. 60/127,888, filed on Apr. 5, 1999.

(51) Int. Cl.[7] ........................ C07H 21/04; C07H 21/00; A61K 39/00; A61K 39/12; C12P 21/08

(52) U.S. Cl. .................... 536/23.7; 536/23.1; 536/23.4; 424/184.1; 424/192.1; 424/199.1; 530/587.3

(58) Field of Search .............................. 536/23.1, 23.4, 536/23.7; 424/184.1, 192.1, 199.1, 200.1, 241.1; 435/7.2, 69.3, 69.7, 91.4, 91.41; 530/387.3

(56) References Cited

U.S. PATENT DOCUMENTS 5,635,617 A * 6/1997 Doran et al. ............... 536/23.7

FOREIGN PATENT DOCUMENTS

WO WO 94/25598 * 11/1994

OTHER PUBLICATIONS

Collinson et al, Journal of Bacteriology, Feb. 1996, p. 662–667.*

Hedegaard et al, Gene, 1989, p. 115–124.*

Cardenas et al, Vaccine, vol. 11, Issue 2, 1993.*

Sequence Alignment of SED ID NO:5.*

Abraham et al., "Protection Against *Escherichia coli*–Induced Urinary Tract Infections with Hybridoma Antibodies Directed Against Type 1 Fimbriae or Complementary D–Mannose Receptors," *Infection and Immunity 48*(3): 625–628, Jun. 1985.

Aizawa et al., "Termini of *Salmonella* Flagellin are Disordered and Become Organized upon Polymerization into Flagellar Filament," *J. Mol. Biol. 211*: 673–677, 1990.

Allen–Vercoe et al., "SEF17 fimbriae are essential for the convoluted colonial morphology of *Salmonella enteritidis,*" *FEMS Microbiology Letters 153*: 33–42, 1997.

Austin et al., "Thin aggregative fimbriae enhance *Salmonella enteritidis* biofilm formation," *FEMS Microbiology Letters 162*: 295–301, 1998.

Bakker et al., "K88 fimbriae as carriers of heterologous antigenic determinants," *Microbial Pathogenesis 8*: 343–352, 1990.

Baumann et al., "Three–dimensional structure of the alkaline protease of *Pseudomonas aeruginosa*: a two–domain protein with a calcium binding parallel beta roll motif," *The EMBO Journal 12*(9): 3357–3364, 1993.

Baumann et al., "Crystal Structure of a Complex Between *Serratia marcescens* Metallo–protease and an Inhibitor from *Erwinia chrysanthemi,*" *J. Mol. Biol. 248*: 653–661, 1995.

Baumann, U., "Crystal Structure of the 50 kDa Metallo Protease from *Serratia marcescens,*" *J. Mol. Biol. 242*(3): 244–251, 1994.

Bäumler et al., "Contribution of Horizontal Gene Transfer and Deletion Events to Development of Distinctive Patterns of Fimbrial Operons during Evolution of *Salmonella* Serotypes," *Journal of Bacteriology 179*(2): 317–322, Jan. 1997.

Bäumler and Heffron, "Identification and Sequence Analysis of *lpfABCDE*, a Putative Fimbrial Operon of *Salmonella typhimurium,*" *Journal of Bacteriology 177*(8): 2087–2097, Apr. 1995.

Bernstein et al., "The Protein Data Bank: A Computer–based Archival File for Macromolecular Structures," *J. Mol. Biol. 112*: 535–542, 1977.

Bérubé et al., "Repression of Human Immunodeficiency Virus Type 1 Long Terminal Repeat–Driven Gene Expression by Binding of the Virus to Its Primary Cellular Receptor, the CD4 Molecule," *Journal of Virology 70*(6): 4009–4016, Jun. 1996.

Bian and Normark, "Nucleator function of CsgB for the assembly of adhesive surface organelles in *Escherichia coli,*" *The EMBO Journal 16*(19): 5827–5836, 1997.

Braunagel and Benedik, "The metalloprotease gene of *Serratia marcescens* strain SM6," *Mol. Gen. Genet. 222*: 446–451, 1990.

(List continued on next page.)

*Primary Examiner*—Lynette R. F. Smith
*Assistant Examiner*—Vanessa L. Ford
(74) *Attorney, Agent, or Firm*—Seed IP Law Group PLLC

(57) ABSTRACT

The invention provides a system for creating recombinant agfA fimbrin genes and performing chromosomal gene replacements within *Salmonella*, creating *Salmonella* strains which carry the recombinant agfA genes at the native position in the chromosome. One embodiment of the invention is exemplified by the expression of a model epitope (PT3) obtained from the GP63 protein of *Leishmania major*, by formation of recombinant agfA genes encoding PT3 fusion proteins recombined at 10 different sites throughout the agfA gene. These fusions are shown to be expressed in the thin aggregative fimbriae on the surface of bacterial cell. The agfA fimbrin of *Salmonella* (CsgA for *E. coli*) provides a flexible and stable vehicle for the expression of foreign epitopes in enterobacteriaceae and the subsequent thin aggregative fimbriae (curli) expression product provide an ideal organelle for presentation of the foreign epitopes at the cell surface.

9 Claims, 34 Drawing Sheets

OTHER PUBLICATIONS

Brinton, C.C. Jr., "The Structure, Function, Synthesis and Genetic Control of Bacterial Pili and a Molecular Model for DNA and RNA Transport in Gram Negative Bacteria," *Transactions of the New York Academy of Sciences 27*: 1003–1054, 1965.

Cárdenas and Clements, "Stability, immunogenicity and expresion of foreign antigens in bacterial vaccine vectors," *Vaccine 11*(2): 126–135, 1993.

Cattozzo et al., "Expression and immunogenicity of $V_3$ loop eptiopes of HIV–1, isolates SC and WMJ2, inserted in *Salmonella flagellin*," *Journal of Biotechnology 56*: 191–203, 1997.

Caulcott et al., "Investigation of the Effect of Growth Environment on the Stability of Low–copy–number Plasmids in *Escherichia coli," Journal of General Microbiology 133*: 1881–1889, 1987.

Chatfield et al., "The development of oral vaccines based on live attenuated *Salmonella* strains," *FEMS Immunology and Medical Microbiology 7*: 1–8, 1993.

Chatfield et al., "Evaluation of *Salmonella typhimurium* strains harbouring defined mutations in *htrA* and *aroA* in the murine salmonella model," *Microbial Pathogenesis 12*: 145–151, 1992.

Clouthier et al., "tRNA$^{Arg}$ (*fimU*) and Expression of SEF14 and SEF21 in *Salmonella enteritidis," Journal of Bacteriology 180*(4): 840–845, Feb. 1998.

Clouthier et al., "Characterization of Three Fimbrial Genes, *sefABC*, of *Salmonella enteritidis," Journal of Bacteriology 175*(9): 2523–2533, May 1993.

Clouthier et al., "Periplasmic and fimbrial SefA from *Salmonella enteritidis," Biochimica et Biophysica Acta 1387*: 355–368, 1998.

Cohen et al., "Structural Clues to Prion Replication," *Science 264*: 530–531, Apr. 22, 1994.

Collinson et al., "Purification and Characterization of Thin, Aggregative Fimbriae from *Salmonella enteritidis," Journal of Bacteriology 173*(15): 4773–4781, Aug. 1991.

Collinson et al., "Thin Aggregative Fimbriae from Diarrheagenic *Escherichia coli," Journal of Bacteriology 174*(13): 4490–4495, Jul. 1992.

Collinson et al., "Thin, Aggregative Fimbriae Mediate Binding of *Salmonella enteritidis* to Fibronectin," *Journal of Bacteriology 175*(1): 12–18, Jan. 1993.

Collinson et al., "*Salmonella enteritidis agfBAC* Operon Encoding Thin, Aggregative Fimbriae," *Journal of Bacteriology 178*(3): 662–667, Feb. 1996.

Collinson et al., "Structural Predictions of AgfA, the Insoluble Fimbrial Subunit of *Salmonella* Thin Aggregative Fimbriae," *J. Mol. Biol. 290*: 741–756, 1999.

Collinson et al., "The location of four fimbrin–encoding genes, *agfA, fimA, sefA* and *sefD,* on the *Salmonella enteritidis* and/or *S. typhimurium XbaI–BlnI* genomic restriction maps," *Gene 169*: 75–80, 1996.

Coulson et al., "Effect of different plasmids on colonization of mouse tissues by the aromatic amino acid dependent *Salmonella typhimurium* SL 3261," *Microbial Pathogenesis 16*: 305–311, 1994.

Cowan et al., "Crystallographic Studies on a Family of Cellular Lipophilic Transport Proteins," *J. Mol. Biol. 230*: 1225–1246, 1993.

Curtiss III. et al., "Recombinant *Salmonella* Vectors in Vaccine Development," *Developments in Biological Standardization 82*: 23–33, 1994.

de Graaf and Bakker, *Molecular Recognition in Host–Parasite Interactions,* Korbonen et al. (eds.), Plenum Press, New York, 1992, "Properties and Synthesis of K88 Fimbriae," pp. 39–46.

Der Vartanian et al., "Permissible peptide insertions surrounding the signal peptide–mature protein junction of the ClpG prepilin: CS31A fimbriae of *Escherichia coli* as carriers of foreign sequences," *Gene 148*: 23–32, 1994.

Der Vartanian et al., "An *Escherichia coli* CS31A fibrillum chimera capable of inducing memory antibodies in outbred mice following booster immunization with the enteropathogenic coronavirus transmissible gastroenteritis virus," *Vaccine 15*(2): 111–120, 1997.

Doran et al., "DNA–Based Diagnostic Tests for *Salmonella* Species Targeting *agfA*, the Structural Gene for Thin, Aggregative Fimbriae," *Journal of Clinical Microbiology 31*(9): 2263–2273, Sep. 1993.

Edwards et al., "Improved allelic exchange vectors and their use to analyze 987P fimbria gene expression," *Gene 207*: 149–157, 1998.

Eshdat et al., "Dissociation and Reassembly of *Escherichia coli* Type 1 Pili," *Journal of Bacteriology 148*(1): 308–314, Oct. 1981.

Evans et al., "Hemagglutination of Human Group A Erythrocytes by Enterotoxigenic *Escherichia coli* Isolated from Adults with Diarrhea: Correlation with Colonization Factor," *Infection and Immunity 18*: 330–337, 1977.

Feutrier et al., "Purification and Characterization of Fimbriae from *Salmonella enteritidis," Journal of Bacteriology 168*(1): 221–227, Oct. 1986.

Fields et al., "Mutants of *Salmonella typhimurium* that cannot survive within the macrophage are avirulent," *Proc. Natl. Acad. Sci. USA 83*: 5189–5193, Jul. 1986.

Firth et al., *Escherichia Coli* and *Salmonella*, Neidhardt et al. (eds.), ASM Press, Washington, D.C., 1996, Section C, Chapter 126, "Structure and Function of the F Factor and Mechanism of Conjugation," pp. 2377–2401.

Flynn et al., "Generation of a cytotoxic T–lymphocyte response using a *Salmonella* antigen–delivery system," *Molecular Microbiology 4*(12): 2111–2118, 1990.

Fullner et al., "Pilus Assembly by *Agrobacterium* T–DNA Transfer Genes," *Science 273*: 1107–1109, Aug. 23, 1996.

Gaastra and De Graaf, "Host–Specific Fimbrial Adhesins of Noninvasive Enterotoxigenic *Escherichia coli* Strains," *Microbiological Reviews 46*(2): 129–161, Jun. 1982.

Galán, J.E., "Molecular genetic bases of *Salmonella* entry into host cells," *Molecular Microbiology 20*(2): 263–271, 1996.

Girardeau et al., "Sequence Analysis of the *clpG* Gene, Which Codes for Surface Antigen CS31A Subunit: Evidence of an Evolutionary Relationship between CS31A, K88, and F41 Subunit Genes," *Journal of Bacteriology 173*(23): 7363–7683, Dec. 1991.

Girardeau and Bertin, "Pilins of fimbrial adhesins of different member species of *Enterobacteriaceae* are structurally similar to the C–terminal half of adhesin proteins," *FEBS Letters 357*: 103–108, 1995.

Gong and Makowski; "Helical Structure of P Pili from *Escherichia coli," J. Mol. Biol. 228*: 735–742, 1992.

Griffiths et al., "Cell adhesion molecules in bladder cancer: soluble serum E–cadherin correlates with predictors of recurrence," *British Journal of Cancer 74*: 579–584, 1996.

Ha et al., "Use of the green fluorescent protein as a marker in transfected *Leishmania," Molecular and Biochemical Parasitology 77*: 57–64, 1996.
Hackett, J., "Use of *Salmonella* for heterologous gene expression and vaccine delivery systems," *Current Opinion in Biotechnology 4*: 611–615, 1993.
Hamilton et al., "New Method for Generating Deletions and Gene Replacements in *Escherichia coli," Journal of Bacteriology 171*(9): 4617–4622, Sep. 1989.
Hammar et al., "Nucleator–dependent intercellular assembly of adhesive curli organelles in *Escherichia coli," Proc. Natl. Acad. Sci. USA 93*: 6562–6566, Jun. 1996.
Hammar et al., "Expression of two *csg* operons is required for production of fibronectin– and Congo red–binding curli polymers in *Escherichia coli K–12," Molecular Microbiology 18*(4): 651–670, 1995.
Hashimoto–Gotoh et al., "Specific–purpose plasmid cloning vectors I. Low copy number, temperature–sensitive, mobilization–defective pSC101–derived containment vectors," *Gene 16*: 227–235, 1981.
Heck et al., "Three–Dimensional Structure of *Bordetella pertussis* Fimbriae," *Journal of Structural Biology 116*: 264–269, 1996.
Hedegaard and Klemm, "Type 1 fimbriae of *Escherichia coli* as carriers of heterologous antigenic sequences," *Gene 85*(1): 115–124, Dec. 21, 1989.
Ho et al., The Pili of *Aeromonas hydrophila*: Identification of an Environmentally Regulated "Mini Pilin," *J. Exp. Med. 172*: 795–806, Sep. 1990.
Hobohm and Sander, "A Sequence Property Approach to Searching Protein Databases," *J. Mol. Biol. 251*: 390–399, 1995.
Hone et al., "A chromosomal integration system for stabilization of heterologous genes in Salmonella based vaccine strains," *Microbial Pathogenesis 5*: 407–418, 1988.
Horton et al., "Engineering hybrid genes without the use of restriction enzymes: gene splicing by overlap extension," *Gene 77*: 61–68, 1989.
Hultgren et al., *Escherichia coli* and *Salmonella, Cellular and Molecular Biology,* Neidhardt et al. (eds.), ASM Press, Washington, D.C., 1996, Chapter 150, "Bacterial Adhesins and Their Assembly," pp. 2730–2756.
Hultgren et al., "Pilus: and Nonpilus Bacterial Adhesins: Assembly and Function in Cell Recognition," *Cell 73*: 887–901, Jun. 4, 1993.
Hung et al., "Molecular basis of two subfamilies of immunoglobulin–like chaperones," *The EMBO Journal 15*(15): 3792–3805, 1996.
Ingmer and Cohen, "The pSC101 *par* Locus Alters Protein–DNA Interactions In Vivo at the Plasmid Replication Origin," *Journal of Bacteriology 175*(18): 6046–6048, Sep. 1993.
Jäger et al., "Expression of the *Bacillus subtilis sacB* Gene Leads to Sucrose Sensitivity in the Gram–Positive Bacterium *Corynebacterium glutamicum* but Not in *Streptomyces lividans," Journal of Bacteriology 174*(16): 5462–5465, Aug. 1992.
Jardim et al.,. "Immunoprotective *Leishmania major* Synthetic T Cell Epitopes," *J. Exp. Med. 172*: 645–648, Aug. 1990.
Jennings et al., "Fimbriae of *Bacteroides nodosus*: protein engineering of the structural subunit for the production of an exogenous peptide," *Protein Engineering 2*(5): 365–369, 1989.
Jones et al., "The three–dimensional structure of P2 myelin protein," *The EMBO Journal 7*(6): 1597–1604, 1988.
Jones et al., "The chaperone–assisted membrane release and folding pathway is sensed by two signal transduction systems," *The EMBO Journal 16*(21): 6394–6406, 1997.
Kaniga et al., "A wide–host–range suicide vector for improving reverse genetics in Gram–negative bacteria: inactivation of the *blaA* gene of *Yersinia enterocolitica," Gene 109*: 137–141, 1991.
Kisker et al., "A left–handed β–helix revealed by the crystal structure of a carbonic anhydrase from the archaeon *Methanosarcina thermophila," The EMBO Journal 15*(10): 2323–2330, 1996.
Klemm, P., "The *fimA* gene encoding the type–1 fimbrial subunit of *Escherichia coli," Eur. J. Biochem. 143*: 395–399, 1984.
Klemm and Krogfelt, *Fimbriae: Adhesion, Genetics, Biogenesis, and Vaccines,* Klemm (ed.), CRC Press, Boca Raton, 1994, Chapter 1, "Type 1 Fimbriae of *Escherichia coli*," pp. 9–26.
Kobe and Diesenhofer, "Crystal structure of porcine ribonuclease inhibitor, a protein with leucine–rich repeats," *Nature 366*: 751–756, Dec. 1993.
Korhonen et al., "New Method for Isolation of Immunologically Pure Pili from *Escherichia coli," Infection and Immunity 27*(2): 569–575, Feb. 1980.
Kuehn et al., *Fimbriae: Adhesion, Genetics, Biogenesis, and Vaccines*, Klemm (ed.), CRC Press, Boca Raton, 1994, Chapter 3, "Structure, Function, and Biogenesis of *Escherichia coli* P Pili," pp. 37–51.
Kuehn et al., "P pili in uropathogenic *E. coli* are composite fibres with distinct fibrillar adhesive tips," *Nature 356*:252–255, Mar. 19, 1992.
Lai and Kado, "Processed VirB2 Is the Major Subunit of Promiscuous Pilus of *Agrobacterium tumefaciens," Journal of Bacteriology 180*(10): 2711–2717, May 1998.
Leathart and Gally, "Regulation of type 1 fimbrial expression in uropathogenic *Escherichia coli*: heterogeneity of expression through sequence changes in the *fim* switch region," *Molecular Microbiology 28*(2): 371–381, 1998.
Levi and Arnon, "Synthetic recombinant influenza vaccine induces efficient long–term immunity and cross–strain protection," *Vaccine 14*(1): 85–92, 1996.
Levine et al., *Fimbriae: Adhesion, Genetics, Biogenesis, and Vaccines,* Klemm (ed.), CRC Press, Boca Raton, 1994, Chapter 18, "Fimbrial Vaccines," pp. 255–270.
Levine et al., "Attenuated *Salmonella* as live oral vaccines against typhoid fever and as live vectors," *Journal of Biotechnology 44*: 193–196, 1996.
Lietzke et al., "The Three–Dimensional Structure of Pectate Lyase E, a Plant Virulence Factor from *Erwinia chrysanthemi," Plant Physiology 106*: 849–862, 1994.
Link et al., "Methods for Generating Precise Deletions and Insertions in the Genome of Wild–Type *Escherichia coli*: Application to Open Reading Frame Characterization," *Journal of Bacteriology 179*(20): 6228–6237, Oct. 1997.
Lintermans et al., "Isolation and Nucleotide Sequence of the F17–A Gene Encoding the Structural Protein of the F17 Fimbriae in Bovine Enterotoxigenic *Escherichia coli," Infection and Immunity 56*(6): 1475–1484, Jun. 1988.
Locksley et al., "Susceptibility to Infectious Diseases: *Leishmania* as a Paradigm," *The Journal of Infectious Diseases 179*(suppl. 2): S305–S308, 1999.

Loferer et al., "Availability of the fibre subunit CsgA and the nucleator protein CsgB during assembly of fibronectin–binding *curli* is limited by the intracellular concentration of the novel lipoprotein CsgG," *Molecular Microbiology 26*(1): 11–23, 1997.

Loric et al., "Enhanced Detection of Hematogenous Circulating Prostatic Cells in Patients with Prostate Adenocarcinoma by Using Nested Reverse Transcription Polymerase Chain Reaction Assay Based on Prostate–Specific Membrane Antigen," *Clin. Chem. 41*(12): 1698–1704, 1995.

Low et al., *Escherichia coli and Salmonella, Cellular and Molecular Biology*, 2nd Edition, Neidhardt et al. (eds.), ASM Press, Washington, D.C., 1996, Chapter 11, "Fimbriae," pp. 146–157.

Manen et al., "The *par* region of pSC101 affects plasmid copy number as well as stability," *Molecular Microbiology 4*(11): 1839–1846, 1990.

Marceau et al., "High adhesiveness of encapsulated *Neisseria meningitidis* to epithelial cells is associated with the formation of bundles of pili," *Molecular Microbiology 175*(5): 855–863 1995.

Marceau et al., "Consequences of the loss of O–linked glycosylation of meningococcal type IV pilin on piliation and pilus–mediated adhesion," *Molecular Microbiology 27*(4): 705–715, 1998.

McSorley et al., "Vaccine Efficacy of *Salmonella* Strains Expressing Glycoprotein 63 with Different Promoters," *Infection and Immunity 65*(1): 171–178, Jan. 1997.

Meacock and Cohen, "Partitioning of Bacterial Plasmids during Cell Division: a Cis–Acting Locus That Accomplishes Stable Plasmid Inheritance," *Cell 20*: 529–542, Jun. 1980.

Méchin et al., "Hydrophobic cluster analysis and secondary structure predictions revealed that major and minor structural subunits of K88–related adhesins of *Escherichia coli* share a common overall fold and differ structurally from other fimbrial subunits," *FEBS Letters 364*: 319–324, 1995.

Miller et al., "Role of DNA Superhelicity in Partitioning of the pSC101 Plasmid," *Cell 62*: 127–133, Jul. 13, 1990.

Mol and Oudega, "Molecular and structural aspects of fimbriae biosynthesis and assembly in *Escherichia coli,*" *FEMS Microbiology Reviews 19*: 25–52, 1996.

Morris et al., "Stereochemical Quality of Protein Structure Coordinates," *Proteins: Structure, Function, and Genetics 12*: 345–364, 1992.

Müller et al., "Fimbriation Genes of *Salmonella enteritidis,*" *Journal of Bacteriology 171*(9): 4648–4654, Sep. 1989.

Murzin et al., "SCOP: A Structural Classification of Proteins Database for the Investigation of Sequences and Structures," *J. Mol. Biol. 247*: 536–540, 1995.

Newton et al., "Expression and immunogenicity of an 18–residue epitope of HIV1 gp41 inserted in the flagellar protein of a *Salmonella* live vaccine," *Res. Microbiol. 146*: 203–216, 1995.

Newton et al., "Immune Response to Cholera Toxin Epitope Inserted in *Salmonella* Flagellin," *Science 244*: 70–72, Apr. 7, 1989.

Newton et al., "Expression and Immunogenicity of a Streptococcal M Protein Epitope Inserted in *Salmonella* Flagellin," *Infection and Immunity 59*(6): 2158–2165, Jun. 1991.

Ogawa et al., "Antagonistic effect of synthetic peptides corresponding to the binding regions within fimbrial subunit protein from *Porphyromonas gingivalis* to human gingival fibroblasts," *Vaccine 15*(2): 230–236, 1997.

Olivier et al., "Modulation of Interferon–γ–induced Macrophage Activation by Phosphotryosine Phosphatases Inhibition," *The Journal of Biological Chemistry* 273(22): 13944–13949, May 29, 1998.

Olsén et al., "The RpoS sigma factor relieves H–NS–mediated transcriptional repression of *csgA*, the subunit gene of fibronectin–binding curli in *Escherichia coli,*" *Molecular Microbiology 7*(4): 523–536, 1993.

Pallesen and Klemm, *Fimbriae: Adhesion, Genetics, Biogenesis, and Vaccines*, Klemm (ed.), CRC Press, Boca Raton, 1994, Chapter 19, "Chimeric Fimbrial Vaccines," pp. 271–276.

Paranchych, W., *The Bacteria XI*, Academic Press, Inc., 1990, Chapter 4, "Molecular Studies on *N*–Methylphenylalanine Pili," pp. 61–78.

Paranchych and Frost, "The Physiology and Biochemistry of Pili," *Advances in Microbial Physiology 29*: 53–114, 1988.

Parker and Hodges, "Prediction of Surface and Interior Regions in Proteins—Part II: Predicting Secondary Structure in Regions Bound by Surface Exposed Regions," *Peptide Research 4*(6): 355–363, 1991.

Parker and Hodges, "Prediction of Surface and Interior Regions in Proteins—Part I: Linear Tripeptide Sequences Identify Structural Boundaries in Proteins," *Peptide Research 4*(6): 347–354, 1991.

Pickersgill et al., "The structure of *Bacillus subtilis* pectate lysase in complex with calcium," *Structural Biology 1*(10): 717–723, Oct. 1994.

Römling et al., "Curli Fibers Are Highly Conserved between *Salmonella typhimurium* and *Escherichia coli* with Respect to Operon Structure and Regulation," *Journal of Bacteriology 180*(3): 722–731, Feb. 1998.

Römling et al., "Multicellular and aggregative behaviour of *Salmonella typhimurium* strains is controlled by mutations in the *agfD* promoter," *Molecular Microbiology 28*(2): 249–264, 1998.

Salmond, G.P.C., "Pili, peptidases and protein secretion: curious connections," *Trends in Microbiology 4*(12): 474–476, Dec. 1996.

Shimizu and Morikawa, "The β–prism: a new folding motif," *TIBS 21*: 3–6, Jan. 1996.

Shimizu et al., "Crystal structure of vitelline membrane outer layer protein I (VMO–I): a folding motif with homologous Greek key structures related by an internal three–fold symmetry," *The EMBO Journal 13*(5): 1003–1010, 1994.

Silverman, P.M., "Towards a structural biology of bacterial conjugation," *Molecular Microbiology 23*(3): 423–429, 1997.

Simons et al., "Morphological appearances of K88ab fimbriae and optical diffraction analysis of K88 paracrystalline structures," *FEMS Microbiology Letters 118*: 83–88, 1994.

Simons et al., "The penultimate tyrosine residue of the K99 fibrillar subunit is essential for stability of the protein and its interaction with the periplasmic carrier protein," *FEMS Microbiology Letters 67*: 107–112, 1990.

Sjöbring et al., "Plasminogen, absorbed by *Escherichia coli* expressing curli or by *Salmonella enteritidis* thin aggregative fimbriae, can be activated by simultaneously captured tissue–type plasminogen activator (t–PA)," *Molecular Microbiology 14*(3): 443–452, 1994.

Smyth et al., "Fimbrial adhesins: similaities and variations in structure and biogenesis," *FEMS Immunology and Medical Microbiology 16*: 127–139, 1996.

Spitzer et al., "Long–term protection of mice against *Leishmania major* with a synthetic peptide vaccine," *Vaccine 17*: 1298–1300, 1999.

Steinbacher et al., "Crystal Structure: of P22 Tailspike Protein: Interdigitated Subunits in a Thermostable Trimer," *Science 265*: 383–386, Jul. 15, 1994.

Stentebjerg–Olesen, "Authentic display of a cholera toxin epitope by chimeric type 1 fimbriae: effects of insert position and host background," *Microbiology 143*: 2027–2038, 1997.

St. Geme III et al., "*Haemophilus influenzae* pili are composite structures assembled via the HifB chaperone," *Proc. Natl. Acad. Sci. USA 93*: 11913–11918, Oct. 1996.

Strom and Lory, "Structure–Function and Biogenesis of the Type IV Pili," *Annu. Rev. Microbiol. 47*: 565–596, 1993.

Strugnell et al., "Stable expression of foreign antigens from the chromosome of *Salmonella typhimurium* vaccines strains," *Gene 88*: 57–63, 1990.

Sukupolvi et al., "Expression of Thin Aggregative Fimbriae Promotes Interaction of *Salmonella typhimurium* SR–11 with Mouse Small Intestinal Epithelial Cells," *Infection and Immunity 65*(12): 5320–5325, Dec. 1997.

Sukupolvi et al., "Development of a Murine Model of Chronic *Salmonella* Infection," *Infection and Immunity 65*(2): 838–842, Feb. 1997.

Tennent and Mattick, *Fimbriae: Adhesion, Genetics, Biogenesis, and Vaccines,* Klemm (ed.), CRC Press, Boca Raton, 1994, Chapter 9, "Type 4 Fimbriae," pp. 127–146.

Thanassi et al., "The PapC usher forms an oligomeric channel: Implications for pilus biogenesis across the outer membrane," *Proc. Natl. Acad. Sci. USA 95*: 3146–3151, Mar. 1998.

Thiry et al., "Cloning of DNA Sequences Encoding Foreign Peptides and Their Expression in the K88 Pili," *Applied and Environmental Microbiology 55*(4): 984–993, Apr. 1989.

Thorns et al., "The use of latex particle agglutination to specifically detect *Salmonella enteritidis,*" *International Journal of Food Microbiology 21*: 47–53, 1994.

Titus et al., "A limiting dilution assay for quantifying *Leishmania major* in tissues of infected mice," *Parasite Immunology 7*: 545–555, 1985.

van Der Zee et al., "P–fimbriae of *Escherichia coli* as carriers for gonadotropin releasing hormone: development of a recombinant contraceptive vaccine," *Vaccine 13*(8): 753–758, 1995.

van Die et al., "Expression of foreign epitopes in P–fimbriae of *Escherichia coli,*" *Mol. Gen. Genet. 222*: 297–303, 1990.

Vanegas et al., "In a vaccine model, selected substitution of a highly stimulatory T cell epitope of hen's egg lysozyme into a *Salmonella* flagellin does not result in a homologous, specific, cellular immune response and may alter the way in which the total antigen is processed," *Vaccine 15*(3): 321–324, 1997.

Verma et al., "Induction of a cellular immune response to a defined T–cell epitope as an insert in the flagellin of a live vaccine strain of *Salmonella,*" *Vaccine 13*(3): 235–244, 1995.

Verma et al., "Delivery of class I and class II MHC–restricted T–cell epitopes of listeriolysin of *Listeria moncytogenes* by attenuated *Salmonella,*" *Vaccine 13*(2): 142–150, 1995.

Vidal et al., "Isolation of an *Escherichia coli* K–12 Mutant Strain Able To Form Biofilms on Inert Surfaces: Involvement of a New *ompR* Allele That Increases Curli Expression," *Journal of Bacteriology 180*(9): 2442–2449, May 1998.

Wahle and Kornberg, "The partition locus of plasmid pSC101 is a specific binding site for DNA gyrase," *The EMBO Journal 7*(6): 1889–1895, Jun. 1988.

White et al., "High efficiency gene replacement in *Salmonella enteritidis:* chimeric fimbrins containing a T–cell epitope from *Leishmania major,*" *Vaccine 17*: 2150–2161, 1999.

Whittaker et al., "Mechanisms of Adhesion by Oral Bacteria," *Annu. Rev. Microbiol. 50*: 513–552, 1996.

Wishart et al., "SEQSEE: a comprehensive program suite for protein sequence analysis," *Comput. Appl. Biosci. 10*(2): 121–132, 1994.

Wu et al., "Expression of immunogenic epitopes of hepatitis B surface antigen with hybrid flagellin proteins by a vaccine strain of *Salmonella,*" *Proc. Natl. Acad. Sci. USA 86*: 4726–4730, Jun. 1989.

Xu et al., "Protection against *Leishmania major* infection in genetically susceptible BALB/c mice by GP63 delivered orally in attenuated *Salmonella typhimurium* ($AroA^-$ $AroD^-$)," *Immunology 85*: 1–7, 1995.

Yoder and Jurnak, "The parallel β helix and other coiled folds," *FASEB J. 9*(5): 335–342, Mar. 1995.

* cited by examiner

Parallel β-helix model of AgfA 1 3 5 7 9 12 14 16 18

| | S x I Φ I x Q | N x I Φ I x Q |
|---|---|---|
| C5a | L S I | A L A |
| C5b | T T I | A D V |
| C5c | I E L | A T I |
| C5d | I T V | A L V |
| C5e | V M V | A T A |

*Fig. 9E*

```
  1  G V V P Q W G G G G N H N G G G N S S G P D
aix  c c c c c c c c c c c c c c c c c c c c c c
hie  c c e c c c c c c c c c c c c c c c c c c c
gar  e e e e e e c t c c c c c t t t c c c c c t
gib  e e e e e e c c c c e e c c c c c c c c c c
nnp          e

 23  S T[L S I]Y Q   Y G S A   N A[A L A]L Q   S D A R K
aix  c e e e e e e   c c c c   h h h h h h h   h h c c c
hie  c c e e e e e   c c c c   h h h h h h h   h c c c c
gar  e e e e e e e   e c c c   h h h h h h h   h h h h h
gib  e e e e e e e   e c h h   h h h h h h h   h h h h c
nnp    e e e e e e   e         h h h h h h h   h

 46  S E[T T I]T Q   S G Y G   N G[A D V]G Q     G A D N
aix  c c e e e e c   c c c c   c c c c c c c     c c c c
hie  c c e e e e e   c c c c   c c c c c c c     c c c c
gar  c e e e e e e   e t t c   c e e e e e e     c c c c
gib  c e e e e e e   e e c c   c c e e e e e     c c c c
nnp      e e e e e

 68  S T[I E L]T Q   N G F R   N N[A T I]D Q   W N A K N
aix  c e e e e e c   c c c c   c c h h h h h   h h c c c
hie  c e e e e c c   c c c c   c c c c e e h   c c c c c
gar  e e e e e e e   t t t c   c c e e e e e   e c c c t
gib  c e e e e e e   h c c e   c c h h h h h   h h h c c
nnp      e e h h

 91  S D[I T V]G Q   Y G G N   N A[A L V]N Q     T A S D
aix  c c e e e e c   c c c c   c h h h h h h     c c c c
hie  c c e e e e e   c c c c   c e e e e e c     c c c c
gar  c e e e e e e   t c c c   c e e e e e e     e c c t
gib  c c e e e e e   e c c c   c h e e e e e     c c c c
nnp      e e e e
                                   h h h h

113  S S[V M V]R Q   V G F G   N N[A T A]N Q   Y
aix  c c e e e e e   e e c c   c c c c c c c   c
hie  c e e e e e e   e e c c   c c c c c c c   c
gar  e e e e e e e   e e c c   c c c c c e e   e
gib  c c e e e e e   e e e c   c c c c h c h   e
nnp      e e e e e
```

*Fig. 10*

| | | | | | | | | | | | | | | | | | | | | | | | |
|---|---|---|---|---|---|---|---|---|---|---|---|---|---|---|---|---|---|---|---|---|---|---|---|
| | ● | ○ | ● | ○ | ● | ○ | ● | t | t | t | t | ● | ○ | ● | ○ | ● | ○ | ● | t | t | t | t | t |
| | | | i | φ | i | | | | | | | | | i | φ | i | | | | | | | |
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
| | S | T | L | S | I | Y | Q | Y | G | S | A | N | A | A | L | A | L | Q | S | D | A | R | K |
| AgfA | S | E | T | T | I | T | Q | S | G | Y | G | N | G | A | D | V | G | Q | - | G | A | D | N |
| | S | T | I | E | L | T | Q | N | G | F | R | N | N | A | T | I | D | Q | W | N | A | K | N |
| | S | D | I | T | V | G | Q | Y | G | G | N | N | A | A | L | V | N | Q | - | T | A | S | D |
| | S | S | V | M | V | R | Q | V | G | F | G | N | N | A | T | A | N | Q | Y | | | | |
| | S | E | L | N | I | Y | Q | Y | G | G | G | N | S | A | L | A | L | Q | T | D | A | R | N |
| CsgA | S | D | L | T | I | T | Q | H | G | G | G | N | G | A | D | V | G | Q | - | G | S | D | D |
| | S | S | I | D | L | T | Q | R | G | F | G | N | S | A | T | L | D | Q | W | N | G | K | N |
| | S | E | M | T | V | K | Q | F | G | G | G | N | G | A | A | V | D | Q | - | T | A | S | N |
| | S | S | V | N | V | T | Q | V | G | F | G | N | N | A | T | A | H | Q | Y | | | | |

*Fig. 15*

```
SMP   328  I E N A I G G S G - N D - V I V G N A A N N   347
      348      V L K G G A G - N D - V L F G G G G A D     365
      366      E L W G G A G - K D   I F V F S A A S D     383

AgfA   23  S T L S I Y Q Y G S A N A A L A L Q S D A R K   45
       46  S E T T I T Q S G Y G N G A D V G Q G A D N     67
       68  S T I E L T Q N G F R N N A T I D Q W N A K N   90
```

*Fig. 16A*

```
PMP   40  V I I S K K G D I I T I R T - E S P F K N T E       61
      62  I S F K L G Q E F E E T T A D N R K T K S T V T L   86

AgfA  25  L S I Y Q Y G S A N A A L A L Q S D A R K S E       47
      48  T T I T Q S G Y G N G A D V G Q G A D N S T I E L   72
```

*Fig. 16B*

```
VMO-I  34  F A L K V E P S Q F G R D D T A L N G    52
       37  F S L R S E K S Q G G G D D T A A N N   105
      138  L Q T K V E S P Q G L R D D T A L N N   156

       25  L S I - Y Q - - Y G S A N A A L A L Q    40
       70  I E L - T Q - - N G F R N N A T I D Q    85
      115  V M V - R Q - - V G F G N N A T A N Q   130
```

PT3 epitope of *L. major*

YDQLVTRVVTHEMAHA

SefA amino acid sequence

BACTERIAL FIMBRIAL SYSTEM FOR PRESENTATION OF HETEROLOGOUS PEPTIDE SEQUENCES

CROSS-REFERENCE TO RELATED APPLICATION

This application claims priority to U.S. Provisional Application No. 60/127,888, filed Apr. 5, 1999, which application is incorporated by reference in its entirety.

TECHNICAL FIELD OF THE INVENTION

The invention relates to the use of thin aggregative fimbriae (TAF; SEF17) from *Salmonella* or its homologue, curli from *Escherichia coli*, to express one or more peptide sequences derived from heterologous, pathogenic organisms (bacteria, viruses, protozoa).

BACKGROUND OF THE INVENTION

Creation of Recombinant *Salmonella* Strains

Several methods for generating *Salmonella* vaccine strains expressing chromosomally integrated foreign DNA have been developed. Three such methods are: 1) specific integration into the aroC gene [Strugnell, 1990], 2) using of a defective transposable element [Flynn, 1990], and 3) specific integration into the his locus [Hone, 1988].

However, use of any of these methods results in chromosomal insertion of the recombinant genes into regions where the wild-type (original) genes are not normally found. Because of this, the native promoter region(s) cannot be utilized for expression. Therefore, the development of strategies for heterologous antigen presentation which address the use of native promoter regions and minimize genetic alterations in the host chromosome are required.

SUMMARY OF THE INVENTION

A high frequency chromosomal gene replacement method of general utility was developed for *Salmonella enteritidis*. This system uses an unstable, imperfectly segregating, temperature-sensitive replicon, pHSG415, as a carrier of the recombinant gene of interest and allows for site-specific replacement of chromosomal genes without the need for antibiotic resistance markers in the recombinant genes or the use of specific bacterial strains. This strategy was used to replace the chromosomal agfA fimbrin genes of *S. enteritidis* 3b with recombinant genes containing a 48 bp DNA fragment encoding PT3, an immunoprotective T cell epitope from GP63 of *Leishmania major*. This represents the first report of fimbrial epitope replacement in the *Salmonellae* and the first chimeric fimbrin genes that have been reconstituted into a wild-type genetic background for any organism.

Thin aggregative fimbriae (TAF) of *S. enteritidis* were modified to effectively present heterologous epitopes. Sixteen amino acid segments were replaced by PT3 at 10 different sites throughout agfA, the major fimbrial subunit protein, chosen on the basis of primary protein sequence alignment, secondary structure predictions and comparison to a 3-D model of agfA structure. All 10 segment replacements resulted in chimeric fimbrin proteins expressed by *S. enteritidis* from the native chromosomal promoter, each representing a replacement of over 10% of the total AgfA protein. Immunogold electron microscopy indicated that 8 of the 10 chimeric fimbrins were effectively assembled into fimbrial fibers expressed at the cell surface of *S. enteritidis*. These results demonstrate that AgfA and thin aggregative fimbriae represents a unique, flexible and fascile system for carrying heterologous peptide sequences.

CsgA and curli, the *E. coli* homologues to AgfA and thin aggregative fimbriae, respectively, as well as the proposed minor subunit proteins, AgfB for TAF and CsgB for curli, which are homologues of AgfA and CsgA, are likely to be equally valid carriers for heterologous sequences.

BRIEF DESCRIPTION OF THE DRAWINGS

FIG. 10. Secondary structure predictions of AgfA (SEQ ID NO: 31) in which extended (e), helix (h), coil (c) or turn (t) propensity are noted under each amino acid letter designation. The programs Alexsis (alx), Hierarchial Neural Network (hie), Garnier (gar), Gibrat (gib) and NNPredict (nnp) were used to analyze AgfA as described in the Materials and Methods.

FIG. 15. Alignment of the five *S. enteritidis* AgfA (SEQ ID NO: 34) C-terminal tandem repeat sequences with those of *E. coli* CsgA (SEQ ID NO: 35) such that the amino acid residue positions are numbered according to FIG. 9*d* and FIG. 11*c*. Symbols above the numbered amino acids indicate the positions of proposed internalized (.), surface exposed (o), turn (t) residues or the two nonpolar-polar-nonpolar triplets (ifi) within the parallel β helix model of AgfA. Surface or turn residues are colour coded: polar or acidic (red), basic (blue), nonpolar (green), W (yellow) and G (black). Proposed internalized residues are noted in black.

FIG. 16. Alignments of AgfA with β structural motifs of the three template proteins of known structure used to assemble AgfA models. AgfA sequence was aligned with the (a) β roll motif sequence of *Serratia marcescens* protease (SMP) (SEQ ID NO: 36) (Baumann, 1994; Braunagel & Benedik, 1990), AgfA (SEQ ID NO: 37) (b) β barrel motif of bovine myelin P2 protein (PMP) (SEQ ID NO: 38) (Jones et al., 1988), AgfA (SEQ ID NO: 39), (c) β prism motif of the vitelline membrane outer layer protein I (VMO-I) (SEQ ID Nos: 40–45) (Shimizu & Morikawa, 1996). Bold characters indicate nonpolar-polar-nonpolar motifs, gaps (–) were introduced for optimal alignments. Residues are numbered according to published sequences.

SEQUENCE LISTING

Figure 1A:
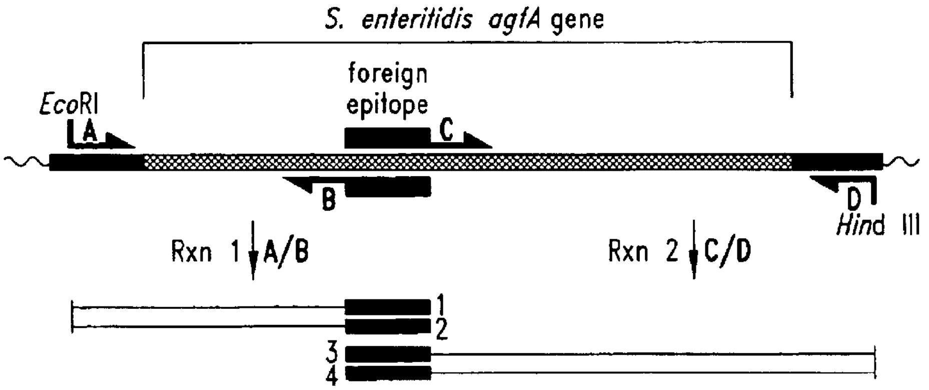
FIG. 1. Schematic of the two step overlap extension or crossover PCR protocol used to generate recombinant *S. enteritidis* agfA. (A) Step one of the protocol involved a vector-borne (wavy lines) target *S. enteritidis* gene (grey box) that was PCR amplified in two fragments using two pairs of primers, (A/B, C/D, arrows). Internal primers encoded the foreign epitope (solid black line) whereas external primers encoded restriction endonuclease recognition sites (EcoRI or HindIII) for subsequent cloning. (B) In step two, both purified PCR products were combined with external primers as described in Experimental procedures and PCR was used to generate gene fragments (1 and 4) which annealed to generate the whole chimeric gene. (C) Recombinant *S. enteritidis* agfA containing 48 bp foreign *Leishmania major* DNA sequence (SEQ ID NO: 9) encoding the 16 amino acid PT3 epitope (SEQ ID NO: 10)[Jardim, 1990]; the protein sequence is indicated in bold type.

The nucleic and amino acid sequences listed in the accompanying sequence listing are shown using standard letter abbreviations for nucleotide bases, and three letter code for amino acids. Only one strand of each nucleic acid sequence is shown, but the complementary strand is understood as included by any reference to the displayed strand.

SEQ ID: 1 shows the agfA DNA sequence
SEQ ID: 2 shows the agfB DNA sequence
SEQ ID: 3 shows the csgA DNA sequence
SEQ ID: 4 shows the csgB DNA sequence
SEQ ID: 5 shows the AgfA amino acid sequence
SEQ ID: 6 shows the AgfB amino acid sequence
SEQ ID: 7 shows the CsgA amino acid sequence
SEQ ID: 8 shows the CsgB amino acid sequence
SEQ ID: 9 shows the DNA sequence encoding the *Leishmania major* PT3 epitope
SEQ ID: 10 shows the *Leishmania major* PT3 epitope amino acid sequence
SEQ ID: 11 shows the agfA::PT3#1 DNA sequence
SEQ ID: 12 shows the AgfA::PT3#1 amino acid sequence
SEQ ID: 13 shows the agfA::PT3#2 DNA sequence
SEQ ID: 14 shows the AgfA::PT3#2 amino acid sequence
SEQ ID: 15 shows the agfA::PT3#3 DNA sequence
SEQ ID: 16 shows the AgfA::PT3#3 amino acid sequence
SEQ ID: 17 shows the agfA::PT3#4 DNA sequence
SEQ ID: 18 shows the AgfA::PT3#4 amino acid sequence
SEQ ID: 19 shows the agfA::PT3#5 DNA sequence
SEQ ID: 20 shows the AgfA::PT3#5 amino acid sequence
SEQ ID: 21 shows the agfA::PT3#6 DNA sequence
SEQ ID: 22 shows the AgfA::PT3#6 amino acid sequence
SEQ ID: 23 shows the agfA::PT3#7 DNA sequence
SEQ ID: 24 shows the AgfA::PT3#7 amino acid sequence
SEQ ID: 25 shows the agfA::PT3#8 DNA sequence
SEQ ID: 26 shows the AgfA::PT3#8 amino acid sequence
SEQ ID: 27 shows the agfA::PT3#9 DNA sequence
SEQ ID: 28 shows the AgfA::PT3#9 amino acid sequence
SEQ ID: 29 shows the agfA::PT3#10 DNA sequence
SEQ ID: 30 shows the AgfA::PT3#10 amino acid sequence

DETAILED DESCRIPTION OF THE INVENTION

Definitions

Fimbriae (pili): Fimbriae are proteinaceous, hairlike appendages produced on the surface of a wide range of bacteria. Fimbriae are generally shorter (several hundred or thousand nm long) and more numerous than flagella (between 100 and 1000 fimbriae per cell) and are usually not involved in cellular motility. Detailed studies of several fimbriae from a variety of animal and human pathogens have revealed that in some case these appendages facilitate bacterial adherence to host tissues [Hultgren, 1996]. Fimbriae are composed of a repeated major subunit protein (fimbrin) and sometimes several minor subunit-like proteins. Fimbrins are polymerized by hydrophobic and hydrophilic interactions to form either thick (7 to 8 nm), rigid structures, thin (2 to 4 nm), flexible filaments or composites of both [Low, 1996].

Thin aggregative fimbriae: Thin aggregative fimbriae (TAF; SEF17) from *S. enteritidis* are thin fibers (3 to 4 nm in diameter) expressed by cells in stationary phase and under conditions of starvation or low osmolarity [Collinson, 1991]. They are extremely aggregative, mediate fibronectin binding [Collinson, 1993], and their expression confers a rough aggregative colony morphology. These fimbriae are characterized as being extremely stable structures; they are not solublized in 5M NaOH or in boiling 0.5% deoxycholate, 8M urea, or 1 to 2% sodium dodecyl sulfate (SDS) with or without 5% β-mercaptoethanol [Collinson, 1991]. Furthermore, these fimbriae remain structurally intact after digestion with proteinase K for up to 2 hours [Collinson, 1999]. Thus far, depolymerization of the fimbriae and release of the fimbrin subunit proteins has only been accomplished by exposing the fimbriae to 90% formic acid [Collinson, 1991;Collinson, 1999]. To our knowledge, this is the only fimbrial type to require such harsh conditions for depolymerization and are thus considered super-stable fimbriae.

Fimbriae as Carriers of Heterologous Epitopes

Fimbriae are proteinaceous, filamentous cell surface structures primarily composed of helically arranged, identical, protein subunits called fimbrins. There are up to 1000 fimbrins per fimbriae and as many as 500 fimbriae per cell. They are found on a wide variety of pathogenic bacteria and are thought to be involved in the colonization of host cell surfaces [Hultgren, 1993]. Therefore, fimbriae may be important for the disease process in vivo.

Advantages of a fimbrial presentation system are the following: 1) the heterologous antigens will be presented in high numbers (up to 500,000 copies per cell), 2) the hybrid fimbrin protein may possess both the immunogenicity and adhesion properties relevant for an efficient live vaccine, 3) the carrier fimbrial subunit proteins are usually strong immunogens, which may be important for directing an immune response against the inserted epitope, and 4) hybrid fimbriae are easy and inexpensive to purify in large amounts (could be used as a vaccine themselves) [Pallesen, 1994]. These advantages make a fimbrial expression system very attractive.

Several strains of *E. coli* produce fimbriae named curli, which are highly related to thin aggregative fimbriae from *Salmonella* spp. Both TAF and curli are primarily composed of one major subunit protein, AgfA and CsgA, respectively. The primary sequence of AgfA and CsgA are 74% identical and 86% conserved [Collinson, 1996]; no other characterized fimbrial proteins in existing sequence databases have notable sequence similarity to either protein. Curli have also been extensively characterized [Bian, 1997; Hammar, 1995; Hammar, 1996; Olsén , 1993; Römling, 1998; Römling, 1998]; the operon encoding curli production has been sequenced and characterized in *E. coli* [Hammar, 1995] and was recently shown to be conserved (identity of 78%) in *Salmonella typhimurium* [Römling, 1998], which also produces thin aggregative fimbriae. This evidence indicates that thin aggregative fimbriae and curli are both members of the same distinct class of fimbriae. The gene for TAF, agfA (csgA) has been detected in 99.8% (603/604) of *Salmonella* isolates, but is less representative in other members of the *Enterobacteriaceae*, including only 19.0% (26/137) *E. coli* strains [Doran, 1993]. agfA is therefore genotypic of *Salmonella* spp. and occasionally found in *E. coli* and its subspecies, suggesting its origins were in *Salmonella* spp. and coopted into *E. coli.*

Figure 5A:
FIG. 5. Immunogold electron microscopy of *S. enteritidis* strains containing recombinant agfA in the chromosome. *S. enteritidis* strains analyzed after growth on T plates (A, C, D) or in T broth (B, E, F) for 24 h at 37° C., static. Immunogold labeling was performed with antiserum raised to thin aggregative fimbriae followed by protein A-15 nm gold (A, B, C, E) or with antiserum raised to the PT3 epitope followed by goat-anti-rabbit-5 nm gold (D, F). A. *S. enteritidis* A+ control strain grown on T plates, reacted with immune serum raised to thin aggregative fimbriae. B. *S. enteritidis* A+ control strain grown in T broth, reacted with immune serum raised to thin aggregative fimbriae. C. *S. enteritidis* strain A7 grown on T plates, reacted with immune serum raised to thin aggregative fimbriae. D. *S. enteritidis* strain A7 grown on T plates, reacted with immune serum raised to PT3. E. *S. enteritidis* strain A4 grown in T broth, reacted with immune serum raised to thin aggregative fimbriae. F. *S. enteritidis* strain A4 grown in T broth, reacted with immune serum raised to PT3.
Figure 5B:
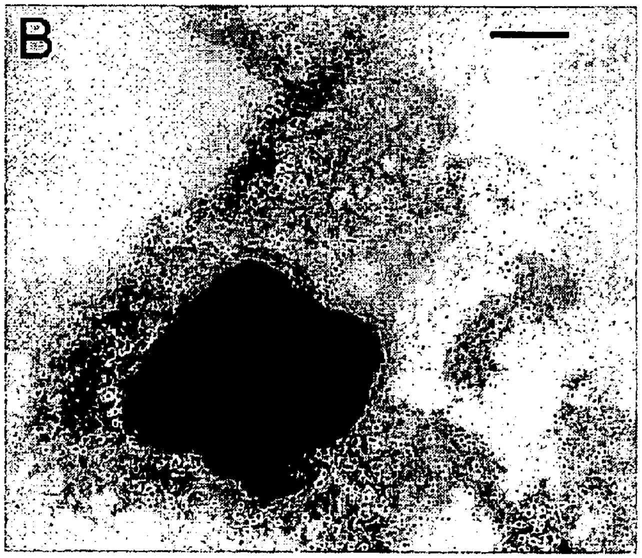

AgfA is characterized as having a two-domain structure with a 22 residue protease-susceptible N-terminal region and a 109 residue protease-resistant C-terminal core region [Collinson, 1999]. This C-terminal core region has five-fold sequence homology as represented in FIG. 5B and is predicted to comprise a primarily β-sheet structure. The first 18 amino acids of each of the five segments conformed to the consensus sequence $Sx_5QxGx_2NxAx_3Q$ (SEQ ID NO: 59) separated by 4 or 5 additional residues except for the terminal repeat which ended in Y. Analysis of this five-fold sequence homology has yielded a hypothetical, parallel β-helix, three-dimensional structure for AgfA [Collinson, 1999] and this model is displayed in FIG. 5C.

AgfB is proposed to be a minor component of thin aggregative fimbriae and shares high secondary structure similarity to AgfA. It is the same size as AgfA and the overall primary sequence homology is 22% identity and 42% similarity. The majority of conserved residues keep the consensus sequence intact (described above for AgfA); based on this, AgfB is proposed to have a similar three dimensional structure.

Assembly of thin aggregative fimbriae: The majority of fimbrial assembly systems in Gram negative bacteria follow the chaperone/usher pathway [Hultgren, 1996]. In this system, the chaperone protein facilitates the release of fimbrin subunits from the cytoplasmic membrane, prevents premature aggregation and targets the subunits to the usher protein in the outer membrane which allows them to pass through and assemble into fimbrial fibers [Thanassi, 1998]. The prototypical fimbriae for this system are the Pap or P fimbriae from *E. coli* and Type 1 fimbriae from *E. coli* and *Salmonella* [Hultgren, 1996]. Another well characterized assembly system is that of Type IV fimbriae produced by *Pseudomonas aeruginosa, Neisseria* spp., *Moraxella bovis, Dichelobacter nodosus,* and *Vibrio cholerae*. These fimbriae apparently bypass the need for specialized chaperone and usher proteins and utilize a branch of the general secretion pathway (type II) which is widely used for the secretion of many other extracellularly targeted proteins [Salmond, 1996]. Many homologues to the fimbrial types described above have been characterized; almost without exception, growth of the fimbrial fiber is achieved from the base by addition of the subunits from the periplasmic side of the outer membrane.

In contrast, thin aggregative fimbriae (curli) are proposed to assemble via a unique and novel mechanism described as extracellular, nucleator-dependent assembly [Hammar, 1996]. In this model, AgfA monomers are secreted from the cell (across the outer membrane) in a soluble, polymerization-competent form and are proposed to polymerize into insoluble fimbrial fibers on the cell surface upon interaction with a cell-bound nucleator. AgfB is proposed to function as the nucleator, inducing a conformational change in soluble AgfA leading to polymerization [Bian, 1997]. Once an initial interaction has occurred between AgfB and an AgfA monomer, the extension of the fiber is probably self-driven with the addition of AgfA monomers to the free, distal end. AgfB is also proposed to be a minor component of the fibers. Several other proteins are involved in biogenesis of TAF; AgfG may perform a chaperone-like function to protect AgfA and AgfB from proteolytic degradation or may form a multimeric channel in the outer membrane to allow passage of agfA or AgfB [Loferer, 1997], AgfD acts as a positive transcriptional regulator for TAF expression [Hammar, 1995], AgfE is proposed to be involved in Congo red and fibronectin binding and AgfF is proposed to be involved in nucleation [Römling, 1998].

The conformational change proposed to occur in AgfA might involve a conversion from a partially disordered structure in the monomeric state to readily ordered secondary structures in the polymeric state as has been observed with assembly of the bacterial flagellar filament [Aizawa, 1990]. TAF assembly would be driven then by conformationally altered AgfA which could bind the next soluble AgfA monomer and induce a similar conformational change. Repetition of this process would result in the formation of the long-insoluble fibers observed with TAF and bears similarity to the scrapie protein changing from soluble to insoluble upon formation of rod-like prion superstructures [Cohen, 1994]. This assembly model is unique among bacterial surface organelles characterized to date.

Epitope: An epitope refers to an immunologically active region of an immunogen (protein) that binds to specific membrane receptors for antigen on lymphocytes or to secreted antibodies [Kuby, 1994]. To generate an immune response to a foreign antigen, lymphocytes and antibodies recognize these specific regions (epitopes) of the antigen rather than the entire molecule.

B cell epitope: The region of an immunogen (protein, polysaccharide, or lipid) which is recognized by B cells when it binds to their membrane bound antibody. The B cells which recognize that particular region then proliferate and secrete antibody molecules which are specific for that region of the immunogen. B cell epitopes tend to be highly accessible regions on the exposed surface of the immunogen. Stimulation of the immune system by B cell epitopes results in "humoral" immunity.

T cell epitope: The region (epitope) of an immunogen which is recognized by a receptor on T cells after being processed and presented on the surface of an antigen presenting cell (APC) in the context of a major histocompatability complex (MHC) class I or II molecule. T cells can be split into two distinct groups, T helper cells ($T_h$) and T cytotoxic cells ($T_c$). T helper cells recognize epitopes bound to MHC class II molecules whereas T cytotoxic cells recognize epitopes bound to MHC class I molecules. T helper cells can be further subdivided into two classes, $T_{h1}$ and $T_{h2}$, Th1 being responsible for stimulation of cell-mediated immunity and Th2 cells stimulating the humoral arm of the immune system. When a given T cell recognizes the epitope-MHC complex at the surface of the APC it becomes stimulated and proliferates, leading to the production of a large number of T cells with receptors specific for the stimulating epitope. Stimulation of the immune system by T cell epitopes normally results in "cell-mediated" immunity.

Chromosomal gene replacements: This refers to the replacement of a wild-type gene sequence in the bacterial chromosome with an in vitro-altered recombinant gene sequence.

Attenuated Bacterial Vaccine: This refers to bacterial strains which have lost their pathogenicity while retaining their capacity for transient growth within an inoculated host. Because of their capacity for transient growth, such vaccines provide prolonged immune-system exposure to the individual epitopes on the attenuated organisms, resulting in increased immunogenicity and memory-cell production, which sometimes eliminates the need for repeated booster injections. The ability of many attenuated vaccines to replicate within host cells makes them very suitable to induce a cell-mediated immunity. Typically, bacterial strains are made attenuated by introducing multiple defined gene mutations into the chromosome thereby impairing growth in vivo.

Recombinant Vector Vaccine: This refers to the introduction of genes (or pieces of genes) encoding major antigens (or epitopes) from especially virulent pathogens into attenuated viruses or bacteria. The attenuated organism serves as a vector, replicating within the host and expressing the gene product of the pathogen.

Sequence Identity: Identity between two nucleic acid sequences, or two amino acid sequences is expressed in terms of the level of identical residues shared between the sequences. Sequence identity is typically expressed in terms of percentage identity; the higher the percentage, the more similar the two sequences are.

Sequence Similarity: Similarity between two amino acid sequences is expressed in terms of the level of sequence conservation, including shared identical residues and those residues which differ but which share a similar size, polarity, charge or hydrophobicity. Sequence similarity is typically expressed in terms of percentage similarity; the higher the percentage, the more similar the two sequences are.

Recombinant: A recombinant nucleic acid is one that has a sequence that is not normally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Oligonucleotide (oligo): A linear polymer sequence of up to about 100 nucleotide bases in length.

Probes and primers: Nucleic acid probes and primers may readily be prepared based on the amino acid and DNA sequence provided by this invention. A probe comprises an isolated nucleic acid attached to a detectable label or reporter molecule. Typical labels induce radioactive isotopes, ligands, chemiluminescent agents, and enzymes. Methods for labeling and guidance in the choice of labels appropriate for various purposes are discussed, e.g., in Sambrook et al. [Sambrook, 1989].

Primers are short nucleic acids, preferably DNA oligonucleotides 15 nucleotides or more in length. Primers may be annealed to a complementary target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in Sambrook, 1989, Ausubel, 1987, and Innis, 1990. PCR primer pairs can be derived from a known sequence, for example, by using computer programs intended for that purpose such as DNAStar Lazergene software. One of skill in the art will appreciate that the specificity of a particular probe or primer increases with its length. Thus, for example, a primer comprising 20 consecutive nucleotides will anneal to a target with a higher specificity than a corresponding primer of only 15 nucleotides. Thus, in order to obtain greater specificity, probes and primers may be selected that comprise 20, 25, 30, 35, 40, 50 or more consecutive nucleotides.

Isolated: An "isolated" biological component (such as nucleic acid or protein or organelle) has been substantially separated or purified away from other biological components in the cell of the organism in which the component naturally occurs, i.e., other chromosomal and extrachromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids. An "isolated" bacterial strain or colony is purified away from other colonies and yields a pure culture without any contaminants upon plating on selective media.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art. A "temperature-sensitive" vector is one which replicates normally at a low growth temperature (i.e., 28° C.) and will not replicate at a higher growth temperature (i.e., 42° C.) due to mutations at or near the origin of replication. An "imperfectly segregating" vector is one which is not stably inherited by new daughter cells at the time of cell division in the absence of selection pressure due to mutations within the vector sequence.

Operon: An operon is the term used to describe a DNA sequence that codes for one or more polypeptides (structural genes), usually of related function, and a DNA sequence that regulates the expression of these genes.

Selection of *Salmonella* and Thin Aggregative Fimbriae

*Salmonella* spp. are well developed vaccine vectors [Hackett, 1993]. Attenuated *Salmonella* strains can elicit protective immunity and induce secretory, humoral and cellular anti-*Salmonella* responses in hosts following oral immunization [Levine, 1996]. In addition, most *Salmonella* spp. are facultative intracellular pathogens [Fields, 1986] with a highly characterized invasion pathway [Galán, 1996] and can express antigens inside of host cells. These features, when combined with the ease of genetic manipulation in *Salmonella* spp., makes these facultative intracellular pathogens excellent candidates as vaccine vectors for the presentation of protective heterologous antigens [Curtiss III, 1994].

Thin aggregative fimbriae were selected as the carriers of heterologous sequences because they represented a novel, super-stable class of fimbriae among the enterobacteriacea [Low, 1996]. They can be expressed at high levels and are surface-exposed [Collinson, 1991]. The biochemical and immunological characteristics of the major subunit protein, AgfA, have been well characterized [Collinson, 1991; Collinson, 1992; Collinson, 1993] and most of the genes in the operon required for assembly have been identified [Hammar, 1995; Collinson, 1996; Römling, 1998]. The structural gene, agfA, of TAF was found to be widely distributed and is probably common among *Salmonella* spp. All of these factors made TAF an ideal choice for testing as a carrier of heterologous sequences.

Selection of the PT3 Epitope

Several immunoprotective T cell epitopes have been identified from the GP63 protein of *Leishmania major*, and were found to stimulate the proliferation of lymphocytes from mice immunized with whole GP63 [Jardim, 1990]. One of these epitopes, PT3, comprising residues 154–168 of the mature protein, specifically induced proliferation of $CD4^+$ T cells of the $T_{h1}$ subset, known to be involved in the development of cell-mediated immunity [Jardim, 1994]. A further study proved that a single immunization with synthetic PT3 in adjuvant was able to protect Balb/c mice against challenge with *L. major* promastigotes [Spitzer, 1998]. Furthermore, studies with *Salmonella* vaccine strains expressing GP63 from an extrachromosomal vector have demonstrated that oral vaccination against *Leishmania* infection is possible [McSorley, 1997]. Therefore, PT3 is a good candidate for developing and testing a heterologous fimbrial vaccine system in *Salmonella*.

Method of Gene Replacement within the *Salmonella enteritidis* agfBAC Operon

Several methods of chromosomal gene replacement have been developed for the creation of *Salmonella* vaccine vectors (discussed above). However, these methods insert the recombinant genes into the chromosome at non-native sites. As a consequence, expression of the recombinant genes would be predicted to be altered. There is a need for a method of chromosomal gene replacement in *Salmonella* to insert recombinant genes into native regions normally occupied by the wild-type genes. Two such methods exist for chromosomal gene replacements in *E. coli*. The method by Hamilton et al. (1989) relies on the use of a temperature sensitive pSC101-derived vector to perform the replacements. Gene replacement by this method does not leave (or add) any extraneous DNA elements and one drawback is having to cure final strains of freely replicating vectors. A more recent method proposed by Link et al. (1997) uses a vector related to the one used by Hamilton et al. (1989) with the addition of the sacB selectable marker to the vector to allow for selection for loss of the vector sequence upon gene replacement.

The method of chromosomal gene replacement according to the present invention also uses a temperature-sensitive pSC101-derived vector, pHSG415 [Hashimoto-Gotoh, 1981], but has some notable differences.

Generation of Recombinant *S. enteritidis* Fimbrin Genes

Figure 1B:
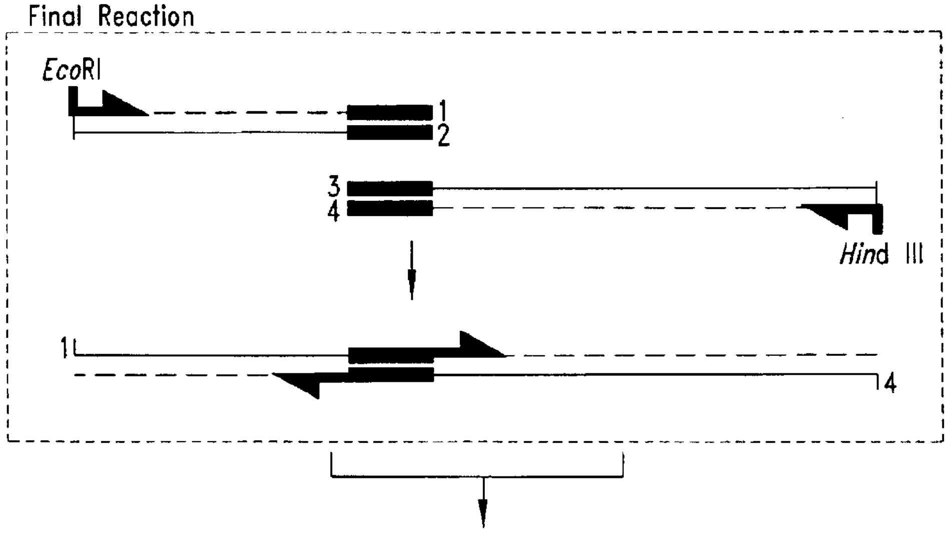
Figure 1C:
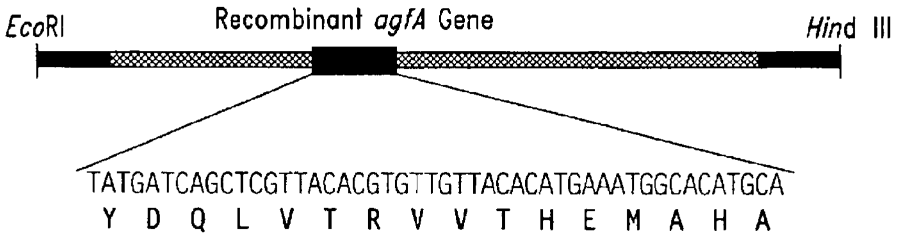

The *S. enteritidis* 3b agfA fimbrin gene was chosen to receive a site-specific epitope replacement with the PT3 epitope. The two-step overlap extension PCR method of Horton et al. [Horton, 1989] was used (FIGS. 1A, B) to replace 48 bp of the fimbrin gene with 48 bp encoding the PT3 T cell epitope from *L. major* (FIG. 1C). The PCR-generated gene encoded an AgfA protein carrying the PT3 epitope within a specific region (residues 111–126 in AgfA). The resultant agfA::PT3 PCR products were sequenced and cloned into pHSG415 (FIG. 2A) to generate the recombinant temperature-sensitive vector pHSAP7.

Gene Replacement in *S. enteritidis*

*S. enteritidis* 3b cells were transformed with pHSAP7 and grown 24 h in liquid media (Terrific broth with Ampicillin; TFB/Ap). This culture was transfered five consecutive times into fresh media for a total growth period of 120 h before plating on LB/Ap. 50 isolated colonies were picked and 100% were identified by PCR to contain the integrated vector sequence. Four pHSAP7 cointegrate colonies were selected and grown at the permissive temperature of 28° C. in liquid media (TFB) without Ap selection pressure for 24 h and transferred five consecutive times into fresh media for a total growth period of 120 h at 28° C. Colonies were plated onto LB and LB/Ap plates to determine the percentage of $Ap^S$ colonies. 184 isolated colonies were picked from each cointegrate culture, yielding 27%, 15%, 10% and 9% $Ap^S$ from the four pHSAP7 cointegrates as shown in Table 1.

TABLE 1

Efficiency of agfA chromosomal gene replacement in *S. enteritidis.*

| Plasmid cointegrate colonies (%) | $Ap^S$ colonies[a] # | Chimeric gene % | replacements |
|---|---|---|---|
| pHSAP7 | | | |
| Isolate #2 | 18 | 10 | 7[b] |
| Isolate #3 | 28 | 15 | 10[b] |
| Isolate #9 | 49 | 27 | 4[b] |
| Isolate #10 | 17 | 9 | 8[b] |

[a]184 individual colonies picked in total.
[b]Frequency of agfA::PT3 containing *S. enteritidis* estimated by CR binding morphology (TCR).

Genetic Analysis of *S. enteritidis* Strains Containing Recombinant agfA::PT3

To identify *S. enteritidis* strains containing the chimeric agfA::PT3 gene, five of the final $Ap^S$ colonies were chosen and were analyzed by PCR. Three strains were identified as having the PT3 DNA sequence within agfA and all five strains were negative for the pSC101 ori sequence as above. PCR products from each strain were the same size as PCR products of agfA from *S. enteritidis*, indicating that there was no additional plasmid sequence inserted in this region. Final confirmation of the genotypes of these strains was obtained by DNA sequencing proving that three strains contained agfA::PT3 and two strains contained wild-type agfA. Thus, these data confirmed the creation of *S. enteritidis* strains containing chimeric sefA::PT3 or agfA::PT3 fimbrin genes by precise recombination events.

The existing methods of chromosomal gene replacement are less favorable than the present method. The method of Hamilton et al. [Hamilton, 1989] results in final strains containing freely replicating plasmids which must be cured before selecting gene replacements, whereas the method of the invention results in a high proportion of final strains which have lost the excised plasmid altogether and can be screened directly by PCR. The method of Link et al. [Link, 1997] includes the *Bacillus subtilis* sacB system to enable direct selection for excision and loss of integrated plasmids. However, when creating deletion mutants without the use of selectable markers, these authors reported lower frequencies than are reported here (Table 1). A recent study by Edwards et al. [Edwards, 1998] reported the replacement of sefA or agfA within *S. enteritidis* at lower frequencies than reported here, even with the use of a $Km^R$ marker in the recombinant genes. This supports the usefulness of the present method and demonstrates that the high replacement frequencies reported here are not simply due to the ease of sefA or agfA replacement. Therefore, this method has broad application and appeal for gene replacement in *Salmonella* and other enteric bacteria capable of supporting the replication of pSC101-derived plasmids. In addition, the present results suggest that the use of similar "unstable" plasmids in other organisms could represent a more generalized mutagenesis strategy.

A closer look at the properties of pHSG415 can help explain why this gene replacement method is so efficient. In contrast to pSC101, pHSG415 was shown to be extremely unstable in liquid culture in the absence of selection pressure, with as few as 60% of cells carrying the plasmid after 24 hr [Caulcott, 1987]. These authors speculated that the difference between pSC101 and pHSG415 was due to the absence of most of the par locus in pHSG415. The pSC101 par locus has been very well characterized; it has been shown to alter the binding of proteins within the origin region [Ingmer, 1993] and thus to enhance DNA replication [Manen, 1990]. In addition, it contains a preferential binding site for DNA gyrase [Wahle, 1988] and alters the negative supercoiling of DNA [Miller, 1990]. Through a combination of these effects the par locus promotes partitioning of plasmids to daughter cells at the time of cell division [Meacock, 1980]. Due to the deletion of the par locus, pHSG415 is proposed to have a defect in its segregating properties causing unequal partitioning of plasmid molecules to daughter cells at the time of cell division [Caulcott, 1987]. Although the present invention is not bound by a specific mechanisms, it is proposed that the present method uses the unstable properties of pHSG415 to advantage, and in the absence of selection pressure, integrated plasmids are lost immediately after the second crossover event or are retained for several generations and then lost. Thus, a replacement of the agfA gene in a wild-type strain of *S. enteritidis* was performed at an efficiency of 10% without any accompanying antibiotic resistance markers in the target genes.

Specific DNA Sequence Replacements within agfA

Expression of Heterologous Epitopes in *E. coli* Fimbriae

Several *E. coli* fimbrial types have been utilized for the presentation of heterologous sequences. The fimbriae used as carriers thus far have been type 1 fimbriae [Hedegaard, 1989; Stentebjerg-Olesen, 1997], K88 fimbriae [Bakker, 1990; Thiry, 1989], P fimbriae [van der Zee, 1995; van Die, 1990], CS31A fimbriae [Der Vartanian, 1997] and type 4 fimbriae [Jennings, 1989]. All were chosen because their expression systems and biochemical properties were relatively well characterized in comparison to other fimbrial types of *E. coli.*

In summary, foreign antigenic determinants (epitopes) from various organisms were tested for insertion or replacement into the major structural subunit protein of the fimbriae, such as: epitopes from the hepatitis B virus surface antigen, foot-and-mouth disease virus (FMDV), Poliovirus type 1, cholera toxin B, *Mycobacterium leprae, Plasmodium falciparum,* Transmissible gastroenteritis virus (TGEV), human influenza virus, *Neisseria gonorrhoeae* fimbrin subunit as well as the hormones gonadotropin releasing hormone and somatostatin. Positions for insertion or replacement were typically selected based on hydrophilicity profiles of the subunit sequence, sequence variability among different serovars and/or linker scanning mutagenesis. In each study, the foreign sequence (epitope) was detected using antibodies directed against these sequences. In many cases fimbriae were expressed, but this depended on the size and sequence of the foreign epitope and the position used within the subunit protein. These studies have shown that it is possible to construct bacterial strains expressing recombinant fimbriae carrying immunologically active foreign sequences without seriously affecting the properties of the fimbriae. There were some problems with these fimbrial expression systems, however. In each study, expression of the mutant fimbrin genes was directed from a recombinant vector transformed into *E. coli* and the researchers had to reconstitute the expression of the fimbriae. Therefore, conditions for expression might not represent the physiological conditions in wild-type cells.

No similar studies using *Salmonella* fimbriae as carriers of heterologous antigens have been published to date. This is due in part to the fact that *Salmonella* fimbriae have not been as well characterized as their *E. coli* counterparts. Flagella, on the other hand, have been quite well characterized in *Salmonella*. Accordingly, studies have been done in *Salmonella* using flagella as carriers of heterologous antigens. The results of these studies are outlined below.

Expression of Heterologous Epitopes in *Salmonella* Flagella

Research into the area of expression of epitopes on flagella has been previously published [Newton, 1989; Newton, 1991; Newton, 1995; Wu, 1989; Verma, 1995; Verma, 1995; Cattozzo, 1997]. Flagellin studies have involved the insertion of various foreign DNA sequences into a single, hypervariable region of the major phase-1 flagellin subunit gene of an attenuated strain of *Salmonella*. Some of the epitopes that have been tested in this system are from Cholera toxin B, Hepatitis B surface antigens, *Streptococcus pyogenes* M protein, HIV-1, Influenza A hemagglutinin, *Plasmodium* spp., Rotavirus, *Corynebacterium diptheriae, Listeria monocytogenes* listeriolysin and Moth cytochrome c. Like the fimbrial systems described above, production of assembled flagella on the surface of the *Salmonella* cells was dependent on the sequence and length of the foreign epitope. Many of the studies tested the immunogenicity of the heterologous epitopes inserted in *Salmonella* flagellin by injecting the whole strain into mice, rabbits or guinea pigs; almost all immunized animals developed an Ab response to the epitope, proving that these sequences were still antigenic when expressed in flagella. Other studies showed that cell-mediated immunity could be obtained also [Verma, 1995; Verma, 1995] although this may depend on the particular epitope tested [Vanegas, 1997]. Finally, purified recombinant flagella can elicit humoral and cell-mediated immune responses when administered alone [Levi, 1996].

The data obtained from these flagella studies indicate that an epitope can retain its immunogenicity even when expressed in the context of an unrelated protein. They also prove the effectiveness of *Salmonella* as a live attenuated vaccine. However, there are some problems, the major one being the relatively low expression levels of flagella on bacterial cells (<10 copies per cell) compared to high-expression levels of fimbriae (100–1000 per cell) or other cell-surface organelles.

AgfA as a Carrier of the PT3 Epitope

Figure 5C:
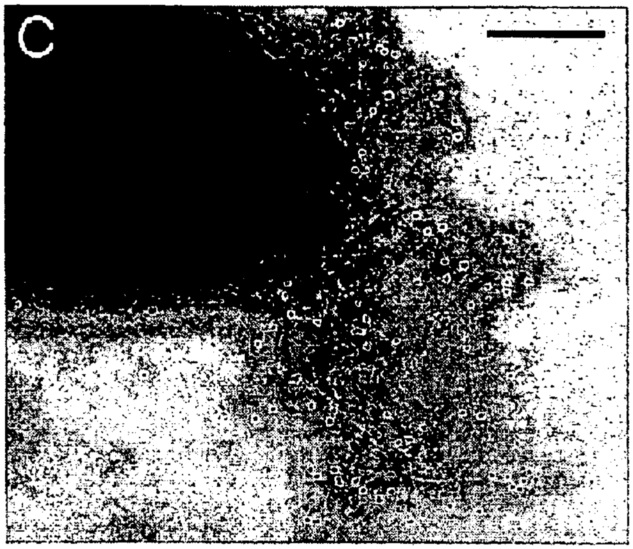
Figure 5D:
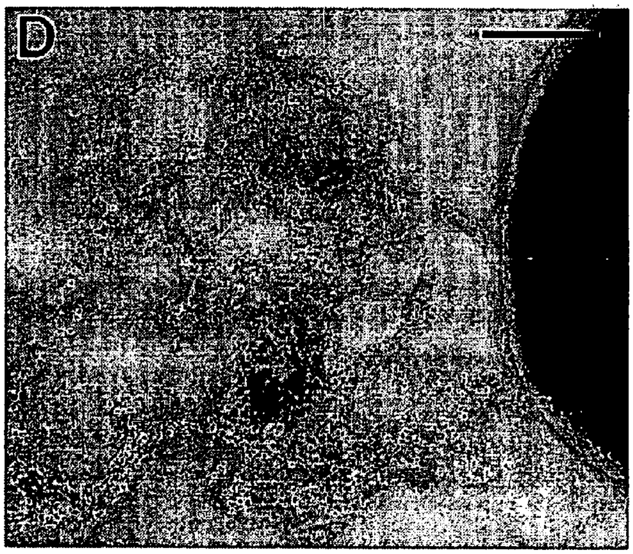
Figure 5E:
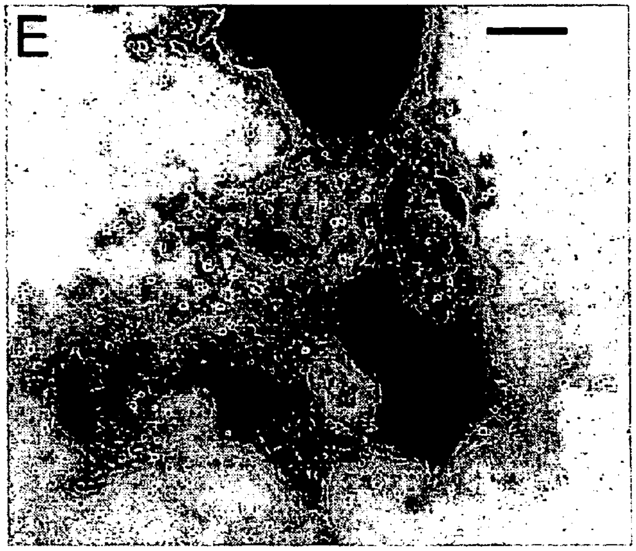
Figure 5F:

Ten different 16 amino acid segments within AgfA were chosen for replacement with the PT3 epitope and are highlighted in FIGS. 5B and 5C. These replacement regions were chosen using several criteria: primary sequence alignment, regions A1 and A2 (red); protease-susceptibility data [Collinson, 1999], region A3 (black; not represented in FIG. 5C); secondary structure predictions matching the β-sheet half of PT3 with β-sheet regions in AgfA, regions A4-A7 (blue); and secondary structure predictions matching the a-helical half of PT3 with β-sheet regions of AgfA, regions A8-A10 (yellow). In total, all 131 residues within AgfA, except 6 in the N-terminal region and 8 at the extreme C-terminus, were replaced with the PT3 sequence in at least one of the chimeric fimbrin constructs.

Generation of *S. enteritidis* Strains Containing the agfA::PT3 Genes

All recombinant agfA::PT3 genes were generated by PCR, sequenced and introduced into the chromosome of *S. enteritidis*, replacing the $W^+$ agfA gene, using the procedure described above. All bacterial strains used are outlined below in Table 2.

TABLE 2

*S. enteritidis* strains used in this study.

| Strain | Description and relevant genotypes |
|---|---|
| 3b | wild-type |
| 2–2a | agfA:: TnphoA fusion in chromosome |
| A+ | similar to wild-type |
| A1 | agfA::PT3#1 in chromosome |
| A2 | agfA::PT3#2 in chromosome |
| A3 | agfA::PT3#3 in chromosome |
| A4 | agfA::PT3#4 in chromosome |
| A5 | agfA::PT3#5 in chromosome |
| A6 | agfA::PT3#6 in chromosome |
| A7 | agfA::PT3#7 in chromosome |
| A8 | agfA::PT3#8 in chromosome |
| A9 | agfA::PT3#9 in chromosome |
| A10 | agfA::PT3#10 in chromosome |

Figure 2A:
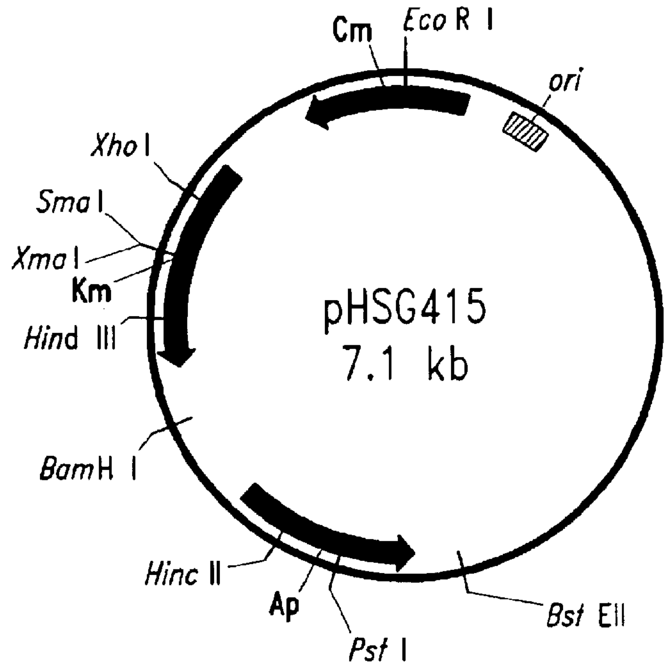
FIG. 2. Generation of *S. enteritidis* strains carrying recombinant agfA. A. Map of pHSG415 indicating positions of unique restriction endonuclease sites, antibiotic resistance genes (black arrows) and temperature-sensitive origin of replication (ori). Figure adapted from [Hashimoto-Gotoh, 1981]. B. Gene replacement strategy. Transformed *S. enteritidis* was grown at 42° C. with selection pressure to induce a single crossover event and subsequent integration of pHSSP10 into the chromosome. Plasmid cointegrates were grown at 28° C. without selection pressure to induce a second crossover event and loss of the pHSG415 sequence, resulting in one of two possibilities: 1) wild-type agfA or 2) recombinant agfA.
Figure 2B:
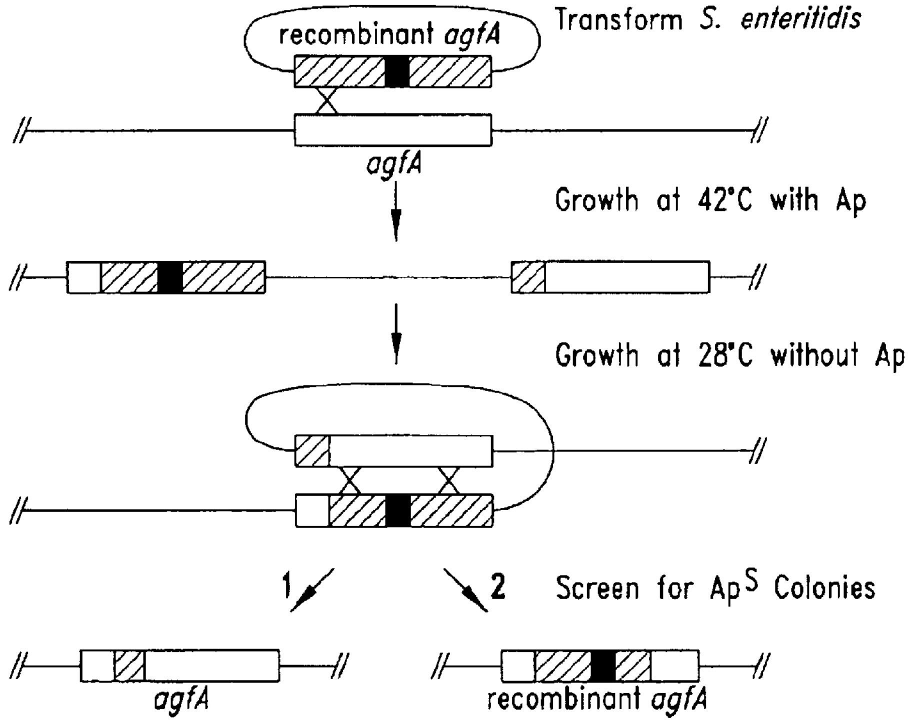
Figure 6A:
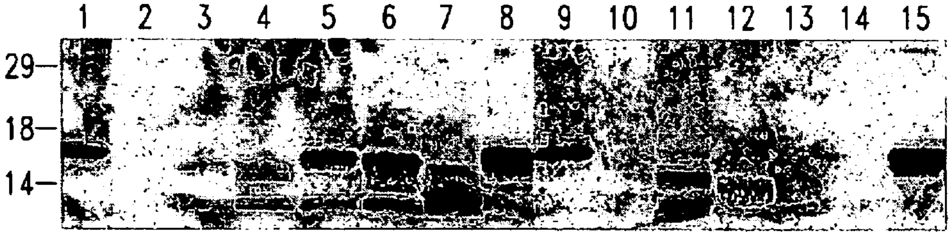
FIG. 6. Resistance of the recombinant TAF fibers expressed in *S. enteritidis* to proteinase K treatment. Samples prepared as in FIG. 2 but treated with proteinase K (0.5 mg/ml) before loading on SDS-PAGE. *S. enteritidis* 3b 2-2a (lane 2), A1 (lane 3), A2 (lane 4), A3 (lane 5), A4 (lane 6), A5 (lane 7), W+ 3b (lane 8), A6 (lane 10), A7 (lane 11), A8 (lane 12), A9 (lane 13), A10 (lane 14) and A+ control strain (lane 15) are represented. Purified SEF17 is represented in lanes 1 and 9. The blots were reacted with immune serum generated against SEF17. The molecular mass markers are shown on the left of each blot. A. Samples digested with proteinase K for 1 hour. B. Samples digested with proteinase K for 2 hours.
Figure 6B:
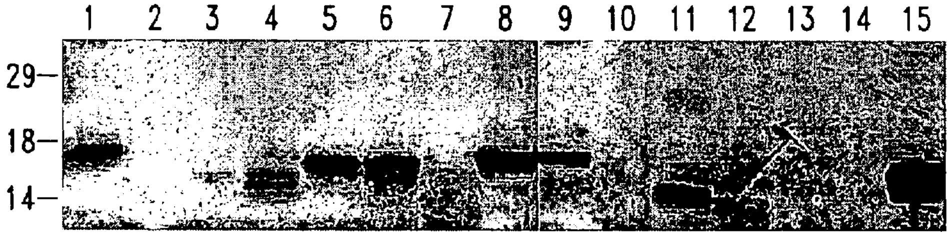

Western Blot Analysis of *S. enteritidis* Strains Containing agfA::PT3 in the Chromosome The recombinant *S. enteritidis* strains A1–A10 were grown on T plates at 37° C. for 24 h and were analyzed for production of recombinant AgfA proteins containing the PT3 epitope. Replicate Western blots are shown in FIGS. 2A and 2B, reacted with either anti-TAF or anti-PT3 immune sera. All 10 chimeric strains were expressing their corresponding recombinant AgfA::PT3 proteins, although strains A1 and A10 (FIG. 6, lanes 3 and 14) expressed much lower levels. All chimeric fimbrin proteins differed from AgfA in that they could be detected to some degree on Western blots without formic acid pre-treatment. Proteins from strains A5, A6, A8, and A9 (FIG. 6A lanes 7, 10, 12, and 13, respectively) appear smaller than purified AgfA (17 kDa; FIG. 6A lanes 1 and 9). The nature of these size or moblility differences was not investigated. These data confirmed the expression of the 10 chimeric AgfA::PT3 proteins from the chromosome of *S. enteritidis.*

Immunogold Electron Microscopy of *S. enteritidis* Strains Containing agfA::PT3

Figures 3A, 3B:
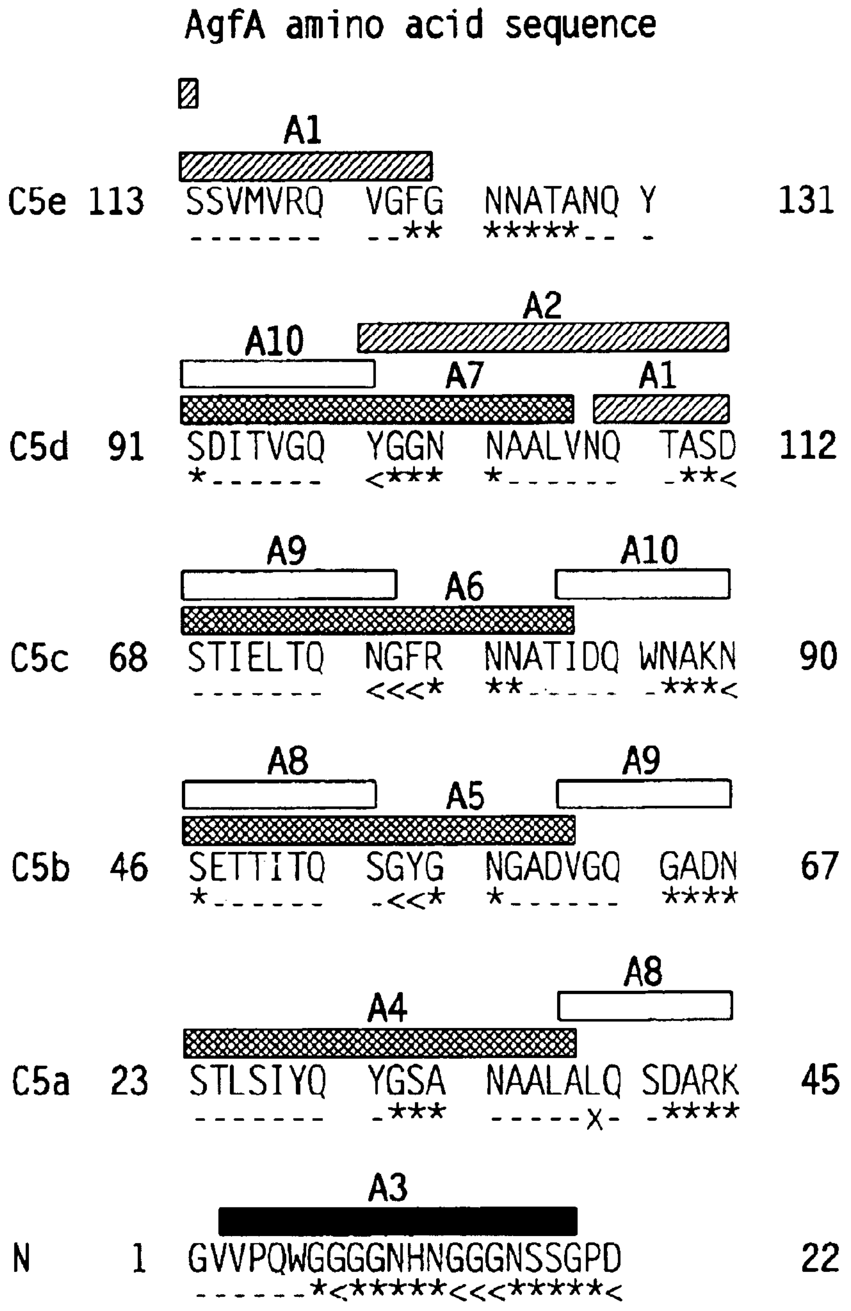
FIG. 3. PT3 epitope replacement in AgfA. A. Peptide sequence of the PT3 epitope from GP63 of *Leishmania major* (SEQ ID NO: 10)[Jardim, 1990]. Predicted secondary structure (Garnier-Robson algorithm, DNAStar software) is listed below the peptide sequence: (–) β-strand; (x) β-helix. B. Schematic diagram of the mature agfA protein (SEQ ID NO: 31) illustrating the regions replaced by the PT3 epitope sequence; regions A1 to A10 are indicated with the colored boxes above the sequence. The five-fold internal sequence homology of AgfA is represented by regions C5a–e with the consensus sequence $Sx_5QxGx_2NxAx_3Q$ (SEQ ID NO: 59), with the 22-residue N-terminal region listed at the bottom. Predicted secondary structure (Garnier-Robson algorithm, DNAStar software) is listed below the protein sequence: (–) β-strand; (x) β-helix; (*) random coil; (<) turn.
FIG. 3C. The predicted parallel β-helix model of AgfA (residues 23–130) viewed from the front side [Collinson, 1999]. The five-fold repeat segments (C5a–e) and colored residues, representing regions in AgfA replaced with PT3, refer back to the diagram in (B). Color Code: Blue=regions A4, A5, A6, A7; Yellow=regions A8, A9, A10; Red=regions A1, A2; Green=blue and yellow overlap; Orange=blue, yellow and red overlap; Purple=blue and red overlap; Grey=unreplaced sequence.
Figure 3C:
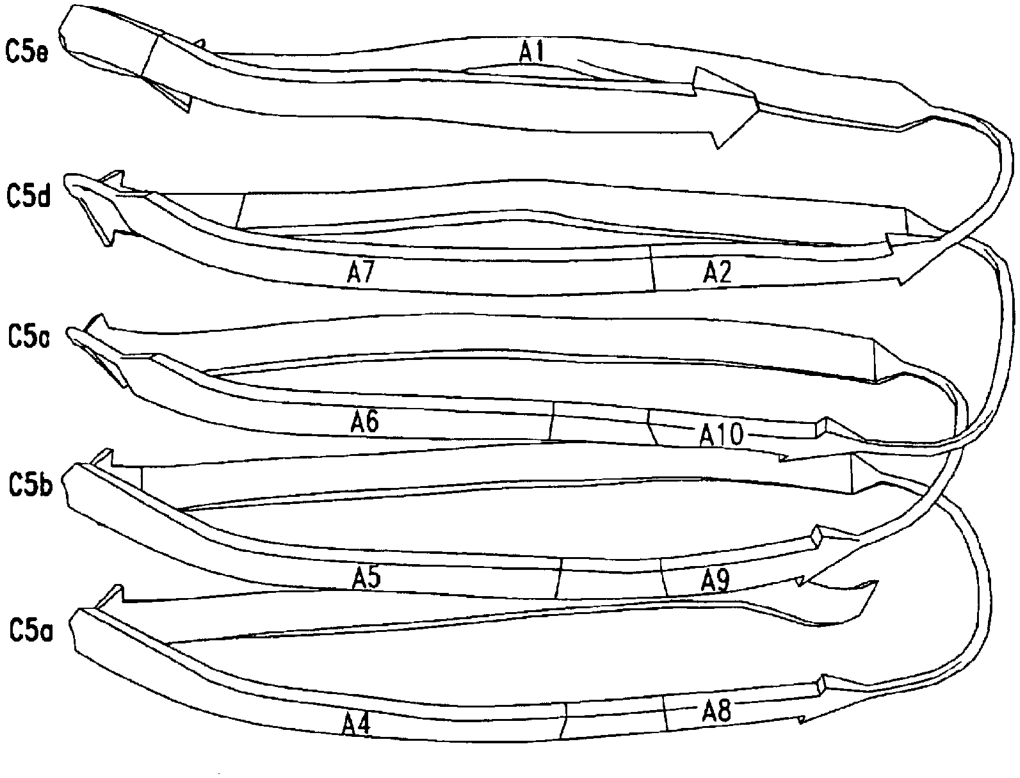
Figure 4A:
FIG. 4. Western blot analysis of the 10 different *S. enteritidis* strains containing recombinant agfA in the chromosome. Formic acid treated SDS-PAGE sample buffer-glycine insoluble material from scraped whole cells of *S. enteritidis* 3b 2-2a (lane 2), A1 (lane 3), A2 (lane 4), A3 (lane 5), A4 (lane 6 ), A5 (lane 7), W+ 3b (lane 8), A6 (lane 10), A7 (lane 11), A8 (lane 12), A9 (lane 13), A10 (lane 14) and A+ control strain (lane 15) grown on T plates. Purified SEF17 is represented in lanes 1 and 9. The molecular mass markers are shown on the left of each blot. A. Blot reacted with immune sera raised to SEF17. B. Blot reacted with immune sera raised to PT3.
Figure 4B:

To determine whether the recombinant AgfA fimbrins expressed by *S. enteritidis* strains A1–A10 were being assembled into fimbrial fibers, immunogold labeling was performed with immune sera against TAF or PT3. Recombinant fimbrial fibers were observed on the surface of cells from strains A2–A9 in 8 out of 10 strains (representative EMs are shown in FIG. 3). These fibers were distinct with definite cell surface contact points and looked very similar to $W^+$ TAF from *S. enteritidis* 3b (FIG. 3), although the number of chimeric fimbrial fibers was slightly reduced in all cases. Strains A3, A4, A5 and A8 were judged to be the most similar to $W^+$ *S. enteritidis* 3b in terms of number of fibers per cell, the frequency of labelled cells, and the distinctness of the individual fibers. In contrast to the other *S. enteritidis* strains, A1 and A10 did not display consistent labeled fimbrial fibers at the cell surface, although some individual cells did show labeling. Thus, these results indicated that 8 of the 10 recombinant AgfA::PT3 proteins were efficiently assembled into fimbrial fibers displayed at the cell surface of *S. enteritidis.*

Since growth on solid media is a relatively static environment, the production of recombinant fimbrial fibers in broth culture was examined to determine whether they were stably attached to the *S. enteritidis* cell surface. Immunogold electron microscopy was performed as above on cells grown at 37° C. for 24 h in T broth; representative EMs are shown in FIG. 3. These results were very similar to those observed for cells grown on T plates, although more non-cell-associated fimbrial fibers were observed on the T broth grids. Again, *S. enteritidis* strains A2–A9 had significant amounts of cell-associated recombinant fimbrial fibers with strains A3, A4, A5, and A8 being the most similar to $W^+$ *S. enteritidis* 3b. However, like the T plate samples, A2–A9 were judged to have slightly fewer and less distinct fimbrial fibers than $W^+$. No consistent cell-associated chimeric fimbrial fibers were observed for *S. enteritidis* strains A1 and A10 . These results confirmed that 8 of the 10 AgfA::PT3 fimbrin proteins were efficiently assembled into recombinant fimbrial fibers present at the cell surface of *S. enteritidis* and proved that their attachment to the cell surface was relatively stable. These results are further summarized in Table 3.

TABLE 3

Properties of *S. enteritidis* strains containing recombinant agfA.

| | Protein Size | (kDa) | T Plates | | T Broth |
|---|---|---|---|---|---|
| Strain | Predicted | Experimental | +FA | Fibers | Fibers |
| 3b | 13.4 | 17 | +++ | +++ | +++ |
| 2–2a | | >60 | ++ | – | – |
| A1 | 13.6 | 17.5 | + | +/– | – |
| A2 | 13.7 | 17 | +++ | ++ | ++ |
| A3 | 13.7 | 17 | ++ | ++ | ++ |
| A4 | 13.6 | 17 | +++ | ++ | ++ |
| A5 | 13.8 | 14.5 | +++ | ++ | ++ |
| A6 | 13.5 | 15.5 | ++ | ++ | + |
| A7 | 13.7 | 17 | ++ | + | + |
| A8 | 13.5 | 15.5 | ++ | ++ | ++ |
| A9 | 13.6 | 14.5 | ++ | ++ | ++ |
| A10 | 13.4 | 17 | – | +/– | +/– |
| A+ | 13.4 | 17 | +++ | +++ | +++ |

Resistance of the Recombinant TAF Fibers to Proteinase K Digestion

Although the recombinant fimbrial fibers looked similar to $W^+$ TAF, it further analysis was conducted to determine if they retained some of their stable properties. Western blot analysis of the *S. enteritidis* strains A1–A10 after proteinase K digestion for 1 or 2 hr is represented in FIGS. 5A and 5B. Most of the chimeric fimbrial fibers were resistant to proteinase K, with all strains except A6, A9, and A 10 (FIG. 5, lanes 10, 13, and 14) displaying immunoreactive protein bands after 2 hr of digestion. The immunoreactive band observed for strain A1 (FIG. 5, lane 3) suggested that this strain might also possess a small number of polymerized chimeric fimbrial fibers even though they were not consistently present at the cell surface when viewed by EM. As expected, AgfA from *S. enteritidis* 3b or the $A^+$ control strain remained intact (FIG. 5, lanes 8 and 15), the dimer demonstrating the two domain structure of AgfA [Collinson, 1999]. Multiple immunoreactive bands were observed for strains A4, A5, A7 (FIG. 5, lanes 6, 7, and 11 ). These results indicated that most of the chimeric fimbrial fibers produced in *S. enteritidis* possessed a stable, ordered superstructure that was protease resistant, very similar to $W^+$ or mature thin aggregative fimbriae.

REFERENCES CITED IN THE FOREGOING DESCRIPTION

Aizawa, S-I, et al. (1990). *J. Mol. Biol.,* 211:673–677.

Ausubel, ea (1987). *Current protocols in molecular biology*, Greene Publishing Associates and Wiley-Intersciences.

Bakker, D., et al. (1990). *Microb, Pathog.,* 8:343–352.

Bian, Z. and S. Normark (1997). EMBO *Journal,* 16: 5827–5836.

Cattozzo, E. M., et al. (1997). *J. Biotech.,* 56:191–203.

Caulcott, C. A., et al. (1987). *J. Gen. Microbiol.,* 133:1881–1889.

Cohen, F. C., et al. (1994). *Science,* 264:530–531.

Collinson, S. K., et al. (1996). *J. Bacteriol.,* 178:662–667.

Collinson, S. K., et al. (1993). *J. Bacteriol.,* 175:12–18.

Collinson, S. K., et al. (1991). *J. Bacteriol.,* 173:4773–4781.

Collinson, S. K., et al. (1992). *J. Bacteriol.,* 174:4490–4495.

Collinson, S. K., et al. (1999). *J. Mol. Biol., accepted.*

Curtiss III, R., et al. (1994). *Dev. Biol. Stand.,* 82:23–33.

Der Vartanian, M. et al. (1997). *Vaccine,* 15:111–120.

Doran, J. L., et al. (1993). *J. Clin. Microbiol.,* 31:2263–2273.

Edwards, R. A., et al. (1998). *Gene,* 207:149–157

Fields, P. A., et al. (1986). *Proc. Natl. Acad. Sci. U.S.A.,* 83:5189–5193

Flynn, J. L., et al. (1990). *Mol. Microbiol.,* 4:2111–2118.

Galán, J. E. (1996). *Mol. Micro.,* 20:263–271.

Hackett, J. (1993). *Curr. Opin Biotech.,* 4:611–615.

Hamilton, C. M., et al. (1989). *J. Bacteriol.,* 171:4617–4622.

Hammar, M., et al. (1995). *Molecular Microbiology,* 18:661–670.

Hammar, M., et al. (1996). *Proc. Natl. Acad. Sci. USA,* 93:6562–6566.

Hashimoto-Gotoh, T., et al. (1981). *Gene,* 16:227–235.

Hedegaard, L. and P. Klemm (1989). *Gene,* 85:115–124.

Hone, D., et al. (1988) *Microb. Pathog.,* 5:407–418.

Horton, R. M., et al. (1989). *Gene,* 77:61–68.

Hultgren, S. J., et al. (1993). *Cell,* 73:897–901.

Hultgren, S. J., et al. (1196). *Bacterial adhesins and their assembly. Escherichia coli* and *Salmonella*, American Society for Microbiology.

Ingmer, H. and S. N. Cohen (1993). *J. Bacteriol.,* 175:6046–6048.

Innis, ea (1990).

Jardim, A., et al. (1990). *J. Exp. Med.,* 172:645–648.

Jardim, A. J. (1994). Immunological and biochemical characterization of the major surface membrane proteins gp63 and the lipophosphoglycan associated protein of *Leishmania*, University of Victoria.

Jennings, P. A., et al. (1989). *Protein Engineering,* 2:365–369.

Kuby, J. (1'994). *Immunology*, W. H. Freeman and Company.

Levi, R. and R. Arnon (1996). *Vaccine,* 14:85–92.

Levine, M. M., et al. (1996). *J. Biotech.,* 44:193–196.

Link, A. J., et al. (1997). *J. Bacteriol.,* 179:6228–6237.

Loferer, H., et al. (1997). *Molecular Microbiology,* 26:11–23.

Low, D., et al. (1996). *Fimbraie. Escherichia coli and Salmonella*, American Society for Microbiology.

Manen, D., et al. (1990). *Mol. Microbiol.* 4:1839–1846.

McSorley, S. J., et al. (1997). *Infect. Immun.,* 65:171–178.

Meacock, P. A. and S. N. Cohen (1980). *Cell,* 20:529–542.

Miller, C. A., et al. (1990). *Cell,* 62:127–133.

Mol. O. and B. Oudega (1996). *FEMS Microbiol Rev.,* 19:25–52.

Newton, S. M. C., et al. (1989). *Science,* 244:70–72.

Newton, S. M. C., et al. (1995). *Res. Microbiol.,* 146:203–216.

Newton, S. M. C., et al., (1991). *Infect. Immun.,* 59:2158–2165.

Olsén, Al., et al. (1993). *Molecular Microbiology,* 7:523–536.

Pallesen. L. and P. Klemm (1994). *Chimeric fimbrial vaccines. Fimbriae. Adhesion, Genetics, Biogenesis and Vaccines*, CRC Press.

Römling, U., et al. (1998a). *Journal of Bacteriology,* 180:722–731.

Römling, U., et al. (1998b). *Mol. Microbiol.,* 28:249–264.

Salmond, G. P. C. (1996). *Trends in Microbiology,* 4:474–476.

Sambrook, J., et al. (1989). *Molecular Cloning: A Laboratory Manual*, Cold Spring Harbor Laboratory.

Spitzer, N., et al. (1998). *Vaccine:* In press.

Stentebjerg-Olesen, B., et al. (1997). *Microbiology,* 143:2027–2038.

Strugnell, R. A., et al. (1990). *Gene,* 88:57–63.

Thanassi, D. G., et al. (1998). *Proc. Natl. Acad. Sci. U.S.A.,* 95:3146–3151.

Thiry, G., et al. (1989). *App. Env. Microbiol.,* 55:984–993.

Van der Zee, A., et al. (1995). *Vaccine,* 13:753–758.

van Die, I., et al. (1990). *Mol. Gen. Genet.,* 222:297–303.

Vanegas, R. A., et al. (1997). *Vaccine,* 15:321–324.

Verma, N. K., et al. (1995a). *Vaccine,* 13:235–244.

Verma, N K., et al. (1995b). *Vaccine,* 13:142–150.

Wahle, E. and A. Kornberg (1988). *EMBO J.,* 1:1889–1895.

Wu, J. Y., et al. (1989). *Proc. Natl. Acad. Sci. U.S.A.,* 86:4726–4730.

EXAMPLE 1

Structural Predictions of AgfA, the Insoluble Fimbrial Subunit of *Salmonella* Thin Aggregative Fimbriae The unusually stable and multifunctional, thin aggregative fimbriae common to all *Salmonella* spp. are principally polymers of the fimbrin subunit, AgfA. AgfA of *Salmonella enteritidis* consisted of two domains: a protease-sensitive, 22 amino acid N-terminal region and a protease-resistant, 109 residue C-terminal core. The unusual amino acid sequence of the AgfA core region comprised 2-, 5- and 10-fold internal sequence homology patterns reflected in 5 conserved, 18-residue tandem repeats. These repeats had the consensus sequence, $Sx_5QxGx_2NxAx_3Q$ (SEQ ID NO: 59) and were linked together by 4 or 5 residues, (x)xAx2. The predicted secondary structure for this unusual arrangement of tandem repeats in AgfA indicated mainly extended conformation with the β-strands linked by 4 to 6 residues. Candidate proteins containing motifs of alternating β-strands and short loops were selected from folds described in SCOP as a source of coordinates for AgfA model construction. Three all-β class motifs selected from the *Serratia marcescens* metalloprotease, myelin P2 protein or vitelline membrane outer protein I were used for initial AgfA homology build-up procedures ultimately resulting in three structural models, β barrel, β prism and parallel β helix. The β barrel model suggested a compact, albeit irregular structure, with the β-strands arranged in two antiparallel β-sheet faces. The β prism model did not reflect the five- or ten-fold symmetry of the AgfA primary sequence. The favored, parallel β helix models was a compact coil of ten helically arranged β-strands forming two parallel β-sheet faces. This arrangement predicted a regular, potentially stable, C-terminal core region consistent with the observed tandem repeat sequences, protease-resistance and strong tendency of this fimbrin to oligomerize and aggregate. Positional conservation of amino acid residues in AgfA and the *E. coli* AgfA homologue, CsgA, provided strong evolutionary support for this model. The parallel β helix model of AgfA offers an interesting solution to a multifunctional fimbrin molecular surface having solvent exposed areas, regions for major and minor subunit interactions as well as fiber-fiber interactions common to many bacterial fimbriae.

Fimbriae and pili are terms, often used interchangeably, for fine, hairlike structures that protrude from the surface of many bacteria (Firth et al., 1996; Low et al., 1996; Mol & Oudega, 1996; Tennent & Mattick, 1994). These ubiquitous fibres have received considerable attention mainly due to their pivotal role in facilitating bacterial adherence in diverse circumstances including host tissue colonization (Gaastra & de Graaf, 1982; Low et al., 1996; Tennent & Mattick, 1994), bacterial cell-cell interactions (Marceau et al., 1995; Whittaker et al., 1996), conjugal transfer of DNA including exchange of antibiotic resistance genes (Firth et al., 1996; Silverman, 1997) or transfer of genetic information into susceptible hosts (Fullner et al., 1996; Lai & Kado, 1998). Many diverse fimbrial and pili systems have been studied in detail to understand the molecular basis for fiber function, assembly and regulation. This information has furthered the understanding of fundamental physiological phenomena including protein processing, transport and organelle assembly (de Graaf & Bakker, 1992; Firth et al., 1996; Hung et al., 1996, Kuehn, 1994; Leathart & Gally, 1998; Low et al., 1996; Mol & Oudega, 1996; Smyth et al., 1996; Strom & Lory, 1993). In addition, these studies have furnished biotechnological advances in disease detection and prevention in the form of fimbrial-based diagnostics and therapeutics, fimbrial vaccine formulations and passive immunization methodologies (Abraham et al., 1985; Der Vartanian et al., 1994; Doran et al., 1993; Levine et al., 1994; Ogawa et al., 1997; Pallesen & Klemm, 1994; Thorns et al., 1994).

Fimbriae are complex polymers, 2 to 9 nm wide and several hundred or thousand nm long. Structurally, they are comprised mainly of a single fimbrin (or pilin) protein subunit type polymerized to form the bulk of the fiber (Low et al., 1996; Paranchych, 1990; Silverman, 1997; Tennent & Mattick, 1994). Additional constituents have been identified in many fimbriae (Low et al., 1996). These include minor fimbrin-like proteins required for the fidelity of fiber biogenesis (de Graaf & Bakker, 1992; Klemm & Krogfelt, 1994; Kuehn et al., 1994) and/or specialized adhesin subunits required for specific receptor recognition (Low et al., 1996). In other cases, as with K88 fimbriae, receptor binding specificity is an apparent function of the major fimbrin subunit itself (de Graaf & Bakker, 1992).

Low resolution X-ray and optical diffraction studies of laterally aggregated or paracrystalline arrangements of thin (2 to 5 nm) and thick (7 to 9 nm) fimbriae indicate that, in both fiber types, the major fimbrin subunits are helically arranged within the fiber (Brinton Jr, 1965; Gong & Makowski, 1992; Heck et al., 1996; Paranchych, 1990; Silverman, 1997; Simons et al., 1994). High resolution, freeze fracture electron microscopy studies of native and mutant *E. coli* Pap pili ultrastructure revealed that this 7 nm pili polymer terminates with a thin, 2 nm wide, fibril of open helically arranged minor subunits that display the terminal adhesin subunit required for specific binding of the fiber to its respective target receptor (Klemm & Krogfelt, 1994; Kuehn et al., 1992). This complex architecture is shared by other thick fimbriae of *E. coli* including type I, S and *Haemophilus* pili (Hung et al., 1996; Jones et al., 1997; St. Geme III et al., 1996). In addition, the structural plasticity of fimbriae is evident after certain chemical treatments that "unravel" thick fimbriae into thin fibrils or "wind" thin fibres into thicker structures (Mol & Oudega, 1996). However, the ultrastructure of thin fimbriae is largely unknown.

The *Neisseria gonorrhoea* Type IV pilin subunit is the sole fimbrin to date to be crystalized and for which a 3-D structure has been determined (Parge et al., 1995). This novel α-β roll pilin structure was modeled into a helically polymerized 7 nm fiber based upon the steric considerations and physicochemical surface characteristics of the pilin subunits (Parge et al., 1995). Otherwise, no tertiary structural information is available for other fimbrins. The pronounced tendency of unassembled or depolymerized fimbrin monomers to aggregate or repolymerize complicates crystal formation and consequently precludes 3-D structural elucidation.

The present Example relates to the structural elucidation of thin aggregative fimbriae of *Salmonella*. Thin aggregative fimbriae are one, of at least 8 fimbrial types produced by various strains of these important animal pathogens (Bäumler & Heffron, 1995; Doran et al., 1993; Low et al., 1996). The exact role(s) of thin aggregative fimbriae (3–4 nm) in *Salmonella* pathogenesis is as yet uncertain (Sukupolvi et al., 1997a), even though these fibres have been shown to bind various host proteins (Collinson et al., 1993; Sjöbring et al., 1994) and promote interaction of *Salmonella* with mouse small intestinal epithelial cells (Sukupolvi et al., 1997b). Given the extreme stability and unusually aggregative nature of these fibres, their importance to *Salmonella* pathogenesis may also be related to their role in promoting *Salmonella* autoaggregation (Collinson et al., 1993; Collinson et al., 1991). This feature has broad implications for host infection (Collinson et al., 1991) and *Salmonella* biofilm formation on inert surfaces (Austin et al., 1998).

Virtually all *Salmonella* spp. tested to date possess the agfA fimbrin gene (Bäumler et al., 1997; Collinson et al., 1996b; Doran et al., 1993). *Escherichia coli* also possess an agfA fimbrin homologue, csgA, that assembles into fibres named curli (Olsén et al., 1993). *Salmonella* thin aggregative fimbriae and *E. coli* curli are biochemically (Collinson et al., 1992; Doran et al., 1993; Olsén et al., 1993), genetically (Collinson et al., 1996a; Römling et al., 1998), and functionally (Austin et al., 1998; Collinson et al., 1993; Collinson et al., 1992; Hammar et al., 1995; Olsén et al., 1993; Vidal et al., 1998) analogous. This is consistent with the fact that both fimbrin genes are highly conserved homologues from an ancient operon in the progenitor of *Salmonella* and *E. coli* (Bäumler et al., 1997).

Thin aggregative fimbriae were purified by an unconventional procedure from *Salmonella enteritidis* (Collinson et al., 1991). In addition, brief exposure of the fimbriae to 90% formic acid (Collinson et al., 1991) is the only pretreatment known to depolymerize these fibres to release the AgfA fimbrin monomers. Since this initial characterization, very little biophysical data have emerged for thin aggregative fimbriae due to their extreme aggregative nature and the existence of multiple isoforms (Collinson et al., 1991). However, such information is needed to understand the molecular basis for the aggregative nature and unusual stability of these fibres as well as to provide the molecular framework for the design of AgfA-based heterologous *Salmonella* vaccines (White et al., 1999).

As a novel approach to explore AgfA tertiary structure, homology buildup and molecular modeling techniques were applied to the prediction of AgfA tertiary structure taking into account the intriguing primary amino acid sequence repeat motif in AgfA and the discovery of the protease resistant AgfA C-terminal core region. As the first modeling study of any bacterial fimbrin or pilin tertiary structure, the initial goal was to obtain a working model of AgfA molecular structure for future experimental design and testing.

Materials and Methods

Purification and Depolymerization of Thin Aggregative Fimbriae, SEF17

Thin aggregative fimbriae were isolated and purified from *Salmonella enteritidis* 27655-3b grown on solid T medium as previously described (Collinson et al., 1991). Purified fimbriae samples were routinely treated with 90% formic acid to depolymerize the AgfA fimbrin subunits prior to electrophoretic or immunoblot analysis (Collinson et al., 1993; Collinson et al., 1991).

The effect of formic acid concentration on disaggregation and depolymerization of thin aggregative fimbriae was determined on fimbrial suspensions of 0.5 mg/ml. The large clumps of fimbriae were broken using a 2 ml Micro Tissue Grinder (VWR Canlab). Homogenized suspensions of fimbriae were aliquoted into microfuge tubes and the fimbriae recovered by centrifugation (15,600×g, 10 min) before being resuspended in formic acid solutions and recording the absorbance at 600 nm ($A_{600}$). A subsample of each finbrial suspension containing approximately 20 μg of protein was lyophilized and subjected to electrophoresis and immunoblot analysis.

SDS-PAGE and Immunoblot Analysis

SDS-PAGE was performed according to the method of Laemmli (Laemmli, 1970). Immunoblot analysis of AgfA was performed as previously described (Collinson et al., 1993; Collinson et al., 1991) using rabbit polyclonal immune serum generated to purified thin aggregative fimbriae.

N-terminal Amino Acid Analyses

N-terminal amino acid sequence analyses were performed as previously described (Collinson et al., 1991).

Protease Treatment of Thin Aggregative Fimbriae

Whole *S. enteritidis* 3b cells possessing thin aggregative fimbriae or purified thin aggregative fimbriae were resuspended in Laemmli sample buffer (Laemmli, 1970), boiled for 10 min, cooled and then brought to a final concentration of 0.5 mg/ml proteinase K before incubation for 1 hr at 60° C. Samples were boiled, fimbriae recovered by centrifugation (15,600×g, 10 min), depolymerized with 90% formic acid (Collinson et al., 1991) and then analysed by SDS-PAGE or immunoblotting for products of digestion.

Secondary Structural Analysis of AgfA

Secondary structure analysis of AgfA was determined using several programs including: Alexis version 1.2 SEQSEE 10 (Wishart et al., 1994), PPSP (Parker & Hodges, 1991a; Parker & Hodges, 1991b), Sequences Annotated by Structure (biochem.ucl.ac.uk/cgi-bin/sas), Gibrat Secondary Structure Prediction and Hierarchical Neural Network (pbil.ibcp.fr/NPSA,NNPredict, (cmcmpharm.ucsf.edu/cgi-bin/nnpredict.pl), PhDsec (embl-heidelberg.de/predictprotein) and Predator (embl-heidelberg.de/predator).

Homology Alignment and Selection of Proteins for Homology Buildup

The AgfA amino acid sequence was compared to sequences of proteins with known tertiary structures defined by analysis of X-ray crystallography using SEQSEE (Wishart et al., 1994), HomologyPlot (Parker & Hodges, 1991b) and PropSearch (Hobohm & Sanders, 1995). Several candidate proteins for structural alignment were chosen by scanning protein folds described in the Protein Data Bank (PDB) (Bernstein et al., 1977) and the program SCOP (Murzin et al., 1995) to identify several proteins containing β-strand structures connected by short loops. Two proteins, the *Serratia marcescens* protease (SMP) (Baumann et al., 1995) and the C-terminal region of the bovine myelin P2 protein (PMP) (Cowan et al., 1993; Jones et al., 1988), contained a repeating pattern of hydrophobic residues analagous to that proposed for AgfA. SMP and PMP were chosen as templates for the β barrel and parallel β helix models, respectively (FIGS. 16*a, b*). The β prism fold of the vitelline membrane outer layer protein I (VMO-I) (Shimizu & Morikawa, 1996; Shimizu et al, 1994) was chosen as a third structural template on the basis of the VMO-I primary sequence alignment with that of AgfA (FIG. 16*c*).

AgfA Parallel β-helix Model Homology Buildup Procedure

The parallel β-helix structure of AgfA was built using Insight II and Discover programs (BioSym Technologies Inc.). Initially, the a-carbon distance restraints of amino acid residues 327 to 343 of the known x-ray structure for SMP (Baumann, 1994; Braunagel & Benedik, 1990) were used to build the first β-turn-β structure corresponding to amino acid residues 23 to 39 of AgfA (FIG. 16*a*). Amino acid residues in SMP were replaced with those corresponding to the AgfA sequence and the AgfA structure was built manually to residue 52. The resulting 30-residue AgfA template, which no longer resembled the SMP structure due to differing loop sizes and longer β-strands, was used repeatedly with dynamics simulations to build successive levels of the AgfA structure. The completed agfA structure was then minimized using various distance restraints, manual changes in sidechain and backbone torsion angles with regular checks on the chiral status of the backbone configurations. Distance restraints were gradually removed until a low energy structure of 80 kCal was obtained using only Ca restraints. Unfavorable angles and distances were removed using molecular dynamics (MD) simulations of 1 ps with a full set of distance restraints. The optimized structure was then subjected to 50 ps of MD simulations with no constraints to further reduce the energy of the structure. The distance restraints used were briefly tested by simulated annealing. Further improvements to the model were accomplished by generating a distance and dihedral restraint file using the average Ca to Ca distances observed in the respective predicted structure and the x-ray structure used to the model. The preliminary dihedral restraint for the angle f and y was set for an extended structure. The structure was minimized with and without their respective restraint files. The dynamics procedure was used to further improve the f and y angles.

AgfA β-barrel Model Homology Buildup

The β-barrel structure of AgfA was built up by homlogy modeling using coordinates of the ten β-strand β-barrel of PMP as the inital template. Residues 40 to 86, comprising the first 5 β-strands of PMP, were the most homologous with residues 25 to 72 of AgfA (FIG. 16*b*). This PMP sequence was converted to the correct AgfA sequence to build the first AgfA region. This first region was then duplicated and the N-terminal residues L25 to I27 of AgfA were overlapped with C-terminal residues I70 to L72 to form the template for the second set of 5 β-strands. The amino acids in this second region were then changed to correspond to the later half of the actual AgfA sequence. Visual inspection removed several obvious side chain contacts before the model was subjected to Steepest descent and conjugate gradient minimization.

AgfA β Prism Model Homology Buildup

The β prism AgfA structure was built based upon alignment of AgfA sequence with VMO-I taking into account three core loops and conserved nonpolar-polar-nonpolar motifs at the N-terminal region of the AgfA core and conserved VMO-I D and E residues that are N and Q in AgfA (FIG. 16*c*). The first of three interal repeats was mutated form VMOI sequence to AgfA using options in InSightII (Biosym). Occasionally, side chains were moved manually when unfavorable interactions were encountered. The model was subjected to conjujate gradient minimization with the $C_a$ carbons fixed.

Statistical Evaluation of Models

The VADAR (Wishart et al., 1995) and PROCHECK (Morris et al., 1992) statistical analysis programs were used to evaluate the models at several stages during the buildup procedure as an indication of improvement in successive models. Statistics and energy minima of the three prototype AgfA fimbrin model structures are presented in Table 4.

TABLE 4

Summary of Procheck and VADAR statistics for the AgfA model structures

| | AgfA Model Structure | | |
|---|---|---|---|
| Statistic Parameter | parallel β helix | β barrel | β prism |
| Template protein[a] | SMP | PMP | VMO-I |
| Free energy (kCal) | −64 | −49 | −40 |

TABLE 4-continued

Summary of Procheck and VADAR statistics for the AgfA model structures

| | AgfA Model Structure | | |
|---|---|---|---|
| Statistic Parameter | parallel β helix | β barrel | β prism |
| Total energy (kCal) | −240 | | |
| f/y core[b] | 68% | 63% | 56% |
| Total accessible surface area (Å$^2$) | 5524 | 5848 | 7625 |
| Total volume packing (Å$^3$) | 12875 | 12783 | 12500 |
| % β-strand predicted | 93 | 71 | 40 |

[a]SMP, *Serrati marcescens* protease (Baumann et al., 1995); PMP, bovine myelin P2 protein (Cowan et al., 1993; Jones et al., 1988); VMO-I, vitelline membrane outer layer protein I (Shimizu & Morikawa, 1996; Shimizu et al., 1994).
[b]f/y core calculated using Procheck ™ (Morris et al., 1992) and VADAR (Wishart et al., 1995).

Results

Two-domain Character of AgfA Fimbrin

Figure 7:
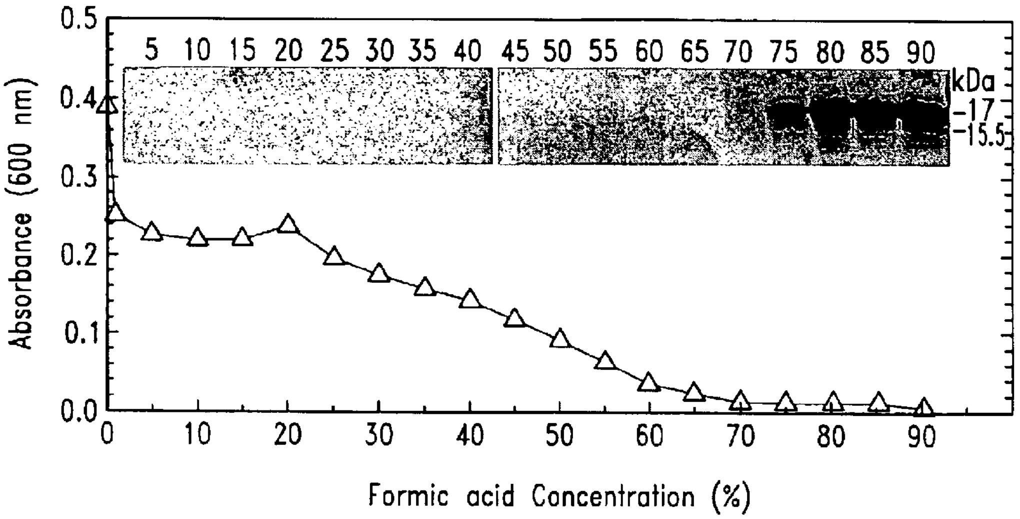
FIG. 7. The effect of formic acid concentration on the absorbance at 600 nm of 0.5 mg/ml suspensions thin aggregative fimbriae. Inset: Immunoblot of 20 $\mu$g of thin aggregative fimbriae treated in one of several formic acid solutions noted above each lane and detected on immunoblots with fimbrin-specific immune serum as described in the Materials and Methods. The size of each protein is noted in kDa to the right of the blot.
Figure 8:
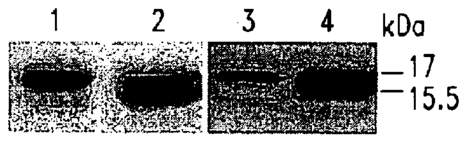
FIG. 8. Immunoblot analysis of *S. enteritidis* native thin aggregative fimbriae (lanes 1 and 2) or purified fimbriae (lanes 3 and 4). Samples were untreated (lanes 1 and 3) or treated (lanes 2 and 4) with proteinase K before immunoblot analysis as described in the Materials and Methods. The protein band sizes on immunoblots are noted in kDa to the right of the blot.

Treatment of thin aggregative fimbriae with at least 70% formic acid was required to ensure at least partial depolymerization to release the 17,000 Da AgfA fimbrin (FIG. 7). Concomitant with the depolymerization of thin aggregative fimbriae was the release of a 15,500 Da protein (FIG. 7). N-terminal amino acid sequence analysis of the 15,500 Da species indicated that this minor protein was a truncated form of AgfA missing 22 N-terminal amino acids. This fragmentation of AgfA was probably not due to its exposure to concentrated formic acid since prolonged treatment of AgfA with 90% formic acid for up to 3 h at 50° C. does not increase the amount of the 15,500 Da fragment (Collinson et al., 1991). Moreover, AgfA lacks acid cleavable Asp-Pro bonds in the predicted AgfA sequence (Collinson et al., 1996a). However, the first 17 N-terminal amino acids of AgfA could be cleaved from the fimbrin by proteinase K treatment of intact native or purified, thin aggregative fimbriae (FIG. 8, lanes 2 and 4) as confirmed by N-terminal amino acid sequence analysis of the truncated proteins. However, once depolymerized by pretreatment with formic acid, AgfA was completely susceptible to digestion with proteinase K. These results suggested that polymerized AgfA fimbrins possessed two domains, a short, protease-susceptible N-terminal domain of 17 to 22 amino acids and a protease-resistant C-terminal core region comprised of 109 to 114 amino acid residues.

Two-, Five- and Ten-fold Internal Amino Acid Sequence Homology of AgfA

Figure 9A:
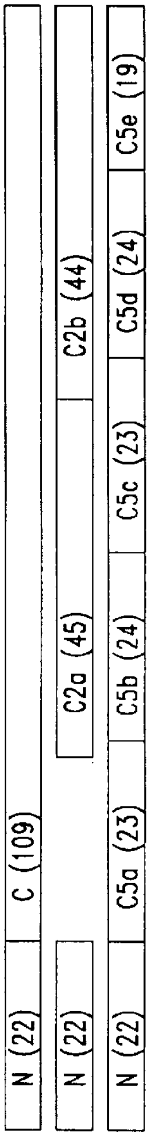
FIG. 9. AgfA fimbrin domains and internal amino acid sequence homology. (a) Schematic diagram of the N-terminal (N) and C-terminal (C) domains of AgfA illustrating the relative positions of the two- or five-fold homologous regions C2a–b or C5a–e, respectively, with in the C-terminus. Values in parenthesis denote the number of amino acids present in each segment. (b) Alignment AgfA (SEQ ID NO: 32) fragments C2a and C2b. Amino acid identity (.) and conservative replacements (underscored) are indicated with gaps (–) introduced for optimal alignments. (c) Alignment of AgfA (SEQ ID NO: 31) fragments C5a to C5e with gaps (–) introduced for optimal alignments. Conserved residues with in each repeat are boxed. (d) The 18 amino acid consensus sequence (SEQ ID NO: 33) of the five internal repeats where x is any amino acid. The position of each residue corresponds to the numbered residues in FIG. 11*c*. (e) Position of the conserved ten nonpolar-polar-nonpolar (ifi) triplet motifs within each of the five 22 or 23 residue repeats. Non-conserved residues of each triplet are boxed.
Figure 9B:
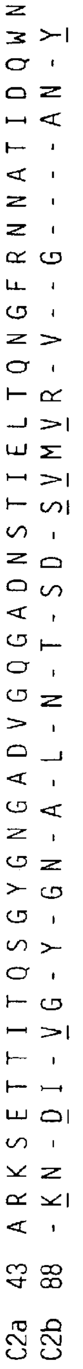

The AgfA primary amino acid sequence possessed features consistent with a two-domain protein. The glycine-rich, N-terminal 22 amino acid sequence was distinguished from the C-terminal core region comprising amino acids 23 to 131 mainly on the basis of a striking two-, five- and ten-fold internal sequence homology within the C-terminus (FIG. 9). A two-fold homology was evident between the segments C2a and C2b that shared 41% amino acid identity or 56% homology if conservative substitutions were considered (FIG. 9*b*).

Figure 9C:
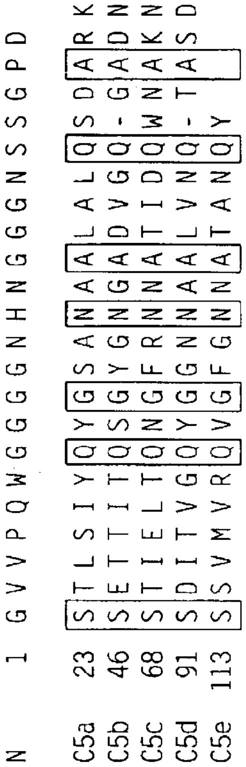

The five-fold sequence homology within the 109 residue C-terminal core region was extremely regular and consisted of five, tandemly arranged segments (FIG. 9*c*). The first 18 amino acids of each of these five segments conformed to the consensus sequence $Sx_5QxGx_2NxAx_3Q$ (SEQ ID NO: 59) separated by 4 or 5 additional residues except for the terminal repeat which ended in Y (FIG. 9*c*). Homology comparisons between segments C5a:C5d and C5c:C5e were the highest with 50% identity compared to segments C5b:C5d or C5d:C5e with 44% residue identity (FIG. 9*a,c*). The other segment pairs were 39% identical.

The ten-fold sequence homology of the AgfA C-terminus was evident as paired hydrophobic regions centered at positions 3 to 5 and 14 to 16 within each consensus motif (FIG. 9*d,e*). Each hydrophobic region possessed three amino acids arranged to conserve a nonpolar-polar-nonpolar (ifi) triplet motif (FIG. 9*e*). Together, these multiple primary sequence patterns were suggestive of highly regular, repeated secondary structure motifs.

Secondary Structure Analysis of AgfA

Several secondary structure prediction programs were used to analyse AgfA secondary structure as described in the Materials and Methods. All of the programs predicted several regions of extended structure separated by short regions of 4 to 10 residues possessing coil conformation (FIG. 10). Frequently, the programs predicted that AgfA residues 34 to 41 adopted a helical structure where as residues 80 to 87 and 103 to 107 were predicted to be helical with less frequency (FIG. 10). No potential membrane spanning sequences were predicted. The ten repeating hydrophobic core regions within AgfA suggested that this protein posessed regular, repeating secondary structural units of 3 to 7 amino acids connected by loops of 4 to 7 residues.

The Protein Data Bank and SCOP were extensively searched to identify protein structures with multiple extended regions separated by coil regions of 4 to 10 residues suitable for model construction as described in the Materials and Methods. Several structures with low homology to AgfA were identified but none of these candidate protein structures contained helical motifs. For this reason, only the extended and coil secondary structures predicted for AgfA were used to predict the tertiary structure of AgfA.

Parallel β-helix Model of AgfA

Figure 11A:
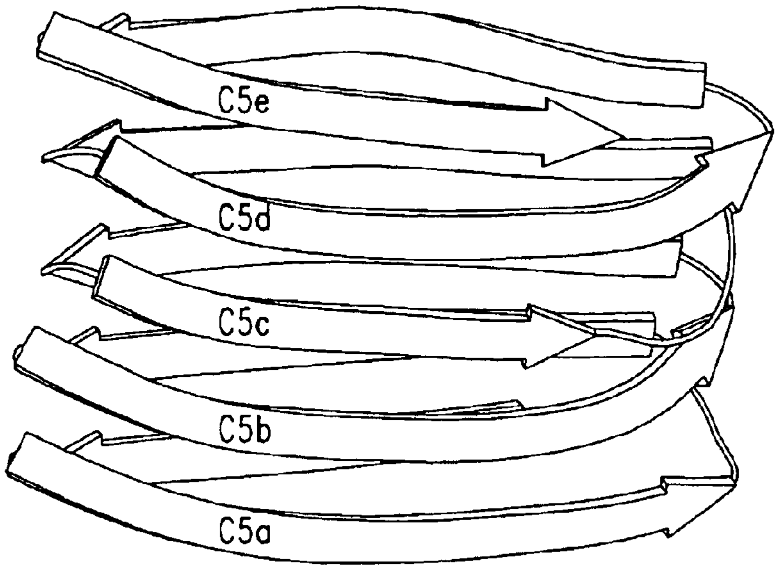
FIG. 11. The proposed parallel β-helix model of AgfA for residues 23 to 130 inclusive. Molescript representation of the five coil helix model viewed form the (a) front side or (b) top. The C-terminal portion of each coil is labeled to identify the respective 22 or 23 amino acid repeat segment as identified in FIGS. 9*a,c*. (c) A wire diagram of the AgfA parallel β helix model viewed as in b but accentuating the vertical alignment of the five consensus segments noted in FIG. 9*c*. The amino acids of each consensus sequence are numbered as indicated in FIG. 9*d*. Carbon atoms (green) are distinguished from nitrogen (blue), oxygen (red) and sulfur (yellow).
Figure 11B:
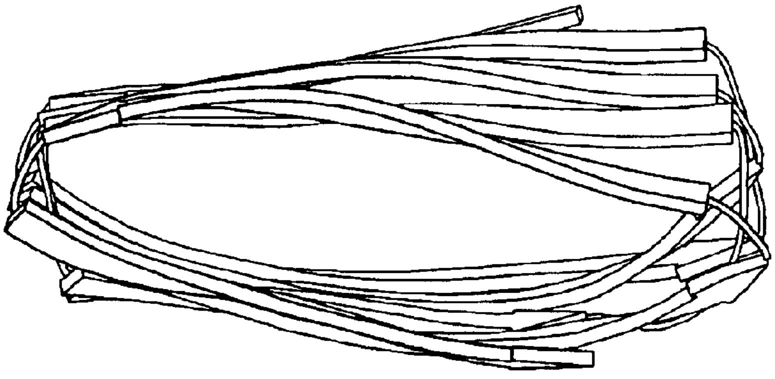
Figure 11C:
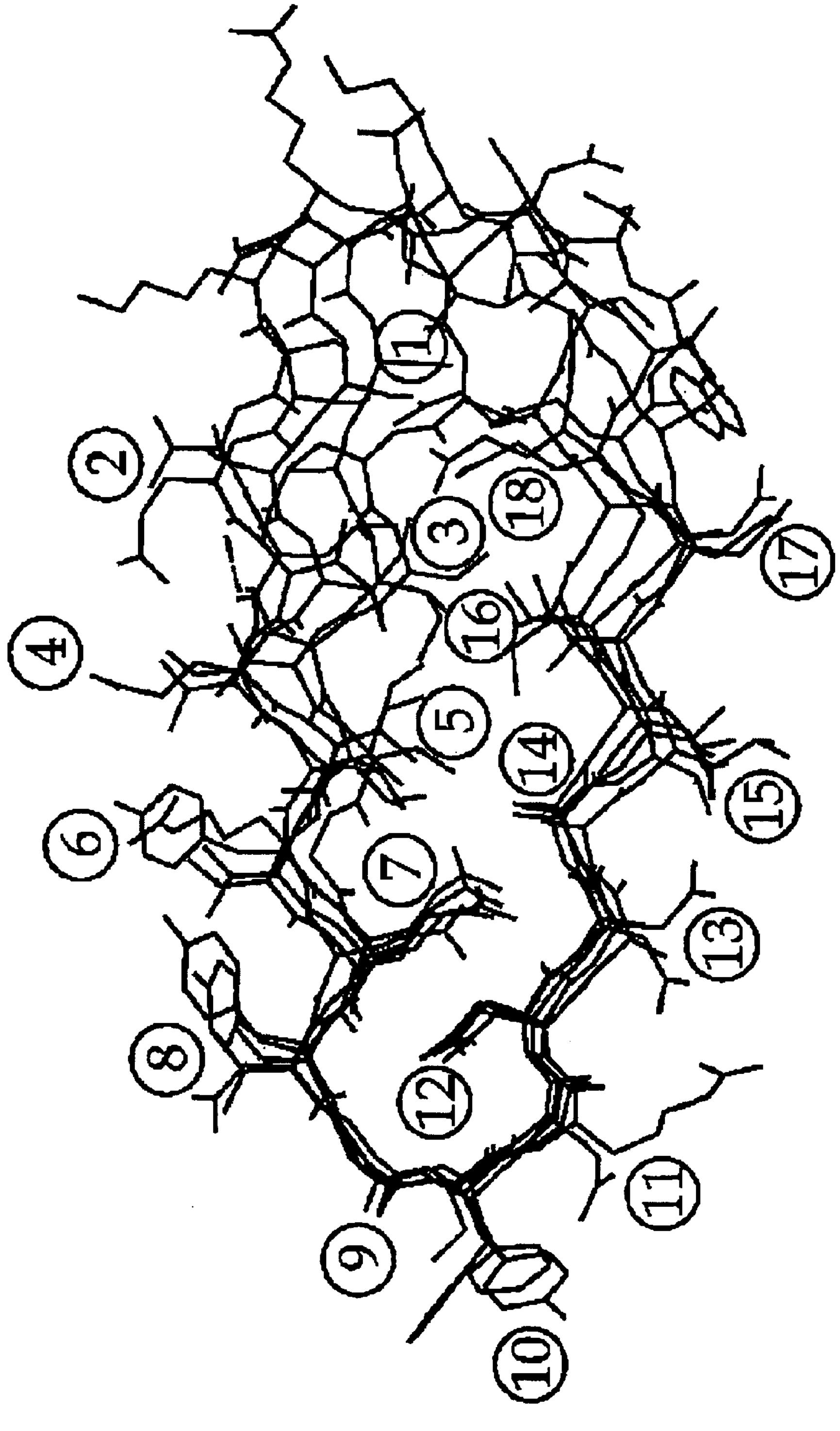

The regular pattern of extended β-strand conformations proposed for AgfA C-terminal region secondary structure was used to select coordinates of candidate template proteins of known tertiary structure suitable for model construction (see Material and Methods). A β-turn-β motif within the β roll structure of the *Serratia marcescens* metalloprotease (SMP) 3-D crystal structure (Baumann et al., 1995) was judged as the best template on which to build the inital turn of the AgfA model structure. Successive layers of AgfA tertiary structure were then built using standard homology modeling techniques (see Materials and Methods). The parallel β helix AgfA tertiary structure model that emerged from this process was a highly regular, compact, right handed, five-coil helix comprised of four coils of 22 or 23 amino acids ending with 18 amino acids of the fifth coil followed by a terminal Y (FIG. 11*a*). This arrangement of vertically stacked, slightly flattened coils created two prominent five-strand parallel β-sheet faces (FIG. 5*a*) oriented into a slightly wedge-shaped, oval molecule (FIG. 11*b*). Each coil consisted of a "β-sandwich" in which the nonpolar residues of the two nonpolar-polar-nonpolar (ifi) β-strand triplets at positions 3 to 5 and 14 to 16 of each 18-residue repeat were internalized forming a tight 4-residue turn ($xGx_2$) centered about the conserved G at position 9 (FIGS. 9*e* & 11*c*). The successive β-sandwiches were joined by a less constrained turn of 4 or 5 residues (FIGS. 9*e* & 11*c*).

Figure 12A:
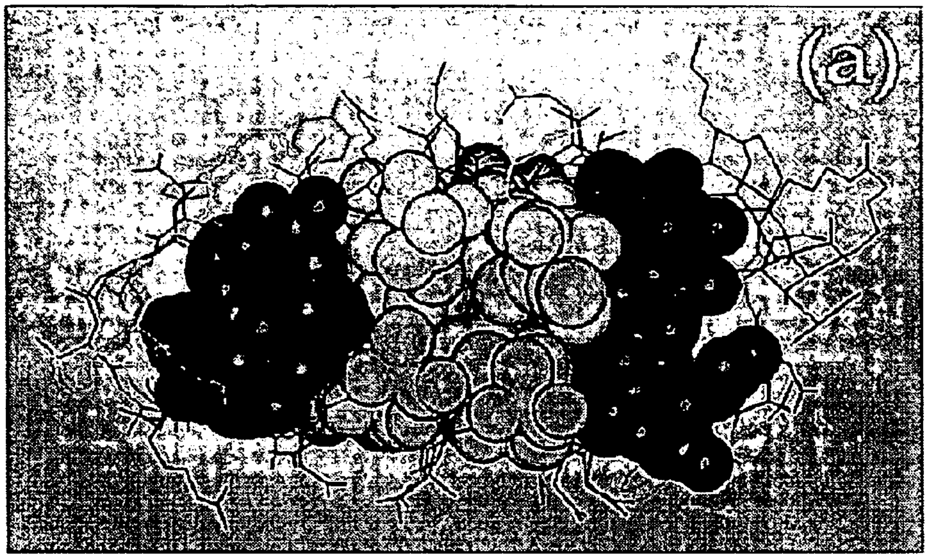
FIG. 12. The proposed parallel β helix model of AgfA viewed as a wire diagram with space filling model representation of (a) internal or (b) surface exposed amino acid side groups viewed from the top as in FIGS. 11*b* & *c*. Space filling model representation of the AgfA β helix model viewed from the (c) front side as in FIGS. 11*a* or (d) back side. Amino acid residues are coloured as; nonpolar (green), polar (red), basic (blue) or W (yellow).
In FIGS. 12*c* and *d* the A, G and internalized residues are grey or white where as other surface exposed residues are coloured.
Figure 12B:
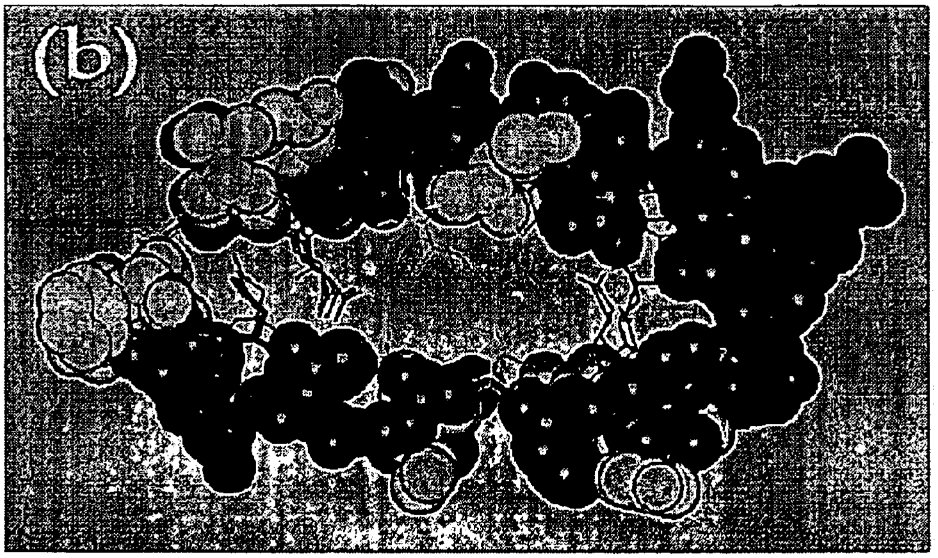

Consequently, the five, vertically stacked β-sandwiches were aligned such that the conserved residues of each consensus sequence were in the same relative position resulting in vertical stacks of like residues in the internal core of the AgfA model structure (FIGS. 11*c*, 12*a* & 12*b*).

Thus, the AgfA parallel β helix model possessed a 19-residue hydrophobic core comprised of nonpolar residues at positions 3, 5, 14 or 16 of the consensus sequence (FIGS. 11*c* & 12*a*). Flanking one side of this non-polar core region were two stacks of five internalized Q and N residues located at positions 7 and 12, respectively, of each consensus sequence (FIGS. 11*c* & 12*a*). These polar amides, Q29,52, 74,97,119 and N34,57,79,102,124, respectively, flanked either side of each successive tight turn such that the $C_9R$ amide sidegroups were hydrogen bonded to the peptide backbone (FIGS. 11*c* & 12*a*). The other side of the hydrophobic core was similarly flanked by two stacks of five polar residues internalized at positions 1 (S23,46,68,91,113) and 18 (Q40,63,85,108,130) of each successive consensus sequence (FIGS. 11*c* & 12*a*).

Figure 12C:
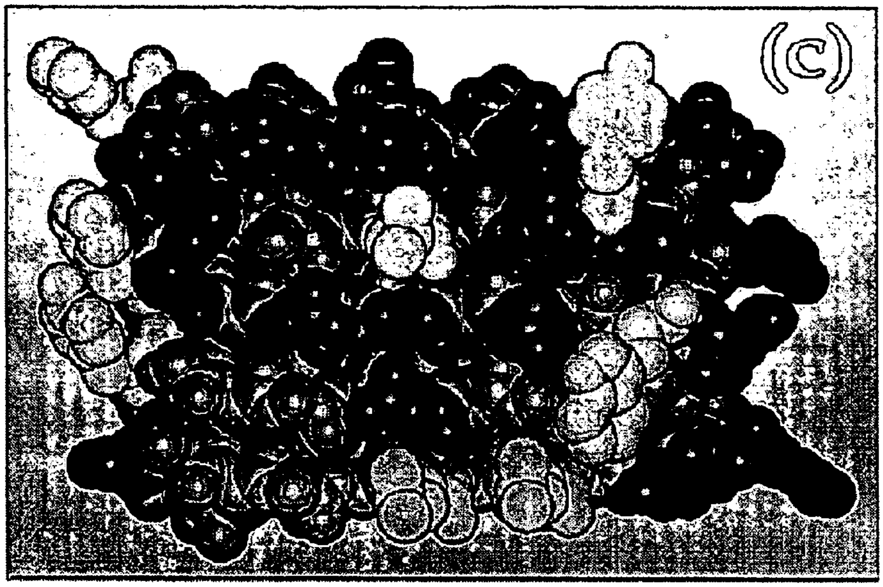
Figure 12D:
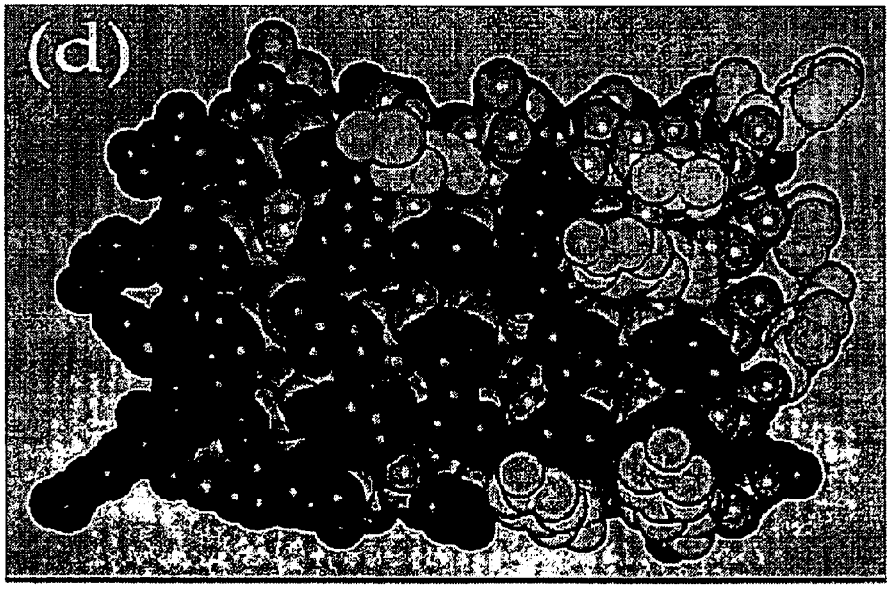

A second consequence of the helical arrangement of successive β sandwiches was the clustering of chemically similar residues on the surface of the proposed AgfA model. Hydrophobic patches were present on this AgfA model on the frontside (W86, L37, L39, L105) (FIG. 12*c*, green and yellow) and end (Y28, Y30, Y98, F77, F122, V120) (FIG. 12*d*, green) of the molecule. Otherwise, the proposed AgfA surface was mainly comprised of polar or charged residues (FIGS. 12*b,c,d*, red). The acidic residues E47,71 and D42, 60,66,84,92,112 (FIGS. 12*c,d,* red) were predicted to be exposed on the end of the molecule opposite to the hydrophobic cluster of Y and F residues (FIG. 12*d*, green) such that they out numbered the basic amino acids (FIG. 1, blue) 8 to 3. The back face of the AgfA model comprised mainly exposed polar amino acids (FIG. 12*d*, red). Several residues with exposed hydroxyl groups were present including S26, 114; T24,49,51,69,73,94 and Y28,30,98 (FIG. 12*d*, red). This compact, highly regular parallel β-helix model of AgfA was consistent with the repeating primary amino acid sequence and predicted secondary structure of repeated β-strand conformations.

β-barrel and β-prism Models of AgfA

In an effort to determine whether the AgfA parallel β-helix structure was a reasonable model, the AgfA primary sequence was also modeled on two other proteins of known structure, also selected for possessing motifs arranged in a series of extended β-strands.

Figure 13A:
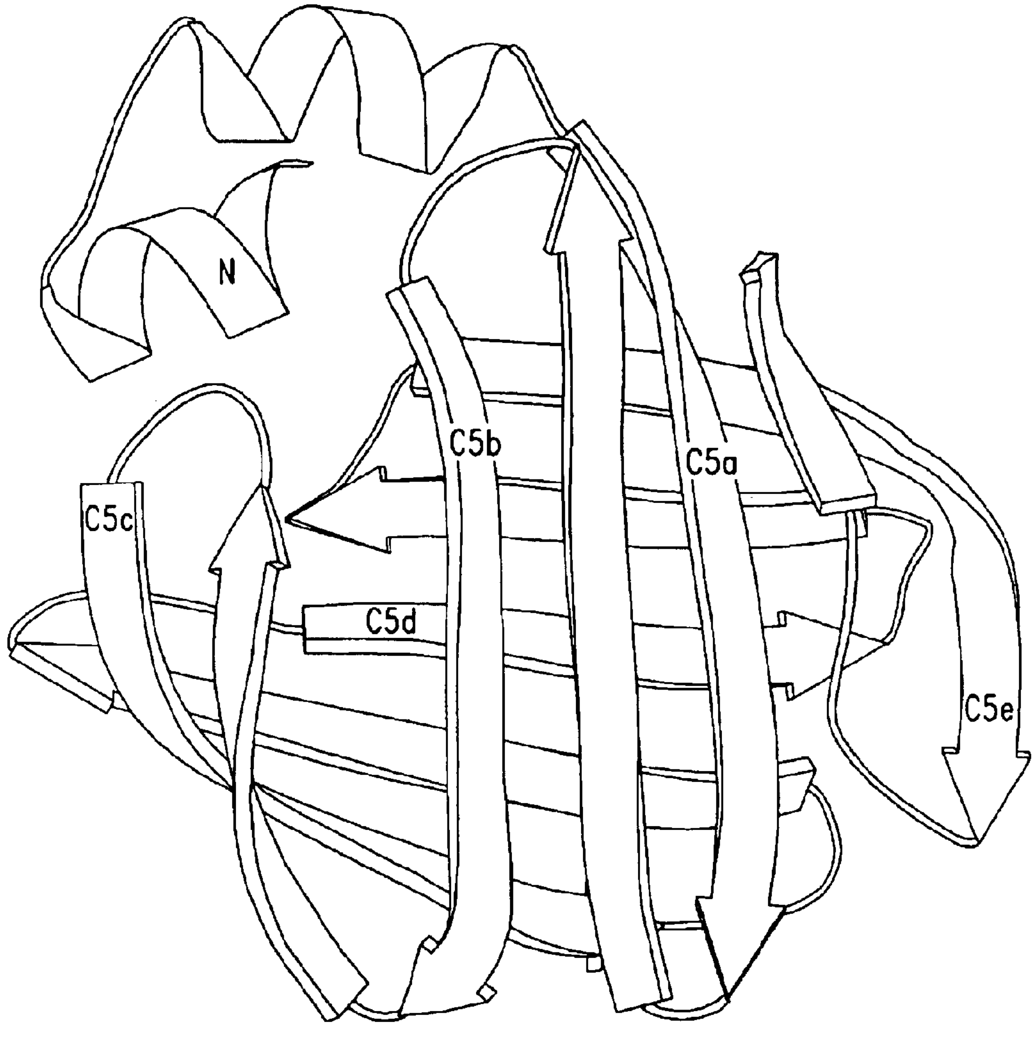
FIG. 13. (a) Molescript representation of the β barrel model of AgfA. The N-terminus (N) and C-terminal repeat segments (C5a to e) are numbered as in FIGS. 9*a,c*. (b) Molescript representation of PMP protein using coordinates obtained from SCOP on which the AgfA β barrel model was modeled as described in the Materials and Methods.
Figure 13B:
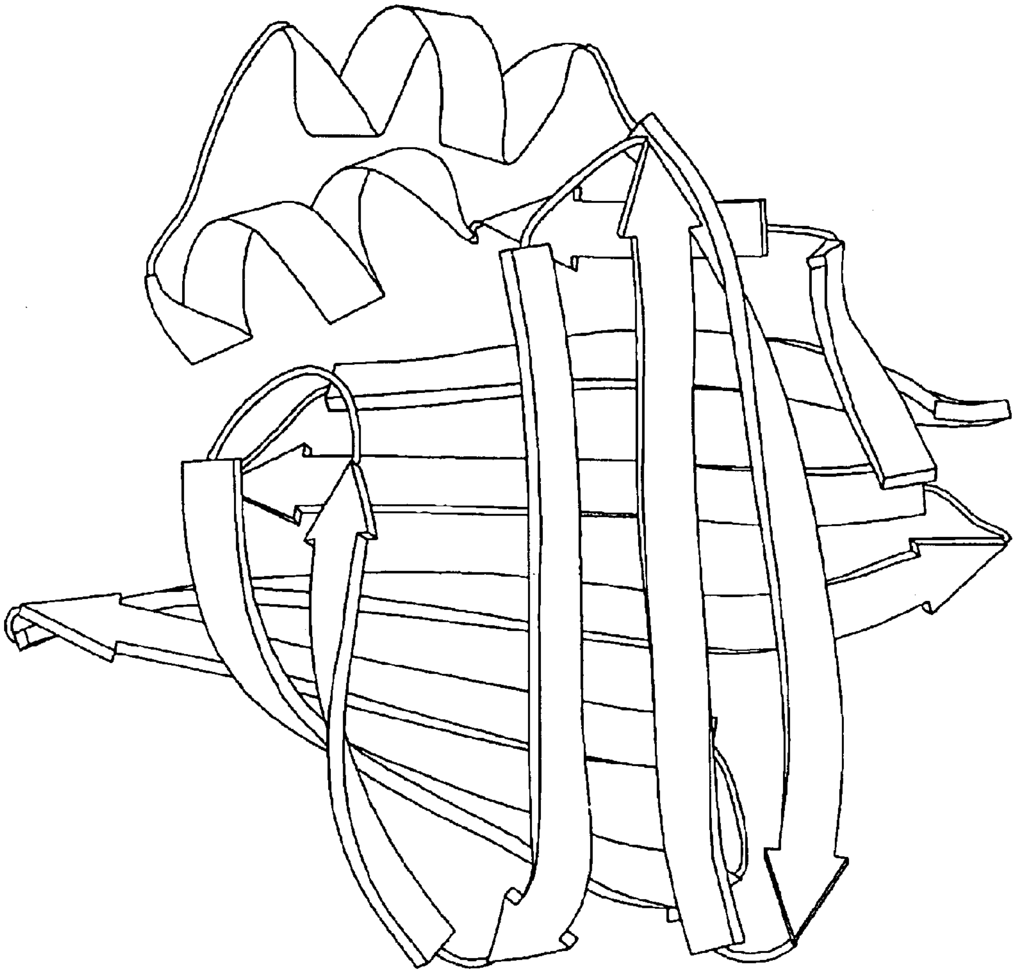

The AgfA β-barrel model (FIG. 13*a*) was built using the coordinates of the ten-stranded β-barrel structure of bovine myelin P2 protein (PMP) 3-D crystal structure (Cowan et al., 1993; Jones et al., 1988) as the template (FIG. 13*b*) as described in the Material and Methods. In this AgfA prototype model, each of the five consensus repeat motifs were folded about the central $QxGx_2N$ sequence such that the predicted β-strands were bonded in antiparallel fashion (FIG. 13*a*). Segments C5a, C5b and the C-terminal half of C5e formed one antiparallel β-sheet face of the barrel where as the other face was formed by C5c, C5d and the N-terminal half of C5e (FIGS. 9*a* & 13*a*). Several key features of the AgfA β-barrel model included: a hydrophobic core region comprised mainly of internalized nonpolar residues of the ten nonpolar-polar-nonpolar (ifi) triplets; surface exposure of the aromatic residues Y28,30,55 and F77, 122 at the same end of the molecule; basic residues R44 and K45,89 clustered at one end of the molecule on the protruding loop between segments C5a and C5b and a general lack of clustering of acidic and hydroxyl-containing residues.

Figure 14A:
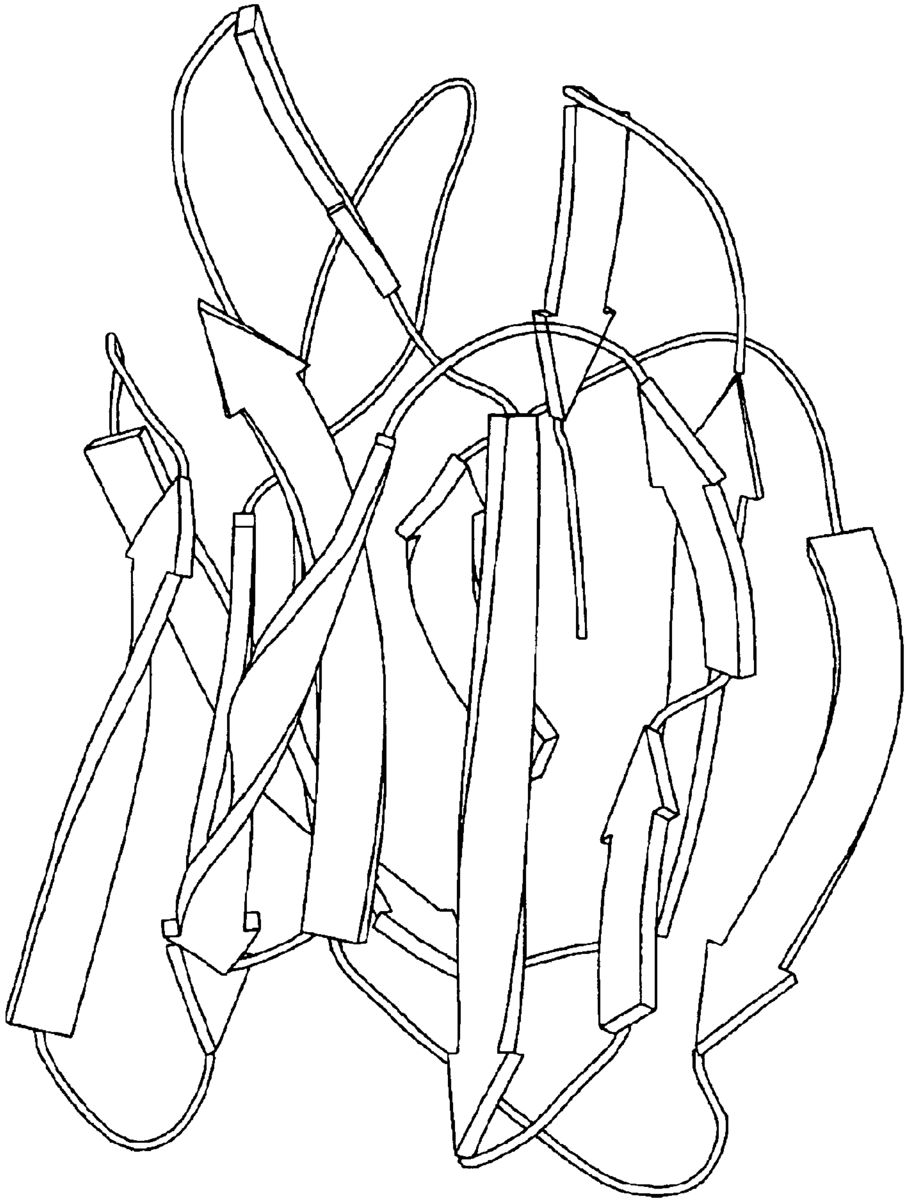
FIG. 14. (a) Molescript representation of the β prism model of AgfA. (b) Molescript representation of VMO-I protein using coordinates obtained from SCOP on which the AgfA β prism model was modeled as described in the Materials and Methods.
Figure 14B:
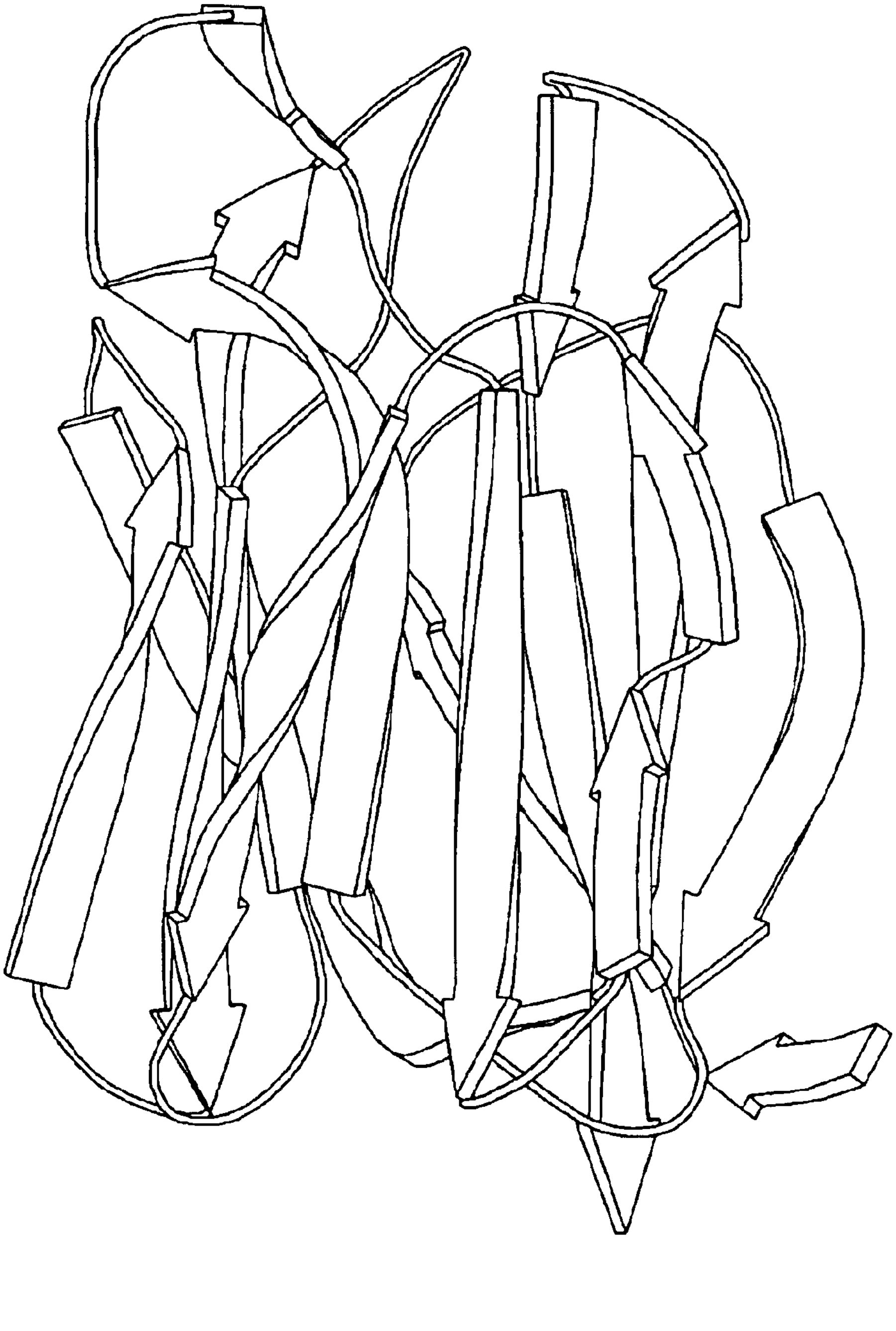

The AgfA β-prism model (FIG. 14*a*) was based on coordinates from the X-ray crystal structure of vitelline membrane outer protein, VMO-I (Shimizu & Morikawa, 1996; Shimizu et al., 1994) (FIG. 14*b*). This AgfA model predicted a fairly compact, elongated structure with several short β-strand regions of 3 to 6 residues joined by loops of random coil (FIG. 14*a*). The β-prism model did not reflect the five-repeat symmetry of the primary sequence but rather an organization of three repeats based upon the first, third and fifth repeat. The nonpolar residues were internalized to generate a hydrophobic core but the conserved N and Q residues of the five consensus repeats were generally surface exposed. The acidic residues and many of the hydroxyl-containing S and T residues were clustered towards the same end of the molecule where as basic residues were featured at both ends of the molecule. The F and Y residues were surface exposed but no extensive surface hydrophobic patches were predicted.

AgfA Model Quality

Each of the three model structures obtained for AgfA by homology modeling represented a reasonable, preliminary protein structure based on the VADAR statistical analyses performed (Table 4). Further refinements were not attempted at this stage since physical data on AgfA structure are not yet available to corroborate a given model. Each model predicted a series of β-strands separated by turns with the predicted surface-exposed residues in general agreement with proposed buried and surface exposed residues in each of the tertiary structure models (FIGS. 12, 13 & 14). However, the β-prism model deviated somewhat from the predicted surface exposed residues of AgfA in this respect.

Evolutionary Conservation of *Salmonella* AgfA Primary Amino Acid Consensus Sequence Previous alignment of the AgfA fimbrin subunit of *Salmonella* thin aggregative fimbriae with that of *E. coli* curli fimbriae indicated that these two proteins, including the signal sequence, were 74% identical and 86% similar (Collinson et al., 1996a). A more detailed analysis of the alignments of these two related fimbrins was performed to determine the pattern and extent of conservative versus non-conservative amino acid substitutions (FIG. 15, Table 5). The 22-residue N-terminal segment of AgfA was 82% (18/22) identical, but 91% (20/22) similar to CsgA if conserved residues were considered (Table 5). The 109 amino acids of the C-terminal domain were 71% (77/109) identical and 80% similar if ten additional conservative residue replacements were considered.

TABLE 5

Amino acid conservation between Salmonella AgfA and *E. coli* CsgA.

| Consensus sequence position[a] | Protein | Identity | Percent[b] (number of residues/total) Conservative | Different |
|---|---|---|---|---|
| Inside (*): | | | | |
| (1, 3, 5, 7, 12, 14, 16, 18) | AgfA/CsgA | 92.5 (37/40) | 5.0 (2/40) | 2.5 (1/40) |
| Outside (o): | | | | |
| (2, 4, 6, 13, 15, 17) | AgfA/CsgA | 50.0 (15/30) | 20.0 (6/30) | 30.0 (9/30) |

TABLE 5-continued

| Amino acid conservation between Salmonella AgfA and *E. coli* CsgA. | | | | |
|---|---|---|---|---|
| Consensus sequence position[a] | Protein | Identity | Percent[b] (number of residues/total) Conservative | Different |
| Turns (t): | | | | |
| (8–11, 19–23) | AgfA/CsgA | 64.1 (25/39) | 5.1 (2/39) | 30.8 (12/39) |

[a]The position of amino acids in each consensus sequence are labeled (*, o, t) according to parallel β helix models as in FIG. 9.
[b]Each residue of the AgfA fimbrin was compared to the respective amino acid in CsgA and assessed whether the pairs were identical, similar or different and scored according to the following groups; hydroxyl (T, S); acidic (E, D); basic (R, K, H); amide (Q, N); aromatic (Y, F, W); aliphatic (A, M, I, L, V) or glycine (G).

The distribution of identical and conserved residues compared to that of non-conserved residues within the repeated segments of the two fimbrins was very distinctive. In general, residues predicted to be internalized in the parallel β-helix model of AgfA were more highly conserved between the two fimbrin proteins than residues predicted to be on the β-sheet surfaces or at the predicted turn positions (FIG. 15, Table 5). Residues at positions 1,3,5,7 and 12,14,16,18 of each repeat motif were 92.5% identical and 5.0% conserved (FIG. 15, Table 5). However, residues occupying the alternate positions in the consensus sequence at predicted surface-exposed positions 2,4,6 and 13,14,15 of each repeat motif were only 50% (15/30) identical with an additional 20% (6/30) of the residues conserved for a 70% overall similarity (FIG. 15, Table 5). Similarly, the two regions comprising expected turns at positions 8,9,10,11 and 19,20, 21,22,23 had an overall similarity of 69.2% (FIG. 15, Table 5).

Discussion

Three hypothetical, all-β class tertiary structure models were assembled for AgfA, the fimbrin subunit protein of *Salmonella* thin aggregative fimbriae. These models represent the first predictions of a bacterial fimbrin or pilin tertiary protein structure using homology buildup and molecular modeling techniques. The primary amino acid sequence repeat motif comprising the protease-resistant AgfA C-terminal. core facilitated this novel approach to explore the tertiary structure of an aggregative structural protein.

One feature of the AgfA fimbrin of *Salmonella* thin aggregative fimbriae is the highly conserved, five-fold repeated consensus sequence, comprising 109 residues of the protease resistant C-terminal core region of the fimbrin. This region is preceded by a distinctive, protease-susceptible glycine-rich N-terminus of 17 to 22 residues. Except for the AgfA fimbrin homologue of *E. coli* curli, CsgA (Hammar et al., 1996), no other fimbrial proteins possess highly conserved, tandem primary amino acid sequence repeat motifs.

Analysis of other fimbrins and pilins using common predictive algorithms for secondary structure indicate that like AgfA, these structural proteins have β-strand conformations distributed throughout the subunit protein (Girardeau et al., 1991; Klemm, 1984; Lintermans et al., 1988). An analysis of 24 various bacterial fimbrins and pilins by the method of Garnier et al. (1978) similarly indicated 31% to 69% predicted β-strand content often with multiple β-strand motifs present throughout the protein (Collinson et al., unpublished data). The presence of amphipathic β-strands within various *Enterobacteriaceae* fimbrial components also has been recognized by hydrophobic cluster analysis (HCA) (Girardeau & Bertin, 1995; Méchin et al., 1995). Using HCA, fimbrial protein components of thick (7 nm) fimbriae that possess a cysteine loop are distinct structurally from those comprising thin fimbriae and lacking a cysteine loop (Girardeau & Bertin, 1995; Méchin et al., 1995). However, the AgfA C-terminal core is predicted to adopt a very unusual, regular repeating secondary structural pattern with most of the ten nonpolar-polar-nonpolar triplet motifs adopting extended secondary structure separated by short regions of coil structure. *Salmonella* AgfA, and the *E. coli* AgfA homologue, CsgA (Hammar et al., 1996), may be an extreme case in which the obvious, highly conserved amino acid residues in the primary sequence repeat motifs reflect a regular predicted secondary structure pattern.

Several features of the AgfA primary sequence and predicted secondary structure suggest that AgfA probably adopts a tertiary structure distinct from the Figure α-β roll described for the gonococcal pilin of *Neisseria* type IV pili. Notably, AgfA lacks the 55 amino acid hydrophobic, a-helical N-terminal region proposed to occupy an internal position in intact pili (Paranchych & Frost, 1988; Parge et al., 1995). The four central anti-parallel β strands of the gonococcus pilin are flanked between the C-terminal portion of the 55-residue N-terminal a-helix and the externally exposed disaccharide-containing loop and disulfide region (Parge et al., 1995). AgfA lacks extensive regions of predicted a-helical structure and does not contain cysteine residues (Collinson et al., 1996a; Collinson et al., 1991). Post translational modification of AgfA has not been demonstrated but two putative NAT O-glycosylation sites exist at residues 80 to 82 and 115 to 117 analagous to the N(T/S)S O-glycosylation site of gonoccal and menigococcal pilins (Marceau et al., 1998). Predictably, the actual *S. enteritidis* AgfA fimbrin tertiary structure likely differs significantly from the α-β roll of gonnococcal pilin.

The parallel β helix model of AgfA is the most alluring tertiary structure emerging from this study for several reasons. Firstly, this model predicts a very regular, compact structure congruent with the conserved, primary sequence repeats found in the C-terminus of AgfA. In addition, the proposed molecular mechanisms stabilizing the AgfA parallel β helix model structure are reminiscent of those of the di-strand β roll motif of the *S. marcescens* metallo-protease on which this AgfA model was based (Baumann, 1994) and the stucturally related tri-strand parallel β helix motif of the pectate lyases (Lietzke et al., 1994; Pickersgill et al., 1994; Yoder & Jurnak, 1995) and *Salmonella* P22 phage tail spike protein (Steinbacher et al., 1994; Yoder & Jurnak, 1995) with potentially important differences. The predicted parallel β helix AgfA structure would be expected to be more stable than the above helical structures. This is because the parallel β helix model of AgfA predicts that four residues in each of the five coils would be internalized forming a larger hydrophobic core compared to the two residues normally seen in the previously described β roll and parallel β-helix motifs (Yoder & Jurnak, 1995). The intriguing arrangement of two internalized stacks of five Q and five N residues at positions 7 and 12, respectively, that flank the relatively sharp turn centered at the conserved G residue at position 9 of each coil could apparently stabilize the turns by extensive H-bonding with the peptide chain backbone (FIG. 11*c*). Similarly, two internalized stacks of five S and five Q residues at positions 1 and 18 flank the turns joining each coil. The pectate lysases, which demonstrate polar stacks of up to 6 N residues and 3 S residues merely possess a single polar stack on one side of each turn (Yoder & Jurnak, 1995). Similarly, ribonuclease inhibitor, a protein containing leucine-rich repeats folded in a helix of alternating strand and a helical regions possesses an N ladder at one end of the strand motif ADDIN ENRef (Kobe & Deisenhofer, 1993). Conversly, the barrel and prism AgfA model structures apparently lack certain molecular interactions important for the stability of respective template proteins. The PMP barrel structure possesses many hydrophilic residues that project into the interior of the barrel and form an extensive network of hydrogen bonds and salt bridges with a non-central hydrophobic pocket within the barrel structure that interacts with lipids ADDIN ENRef (Cowan et al., 1993; Jones et al., 1988). Furthermore, the AgfA barrel model is less extensively hydrogen bonded than its PMP template. In addition, AgfA lacks cysteine residues, eight of which apparently stabilize the prism structure of VMO-I and enhance heat stability by forming four internal S-S bridges ADDIN ENRef (Shimizu & Morikawa, 1996).

Thirdly, the conservation of residues in the AgfA and CsgA fimbrin homologues is a strong evolutionary argument in support of the AgfA parallel helix model. The hypothetical contribution of the internal, conserved polar and nonpolar residues to the stability of this model is further strengthened by the fact that 37 of these 40 residues are identical in the AgfA homologue, CsgA. The residues forming the stacks of internalized polar residues are perfectly conserved and there is only one non-conservative replacement of L for T in AgfA within the predicted hydrophobic core (FIG. 15, Table 5). In this context, it is more difficult to envision the necessity for conserving these residues in the proposed barrel model of AgfA which predicts internal positions of these polar residues but without an obvious role in stability given the less extensive participation in main chain hydrogen bonding. Similary, structural integrity and stability of the prism model would not conceivably require the conservation of N and Q residues which are predicted to be mainly surface exposed in this model. Conservation of residues is a strong argument for eliminating barrel and the prism models. If AgfA forms a parallel helix structure, this would be the first fimbrin recognized to do so.

Parallel sheet structures, like those described for the proposed AgfA parallel helix model are often associated with protein-protein interactions. Although metalloproteases ADDIN ENRef (Baumann et al., 1995; Baumann et al., 1993) and pectate lyases (Yoder & Jurnak, 1995) form coiled fold motifs that do not exist in multimeric form, the P22 tailspike protein forms a native trimer that is resistant to proteases, thermostable beyond 80° C. and is not dissociated by exposure to SDS (Steinbacher et al., 1994). The stability of the P22 tailspike trimer is attributed to the interaction of the hydrophilic β sheet surfaces (Steinbacher et al., 1994). The possibility that the unusual stability of polymerized AgfA and the aggregative nature of the fimbriae is due in part to electrostatic interactions between monomers is consistent with the observed resistance of thin aggregative fimbriae to depolymerization by treatment with SDS (Collinson et al., 1991), octylglucoside or Tween-20 (Collinson, unpublished data). Salt bridges as well as hydrophobic interactions contribute to the maintenance of trimeric forms of carbonic anhydrase, the monomers of which assume a left hand parallel β helix structure (Kisker et al., 1996). Very little is known concerning the molecular basis for fimbrin polymerization and stability. Forces important in the *Neisseria* Type IV model implicate a combination of a hydrophobic N-terminus in the central core of the fiber and electrostatic forces stabilizing subunit-subunit interactions in the globular head (Parge et al., 1995). Fimbrins and pilins are not covalently linked but assemble into very stable structures resistant to proteases and chemical denaturants such as chaotropes and alkali (Collinson et al., 1991; Eshdat et al., 1981; Ho et al., 1990; Korhonen et al., 1980; Parge et al., 1995). The distribution of those amino acid residues predicted to comprise the external face of the amphipathic β-strands in the parallel β helix AgfA model are primarily polar with hydrophobic, acidic and basic "patches" consistent with a requirement for interactive surfaces to stabilize polymers of AgfA. The glycine rich N-terminal region of AgfA, while susceptible to protease digestion, also posses a sequence consistent with two glycine loops as defined by Steinert et al. (1991) which have been hypothesized to form interactions that stabilize higher structures. The parallel β helix model of AgfA offers an interesting solution to a multifunctional fimbrin molecular surface that must be able to have regions for subunit-subunit interaction, solvent exposed areas, interaction with minor subunits and fiber-fiber interactions common to many fimbriae.

The three all-β class tertiary structure models of AgfA enable rational experimental design to facilitate investigations into *Salmonella* thin aggregative fimbriae structure and biogenesis. The quest to obtain soluble AgfA monomers for future physical analysis or structural studies may be aided by considering the information offered by the hypothetical AgfA model structures, especially that of the AgfA parallel β helix model. Optimal conditions for depolymerization of thin aggregative fimbriae in conditions less severe than 90% formic acid or prevention of AgfA polymerization by introducing minor tertiary structural perturbations by site specific mutagenesis may be ways to obtain soluble fimbrin monomers. Selective mutagenesis of AgfA to identify structurally and functionally important regions of this fimbrin is currently in progress (White et al., 1999). Site specific mutagenesis to alter key amino acid residues conserved in the AgfA primary sequence should provide important information on fimbrin structure and stability and the importance of each of the five C-terminal repeat segments in AgfA. Site specific mutagenesis of the K99 fimbrin penultimate Y prevents fiber formation (Simons et al., 1990). The role of the terminal Y of AgfA is not known, however, this residue is positioned 3 and 5 residues C-terminally to the two hydrophobic residues of the tenth β-strand and 9 residues from F122, an arrangement reminiscent of the less conserved β-zipper motif of fimbrins assembled by the FGL chaperones (Hung et al., 1996). The possibility of chaperone involvement in AgfA assembly has not been ruled out. Thus, the agfA structural models presented herein provide a theoretical basis from which to further our knowledge of the structure and biogenesis of the stable, thin aggregative fimbriae of *Salmonella.*

References Cited in Example 1

Abraham, S. N., Babu, J. P., Giampapa, C. S., Hasty, D. L., Simpson, W. A. & Beachey, E. H. (1985). Protection against *Escherichia coli*-induced urinary tract infections with hybridoma antibodies directed against type 1 fimbriae or complementary D-mannose receptors. *Infection and Immunity* 48, 625–628.

Austin, J. W., Sanders, G., Kay, W. W. & Collinson, S. K. (1998). Thin aggregative fimbriae enhance *Salmonella enteritidis* biofilm formation. *FEMS Microbiology Letters* 162, 295–301.

Baumann, U. (1994). Crystal structure of the 50 kDa metallo-protease from *Serratia mercescens. Journal of Molecular Biology* 242, 244–251.

Baumann, U., Bauer, M., Létoffé, S., Delepelaire, P. & Wandersman, C. (1995). Crystal structure of a complex between *Serratia marcescens* metallo-protease and an inhibitor from *Erwinia chrysanthemi. Journal of Molecular Biology* 248, 653–661.

Baumann, U., Wu, S., Flaherty, K. M. & McKay, D. B. (1993). Three-dimensional structure of the alkaline protease of *Pseudomonas aeruginosa*: a two-domain protein with a calcium binding parallel beta roll motif. *EMBO Journal* 12, 3357–3364.

Bäumler, A. J., Gilde, A. J., Tsolis, R. M., van der Velden, A. W. M., Ahmer, B. M. M. & Heffron, F. (1997). Contribution of horizontal gene transfer and deletion events to development of distinctive patterns of fimbrial operons during evolution of *Salmonella* serotypes. *Journal of Bacteriology* 179, 317–322.

Bäumler, A. J. & Heffron, F. (1995). Identification and sequence analysis of lpfABCDE, a putative fimbrial operon of *Salmonella typhimurium. Journal of Bacteriology* 177, 2087–2097.

Bernstein, F. C., Koetzle, T. F., Williams, G. J. B., Meyer, E. F., Brice, M. D., Rodgers, J. R., Kennard, O., Shimanouchi, T. & Tasumi, M. (1977). The Protein Data Bank: a computer-based archival file for macromolicular structures. *Journal of Molecular Biology* 112, 535–542.

Braunagel, S. C. & Benedik, M. J. (1990). The metalloprotease gene of *Serratia marcescens* strain SM6. *Molecular and General Genetics* 222, 446–451.

Brinton Jr, C. C. (1965). The structure, function, synthesis and genetic control of bacterial pili and a molecular model for DNA and RNA transport in gram negative bacteria. *Transactions of the New York Academy of Sciences* 27, 1003–1054.

Collinson, S. K., Clouthier, S. C., Doran, J. L., Banser, P. A. & Kay, W. W. (1996a). *Salmonella enteritidis* agfBAC operon encoding thin, aggregative fimbriae. *Journal of Bacteriology* 178, 662–667.

Collinson, S. K., Doig, P. C., Doran, J. L., Clouthier, S., Trust, T. J. & Kay, W. W. (1993). Thin, aggregative fimbriae mediate binding of *Salmonella enteritidis* to fibronectin. *Journal of Bacteriology* 175, 12–18.

Collinson, S. K., Emödy , L., Müller, K.-H., Trust, T. J. & Kay, W. W. (1991). Purification and characterization of thin, aggregative fimbriae from *Salmonella enteritidis. Journal of Bacteriology* 173, 4773–4781.

Collinson, S. K., Emödy , L., Trust, T. J. & Kay, W. W. (1992). Thin aggregative fimbriae from diarrheagenic *Escherichia coli. Journal of Bacteriology* 174, 4490–4495.

Collinson, S. K., Liu, S.-L., Clouthier, S. C., Banser, P. A., Doran, J. L., Sanderson, K. E. & Kay, W. W. (1996b). The location of four fimbrin-encoding genes, agfA, fimA, sefA and sefD, on the *Salmonella enteritidis* and/or *S. typhimurium* XbaI-BlnI genomic restriction maps. Gene 169, 75–80.

Cowan, S. W., Newcomer, M. E. & Jones, T. A. (1993). Crystallographic studies on a family of cellular lipophilic transport proteins. *Journal of Molecular Biology* 230, 1225–1246.

de Graaf, F. K. & Bakker, D. (1992). Properties and synthesis of K88 fimbriae. In *Molecular recognition in Host-Parasite Interactions* (Korhonen, T. K., ed.), pp. 39–46. Plenum Press, New York.

Der Vartanian, M., Méchin, M.-C., Jaffeux, B., Bertin, Y., Félix, I. & Gaillard-Martinie, B. (1994). Permissible peptide insertions surrounding the signal peptide-mature protein junction of the ClpG prepilin: CS31A fimbriae of *Escherichia coli* as carriers of foreign sequences. *Gene* 148, 23–32.

Doran, J. L., Collinson, S. K., Burian, J., Sarlós, G., Todd, E. C. D., Munro, C. K., Kay, C. M., Banser, P. A., Peterkin, P. I. & Kay, W. W. (1993). DNA-based diagnostic tests for *Salmonella* species targeting agfA, the structural gene for thin, aggregative fimbriae. *Journal of Clinical Microbiology* 31, 2263–2273.

Eshdat, Y., Silverblatt, F. J. & Sharon, N. (1981). Dissociation and reassembly of *Escherichia coli* type 1 pili. *Journal of Bacteriology* 148, 308–314.

Firth, N., Ippen-Ihler, K. & Skurray, R. A. (1996). Structure and function of the F facator and mechanism of conjugation. In *Escherichia coli* and *Salmonella Cellular and Molecular Biology* 2nd edit. (Neidhardt, F. C., ed.), pp. 2377–2401. American Society for Microbiology Press, Washington, D.C.

Fullner, K. J., Lara, J. C. & Nester, E. W. (1996). Pilus assembly by *Agrobacterium* T-DNA transfer genes. *Science* 273, 1107–1109.

Gaastra, W. & de Graaf, F. K. (1982). Host-specific fimbrial adhesins of noninvasive enterotoxigenic *Escherichia coli* strains. *Microbiological Reviews* 46, 129–161.

Girardeau, J.-P. & Bertin, Y. (1995). Pilins of fimbrial adhesins of different member species of Enterobacteriaceae are structurally similar to the C-terminal half of adhesin proteins. *FEBS Letters* 357, 103–108.

Girardeau, J.-P., Bertin, Y., Martin, C., Der Vartanian, M. & Boeuf, C. (1991). Sequence analysis of the clpG gene, which codes for surface antigen CS31A subunit: evidence of an evolutionary relationship between CS31A, K88 and F41 subunit genes. *Journal of Bacteriology* 173, 7673–7683.

Gong, M. & Makowski, L. (1992). Helical structure of P pili from *Escherichia coli. Journal of Molecular Biology* 228, 735–742.

Hammar, M., Arvqvist, A., Bian, Z., Olsen, A. & Normark, S. (1995). Expression of two csg operons is required for production of fibronectin- and congo red-binding curli polymers in *Escherichia coli* K-12. *Molecular Microbiology* 18.

Hammar, M., Bian, Z. & Normark, S. (1996). Nucleator-dependent intercellular assembly of adhesive curli organelles in *Escherichia coli. Proceedings of the National Academy of Science* 93, 6562–6566.

Heck, D. V., Trus, B. L. & Steven, A. C. (1996). Three-dimensional Structure of *Bordetella pertussis* fimbriae. *Journal of structural Biology* 116, 264–269.

Ho, A. S. Y., Mietzner, T. A., Smith, A. J. & Schoolnik, G. K. (1990). The pili of *Aeromonas hydrophila:* identification of an environmentally regulated "mini pilin". *Journal of Experimental Medicine* 172, 795–806.

Hobohm, U. & Sanders, C. (1995). A sequence property approach to searching protein databases. *Journal of Molecular Biology* 251, 390–399.

Hung, D. L., Knight, S. D., Woods, R. M., Pinkner, J. S. & Hultgren, S. J. (1996). Molecular basis of two subfamilies of immunoglobulin-like chaperones. *EMBO Journal* 15, 3792–3805.

Jones, C. H., Danese, P. N., Pinkner, J. S., Silhavy, T. J. & Hultgren, S. J. (1997). The chaperone-assisted membrane release and folding pathway is sensed by two signal transduction systems. *EMBO Journal* 16, 6394–6406.

Jones, T. A., Bergfors, T., Sedzik, J. & Unge, T. (1988). The three-dimensional structure of P2 myelin protein. *EMBO Journal* 7, 1597–1604.

Kisker, C., Schindelin, H., Alber, B. E., Ferry, J. G. & Rees, D. C. (1996). A left-handed β-helix revealed by the crystal structure of a carbonic anhydrase from the archaeon *Methanosarcina thermophila. EMBO Journal* 15, 2323–2330.

Klemm, P. (1984). The fimA gene encoding the type-1 fimbrial subunit of *Escherichia coli. European Journal of Biochemistry* 143, 395–399.

Klemm, P. & Krogfelt, K. A. (1994). Type 1 fimbriae of *Escherichia coli*. In *Fimbriae adhesion, genetics, biogenesis, and vaccines* (Klemm, P., ed.), pp. 9–26. CRC Press, Baco Raton.

Kobe, B. & Deisenhofer, J. (1993). Crystal structure of porcine ribonuclease inhibitor, a protein with leucine-rich repeats. *Nature* 366, 751–756.

Korhonen, T. K., Nurmiaho, E.-L., Ranta, H. & Eden, C. S. (1980). New method for isolation of immunologically pure pili from *Escherichia coli. Infection and Immunity* 27, 569–575.

Kuehn, M. J., Haslam, D., Normark, S. & Hultgren, S. J. (1994). Structure, function and biogenesis of *Escherichia coli* P pili. In *Fimbriae adhesion, genetics, biogenesis, and vaccines* (Klemm, P., ed.). CRC Press, Boca Raton.

Kuehn, M. J., Heuser, J., Normark, S. & Hultgren, S. J. (1992). P pili in uropathogenic *E. coli* are composite fibres with distinct fibrillar adhesive tips. *Nature* 356, 252–255.

Laemmli, U. K. (1970). Cleavage of structural proteins during the assembly of the head of bacteriophage T4. *Nature* 227, 680–685.

Lai, E.-M. & Kado, C. I. (1998). Processed VirB2 is the major subunit of the promiscuous pilus of *Agrobacterium tumefaciens. Journal of Bacteriology* 180, 2711–2717.

Leathart, J. B. S. & Gally, D. L. (1998). Regulation of type 1 fimbrial expression in uropathogenic *Escherichia coli*: heterogeneity of expression through sequence changes in the fim switch region. *Molecular Microbiology* 28, 371–381.

Levine, M. M., Giron, J. A. & Noriega, F. R. (1994). Fimbrial vaccines. In *Fimbriae adhesion, genetics, biogenesis and vaccines* (Klemm, P., ed.), pp. 255–270. CRC Press, Boca Raton.

Lietzke, S. E., Yoder, M. D., Keen, N. T. & Jurnak, F. (1994). The three-dimensional structure of pectate lyase E, a plant virulence factor from *Erwinia chrysanthemi. Plant Physiology* 106, 849–862.

Lintermans, P., Pohl, P., Deboeck, F., Bertels, A., Schlicker, C., Vandekerckhove, J., van Damme, J., van Montagu, M. & de Greve, H. (1988). Isolation and nucleotide sequence of the F17-A gene encoding the structural protein of the F17 fimbriae in bovine enterotoxigenic *Escherichia coli. Infection and Immunity* 56, 1475–1484.

Low, D., Braaten, B. & van der Woude, M. (1996). Fimbriae. In *Escherichia coli and Salmonella Cellular and Molecular Biology* 2nd edit. (Neidhardt, F. C., ed.), pp. 146–157. American Society for Microbiology Press, Washington, D.C.

Marceau, M., Beretti, J.-L. & Nassif, X. (1995). High adhesiveness of encapsulated *Neisseria meningitidis* to epithelial cells is associated with the formation of bundles of pili. *Molecular Microbiology* 17, 855–863.

Marceau, M., Forest, K., Béretti, J.-L., Tainer, J. & Nassif, X. (1998). Consequences of the loss of O-linked glycosylation of menningococcal type IV pilin on piliation and pilus-mediated adhesion. *Molecular Microbiology* 27, 705–715.

Méchin, M.-C., Bertin, Y. & Girardeau, J.-P. (1995). Hydrophobic cluster analysis and secondary structure predictions revealed that major and minor structural subunits of K88-related adhesins of *Escherichia coli* share a common overall fold and differ structurally from other fimbrial subunits. *FEBS Letters* 364, 319–324.

Mol, O. & Oudega, B. (1996). Molecular and structural aspects of fimbriae biosynthesis and assembly in *Escherichia coli. FEMS Microbiology Reviews* 19, 25–52.

Morris, A. L., MacArthur, M. W., Huchinson, E. G. & Thornton, J. M. (1992). Stereochemical quality of protein structure coordinates. *Proteins* 12, 345–364.

Murzin, A. G., Brenner, S. E., Hubbard, T. & Chothia, C. (1995). SCOP: A structural classification of proteins database for the investigation of sequences and structures. *Journal of Molecular Biology* 247, 536–540.

Ogawa, T., Ogo, H. & Kinoshita, A. (1997). Antagonsitic effect of synthetic peptides corresponding to the binding regions within fimbrial subunit protein from *Porphyromonas gingivalis* to human gingival fibroblasts. *Vaccine* 15, 230–236.

Olsén, A., Arnqvist, A., Hammar, M., Sukupolvi, S. & Normark, S. (1993). The RpoS sigma factor relieves H-NS-mediated transcriptional repression of csgA, the subunit gene of fibronectin-binding curli in *Escherichia coli. Molecular Microbiology* 7, 523–536.

Pallesen, L. & Klemm, P. (1994). Chimeric fimbrial vaccines. In *Fimbriae adhesion, genetics, biogenesis, and vaccines* (Klemm, P., ed.), pp. 271–276. CRC Press, Boca Raton.

Paranchych, W. (1990). Molecular studies on N-methylphenylalanine pili. *The Bacteria XI,* 61–78.

Paranchych, W. & Frost, L. S. (1988). The physiology and biochemistry of pili. *Advances in microbial physiology* 29, 53–114.

Parge, H. E., Forest, K. T., Hickey, M. J., Christensen, D. A., Getzoff, E. D. & Tainer, J. A. (1995). Structure of the fiber-forming protein pilin at 2.6 Å resolution. *Nature* 378, 32–38.

Parker, J. M. R. & Hodges, R. S. (1991a). Prediction of surface and intenior regions in proteins—Part I: Linear tripeptide sequences identify structural boundaries in proteins. *Peptide Research* 4, 347–354.

Parker, J. M. R. & Hodges, R. S. (1991b). Prediction of surface and interior regions in proteins—PartII: predicting secondary structure in regions bound by surface exposed regions. *Peptide Research* 4, 355–363.

Pickersgill, R., Jenkins, J., Harris, G., Nasser, W. & Robert-Baudouy, J. (1994). The structure of *Bacillus subtilis* pectate lyase in complex with calcium. *Structural Biology* 1, 717–723.

Römling, U., Bian, Z., Hammar, M., Sierralta, W. D. & Normark, S. (1998). Curli fibers are highly conserved between *Salmonella typhimurium* and *Escherichia coli* with respect to operon structure and regulation. *Journal of Bacteriology* 180, 722–731.

Shimizu, T. & Morikawa, K. (1996). The β-prism: a new folding motif. *Trends in Biochemical Sciences* 21, 3–6.

Shimizu, T., Vassylyev, D. G., Kido, S., Doi, Y. & Morikawa, K. (1994). Crystal structure of vitelline membrane outer layer protein I (VMO-I): a folding motif with homologous Greek key structures related by an internal three-fold symmetry. *EMBO Journal* 13, 1003–1010.

Silverman, P. M. (1997). Towards a structural biology of bacterial conjugation. *Molecular Microbiology* 23, 423–429.

Simons, B. L., Mol, O., van Breemen, J. F. L. & Oudega, B. (1994). Morphological appearances of K88ab fimbriae and optical diffraction analysis of K88 paracrystalline structures. *FEMS Microbiology Letters* 118, 83–88.

Simons, B. L., Rathman, P., Malij, C. R., Oudega, B. & de Graaf, F. K. (1990). The penultimate tyrosine residue of the K99 fibrillar subunit is essential for stability of the protein and its interaction with the periplasmic carrier protein. *FEMS Microbiology Letters* 67, 107–112.

Sjöbring, U., Pohl, G. & Olsén, A. (1994). Plasminogen, absorbed by *Escherichia coli* expressing curli or by *Salmonella enteritidis* expressing thin aggregative fimbriae, can be activated by simultaneously captured tissue-type plasminogen activator (t-PA). *Molecular Microbiology* 14, 443–452.

Smyth, C. J., Marron, M. B., Twohig, J. M. G. J. & Smith, S. G. J. (1996). Fimbrial adhesins: similarities and variations in structure and biogenesis. *FEMS Immunology and Medical Mirobiology* 16, 127–139.

St. Geme III, J. W., Pinkner, J. S., Krasan, G. P., Heuser, J., Bullitt, E., Smith, A. L. & Hultgren, S. J. (1996). *Haemophilus infuenzae* pili are composite structures assembled via the HifB chaperone. *Proccedings of the National Academy of Science* 93, 11913–11918.

Steinbacher, S., Seckler, R., Miller, S., Steipe, B., Huber, R. & Reinemer, P. (1994). Crystal structure of P22 tailspike protein: interdigitated subunits in a thermostable trimer. *Science* 265, 383–386.

Strom, M. S. & Lory, S. (1993). Structure-function and biogenesis of the type IV pili. *Annual Review of Microbiology* 47, 565–596.

Sukupolvi, S., Edelstein, A., Rhen, M., Normark, S. J. & Pfeifer, J. D. (1997a). Development of a murine model of chronic *Salmonella* infection. *Infection and Immunity* 65, 838–842.

Sukupolvi, S., Lorenz, R. G., Gordon, J. I., Bian, Z., Pfeifer, J. D., Normark, S. J. & Rhen, M. (1997b). Expression of thin aggregative fimbriae promotes interaction of *Salmonella typhimurium* SR-11 with mouse small intestinal epithelial cells. Infection and Immunity 65, 5320–5325.

Tennent, J. M. & Mattick, J. S. (1994). Type 4 fimbriae. In *Fimbriae adhesion, genetics, biogenesis, and vaccines* (Klemm, P., ed.), pp. 127–146. CRC Press, Boca Raton.

Thorns, C. J., McLaren, I. M. & Sojka, M. G. (1994). The use of latex particle agglutination to specifically detect *Salmonella enteritidis*. *International Journal of Food Microbiology* 21, 47–53.

Vidal, O., Longin, R., Prigent-Combaret, C., Dorel, C., Hooreman, M. & Lejeune, P. (1998). Isolation of an *Escherichia coli* K-12 mutant strain able to form biofilms on inert surfaces: involvement of a new ompR allele that increases curli expression. *Journal of Bacteriology* 180, 2442–2449.

White, A. P., Collinson, S. K., Burian, J., Clouthier, S. C., Banser, P. A. & Kay, W. W. (1999). High efficiency gene replacement in *Salmonella enteritidis*: Chimeric fimbrins containing a T cell epitope from *Leishmania major*. Vaccine, In press.

Whittaker, C. J., Klier, C. M. & Kolenbrander, P. E. (1996). Mechanisms of adhesion by oral bacteria. *Annual Review of Microbiology* 50, 513–552.

Wishart, D. S., Boyko, R. F., Willard, L., Richards, F. M. & Sykes, B. D. (1994). SEQSEE: a comprehensive program suite for protein sequence analysis. *Computer Applications in the Biosciences* 10, 121–132.

Wishart, D. S., Willard, L., Richards, F. M. & Sykes, B. D. (1995). VADAR: a comprehensive program for protein structure evaluation. Version 1.2. University of Alberta, Edmonton, Canada.

Yoder, M. D. & Jurnak, F. (1995). The parallel β helix and other coiled folds. *FASEB Journal* 9, 335–342.

EXAMPLE 2

High Efficiency Gene Replacement in *Salmonella enteritidis*: Chimeric Fimbrins Containing a T Cell Epitope from *Leishmania major*

The present invention provides for a simple, highly efficient method for gene replacement within the chromosome of *Salmonella*. This method is advantageous because it allows for gene replacement at native sites in the chromosome without the need for specific recombination-proficient bacterial strains or the use of selectable markers within the recombinant genes. Thus, the incorporation of non-target DNA in the chromosome is avoided. To illustrate the utility of this method, sefA and agfA, encoding the fimbrin subunit proteins of SEF14 [8] and thin aggregative fimbriae (SEF17) [11], respectively, were engineered to contain the DNA sequence encoding an immunoprotective T cell epitope from the *Leishmania major* surface protein, GP63 [25], and were replaced into the chromosome of *S. enteritidis*. To our knowledge, this study presents the first chimeric *Salmonella* fimbrin genes and reports the first example of chimeric fimbrin genes reconstituted into the chromosome of an otherwise wild-type organism.

Materials and Methods

Bacterial Strains, Media, and Growth Conditions

*S. enteritidis* 27655 strain 3b has been previously described [16]. *E. coli* XL-1 Blue (Stratagene) was used as the host for pTZ18R, pHSG415, pGEM-T, pGP1-2 and their derivatives (Table 6).

TABLE 6

Plasmids used in this study.

| Plasmid | Description and relevant genotypes | Reference/Source |
|---|---|---|
| pTZ18R | Standard cloning vector with T7 promoter; $Ap^R$ | Pharmacia Biotech Inc. |
| pHSG415 | Temperature-sensitive pSC101 ori; $Cm^R$, $Km^R$, $Ap^R$ | [20] |
| pGEM-T | A-T cloning vector; $Ap^R$ | Stratagene |
| pGP1-2 | T7 RNA polymerase cloned under the control of $1p_L$ and cI857, P15A ori; $Km^R$ | [44] |
| pTZ18 pil | pTZ18R, sefABC | [8] |
| pHAG | pUC18, agfBAC | [9] |
| pTZSef | pTZ18R, sefA | This study |
| pTZSP10 | pTZ18R, sefA::PT3 | This study |
| pTZAgf | pTZ18R, agfA | This study |
| pTZAP7 | pTZ18R, agfA::PT3 | This study |
| pHSSP10 | pHSG415, sefA::PT3 | This study |
| pHSAP7 | pHSG415 ,agfA::PT3 | This study |

*E. coli* XL-1 Blue harboring recombinant plasmids was grown in Luria-Bertani (LB) broth [39] or Terrific broth (TFB) [40] for 20–24 h at 28° C., 37° C., or 42° C. as specified below. Media were supplemented with ampicillin (Ap, 100 mg $ml^{-1}$), kanamycin (Km, 50 mg $ml^{-1}$), 5-bromo-4-chloro-3-indolyl-β-D-glactopyranoside (X-gal, 40 mg $ml^{-1}$), or isopropyl-β-D-thiogalacto-pyranoside (IPTG, 1 mM) as required.

SefA or AgfA fimbrins were analyzed from *S. enteritidis* cells grown in CFA broth [15] or T broth [11] statically at 37° C. for 48 h or incubated on T medium (T) and T medium Congo red indicator plates (TCR) as previously described [10].

Recombinant DNA Techniques and Sequencing

Electroporation of *S. enteritidis* and *E. coli* using purified plasmids (QIAprep spin kit, Qiagen) was performed using standard techniques (Gene pulser electroprotocol, BioRad). Recombinant plasmids were routinely purified using standard alkaline lysis plasmid preps [40]. Restriction enzyme digestions (New England Biolabs) and ligation reactions (Gibco-BRL, Stratagene) were performed as described by the manufacturers. DNA fragments or PCR products were separated by agarose gel electrophoresis and visualized by staining with ethidium bromide [40]. DNA fragments purified from agarose gels using the Sephaglas bandprep kit (Pharmacia) or QIAquick gel extraction kit (Qiagen) were used for subcloning and sequencing. All PCR and sequencing primers were synthesized using an Applied Biosystems Model 391 PCR-MATE EP DNA synthesizer (Applied Biosystems Inc.).

Polymerase Chain Reaction

Figure 17A:
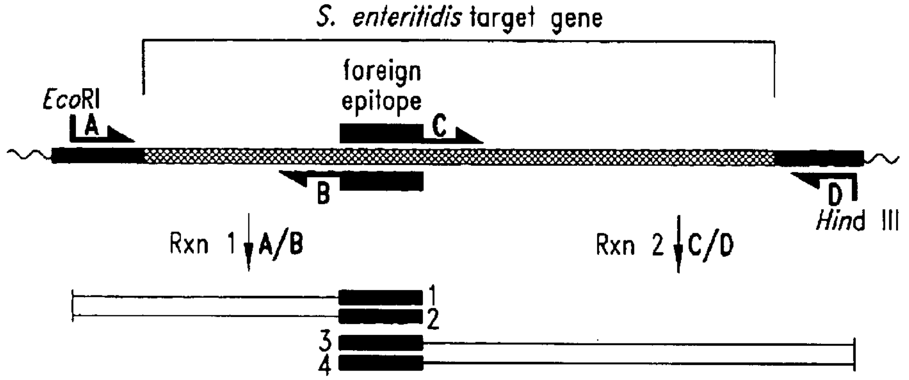
FIG. 17. Schematic of the two step overlap extension or crossover PCR protocol used to generate chimeric *S. enteritidis* genes. (A) Step one of the protocol involved a plasmid-borne (wavy lines) target *S. enteritidis* gene (grey box) that was PCR amplified in two fragments using two pairs of primers, (A/B, C/D, arrows). Internal primers encoded the foreign epitope (solid black line) whereas external primers encoded restriction endonuclease recognition sites (EcoRI or HindIII) for subsequent cloning. (B) In step two, both purified PCR products were combined with external primers as described in Experimental procedures and PCR was used to generate gene fragments (1 and 4) which annealed to generate the whole chimeric gene. (C) Chimeric *S. enteritidis* sefA and agfA fimbrin genes containing 48 bp foreign *Leishmania major* DNA sequence (SEQ ID NO: 9) encoding the 16 amino acid PT3 epitope [25] (SEQ ID NO: 10); the protein sequence is indicated in bold type.
Figure 17B:
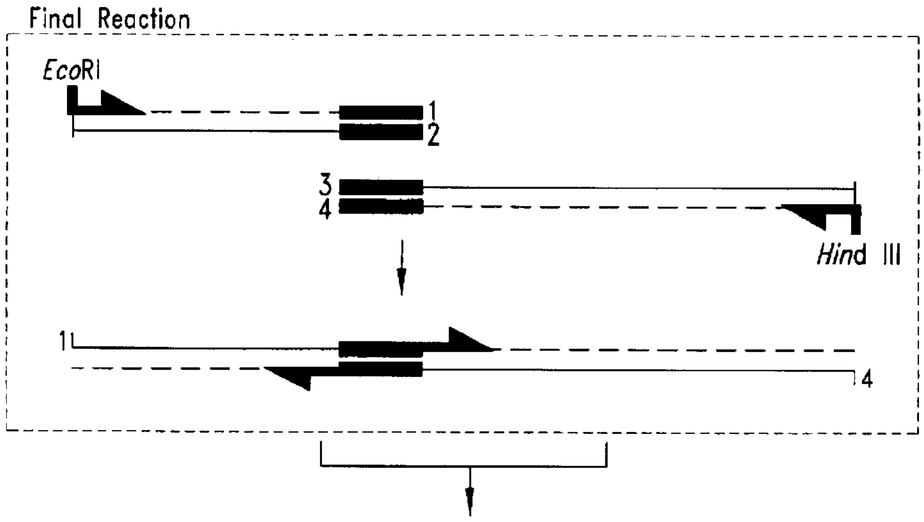

The two step overlap extension PCR reaction [22] to generate sefA::PT3 or agfA::PT3 required four primers, A, B, C, and D (FIG. 17). Primers B and C were the internal primers containing 48 nucleotides encoding the PT3 epitope followed by 30 nucleotides of sefA or agfA sequence at the desired site of insertion, and A and D were the two external primers containing EcoRI or HindIII restriction sites (Table 7). In the first PCR step, two separate 100 ml PCR reactions were performed using primers A/B and C/D, respectively (FIG. 17). Each amplification reaction contained 20 ng of plasmid template DNA, 50 pmol of each primer, 0.4 mM of each deoxynucleotide triphosphate (Boehringer Mannheim) and 2.5 U Pfu DNA polymerase (Stratagene) in buffer supplied by the manufacturer. The second PCR step required 50 ng each of the two purified PCR products from the first PCR step as template DNA with 50 pmol of each external primer. After an initial 4 min denaturation step at 94° C., the Pfu enzyme was added and thermocycling was performed in a PTC-100TM Programmable Thermal Controller (MJ Research Inc.) with 30 cycles of denaturation (94° C., 45 s), annealing (55° C., 45 s), elongation (72° C., 1 min), followed by a 10 min elongation at 72° C. Wild-type sefA or agfA genes were amplified using the external primers (A and D) only under the same conditions as the first PCR step described above.

To amplify regions surrounding sefA and agfA in $Ap^S$ *S. enteritidis* strains after gene replacement, primers IN1 (5'-GGG ATG TTG TGT AAA GAT AAA AAA ATA GTG-3') (SEQ ID NO: 55) and IN2 (5'-TGC CCA ATC TTA GGC CAT AAT ATT TTT GTG-3') (SEQ ID NO: 56) or TAF59 (5'-AGG AAG GAT CAA AAC TAT TGT CCG TTA TTT CAC-3') (SEQ ID NO: 57) and TAF60 (5'-TAT ATT TAC ACT AAG ACG AGA CAA CTC AAT CGG-3') (SEQ ID NO: 58) were used, respectively. To obtain template DNA for each *S. enteritidis* strain sequenced, cells from a 1 mL overnight LB culture were harvested and boiled for 10 min. in 1 mL $dH_2O$. 100 ml PCR reactions contained 20 ml of the boiled whole cell supernatant, 50 pmol of each primer, 0.2 mM of each deoxynucleotide triphosphate and 4 U of Taq DNA polymerase (Boehringer Mannheim) in buffer supplied by the manufacturer. After an initial 5 min denaturation step at 95° C., Taq enzyme was added and thermocycling was performed as above with 30 cycles of denaturation (94° C., 1 min), annealing (55° C. or 60° C., 1 min), elongation (72° C., 1 min), followed by a 10 min elongation at 72° C.

Gene Replacement Procedure in *S. enteritidis* 3b

*S. enteritidis* 3b containing pHSSP10 or pHSAP7 was grown for 24 h in 5 ml TFB/Ap (42° C., 250 rpm). 5 ml of this culture was used to inoculate 5 ml TFB/Ap and cells were grown at 42° C. for 24 h; this transfer step was repeated four times. To select $Ap^R$ colonies, dilutions of the final 42° C. culture were plated on LB/Ap plates and grown overnight at 42° C. pHSSP10 and pHSAP7 cointegrate colonies were grown individually in 5 ml TFB (28° C., 250 rpm, 24 h) 5 ml of each culture was used to inoculate 5 ml TFB and cells were grown at 28° C. for 24 h; this transfer step was repeated four times. Serial dilutions from each of the final 28° C. cultures were plated on LB medium and incubated at 28° C. for 24 h. To select $Ap^S$ colonies, isolated colonies were picked from LB and replica-plated onto LB/Ap plates.

DNA Sequence Analysis

Recombinant sefA::PT3 and agfA::PT3 generated by PCR were cloned into pTZ18R for sequence analysis. For analysis of $Ap^S$ *S. enteritidis* strains after gene replacement, PCR-generated products from the chromosome containing sefA or agfA and surrounding region were ligated into the A-T cloning vector, pGEM-T. To ensure the correct DNA sequence was obtained and to resolve errors due to Taq DNA

TABLE 7

PCR primers used to generate sefA::PT3 or agfA::PT3[a]

| Primers[b] | Length | Sequence[c] (5'—3') | SEQ ID NO |
|---|---|---|---|
| 14-A | 39 | TTG**GAATTC**TTCTTAAATTTTTAAAATGGCGTTGAGTAT | 47 |
| 14-B | 78 | AGCATGAGCCATTTCATGTGTAACAACACGTGTAACGAGCTGA<br>TCATATGCAATAGTAACCGCTGCCTGAACCACTGC | 48 |
| 14-C | 78 | TATGATCAGCTCGTTACACGTGTTGTTACACATGAAATGGCTCA<br>TGCTGGGCCTGCTGTTGCTGCTGGTCAGAAAGTT | 49 |
| 14-D | 39 | ATT**AAGCTT**ATACATAATCCCTCTTTAAGTTTTTGCATG | 50 |
| 17-A | 39 | GCA**GAATTC**AGCAGTTGTAGTGCAGAAACAGTCGCATAT | 51 |
| 17-B | 78 | TGCATGTGCCATTTCATGGGTAACAACACGGGTAACCAGCTGA<br>TCATAGTTTTTAGCGTTCCACTGGTCGATGGTGGC | 52 |
| 17-C | 78 | TATGATCAGCTGGTTACCCGTGTTGTTACCCATGAAATGGCACA<br>TGCAAATCAGACCGCATCTGATTCCAGCGTAATG | 53 |
| 17-D | 39 | AGACGC**AAGCTT**CGTTTAATGTGACCTGAGGGATCACCG | 54 |

[a]Primers used to generate sefA::PT3 or agfA::PT3 as noted in Fig 17.

[b]Primers prefixed with 14- or 17- used to generate sefA (SEF14) or agfA (SEF17) recombinants, respectively.

[c]Underlined sequence corresponds to the 48 bp PT3 DNA sequence; bold letters correspond to EcoRI (GAATTC) or HindIII (AAGCTT) restriction endonuclease sites.

polymerase, three individual pGEM-T isolates from each *S. enteritidis* strain were sequenced. Plasmid DNA used for sequence analysis was prepared using the QIAprep spin miniprep kit (Qiagen, CA). Sequencing primers used were the M13 universal forward and reverse primers. Sequencing was carried out using an Applied Biosystems Model 377 DNA Sequencing System and the PRISM Big Dye Primer or Big Dye Terminator Cycle Sequencing Ready Reaction Kit (Perkin-Elmer). Sequence data was analyzed using DNASTAR Lasergene software (DNASTAR, Inc.).

Expression of Chimeric Fimbrin Genes in *E. coli*

Expression of sefA::PT3 and agfA::PT3 in *E. coli* using T7 RNA polymerase was performed according to the method of Tabor and Richardson [44]. *E. coli* XL-1 Blue was co-electroporated with purified plasmids pTZAP7, pTZAgf, pTZSP10 , pTZSef or pTZ18R (control) along with pGP1-2. Cultures were grown in TFB/ApKm for 18 h (28° C., 200 rpm), one volume of pre-warmed media was added and the cultures were grown at 42° C. for 3 h to induce production of the cloned gene products. Cells were harvested at 4,000 rpm, normalized to 1.0 $A_{600}$, and processed as reported for *S. enteritidis* 3b [10] before SDS-PAGE and Western blotting.

Preparation of Immune Serum

Purified synthetic PT3 peptide was coupled to soluble keyhole limpet hemocyanin (KLH; Sigma) using glutaraldehyde [19]. Purified KLH-PT3 (330 mg) was resuspended in $dH_2O$ and emulsified in complete Freund's adjuvant prior to subcutaneous and intramuscular injections of a female New Zealand White rabbit. Two booster doses of KLH-PT3 (330 mg) emulsified in incomplete Freund's adjuvant were given at 4 week intervals. Titers of the immune serum were determined by enzyme-linked immunosorbent assay (ELISA) against the PT3 peptide. The rabbit was exsanguinated 4 weeks following the final booster injection. This serum was passaged over an immunoaffinity column which was prepared by coupling PT3 to CNBr-activated Sepharose 4B (Pharmacia) following procedures outlined by the manufacturer. The eluate from this column was pooled, tested for reactivity to PT3 by ELISA, and concentrated 10-fold using an ultrafiltration cell (Amicon model #8010) with a YM10 membrane (Amicon). This concentrated antibody solution was used as the final PT3-specific immune serum. Immune sera to whole SEF14 and SEF17 fimbriae have been previously described [8,11].

SDS-PAGE and Western Blot Analysis

For analysis of *S. enteritidis* strains after sefA::PT3 gene replacement, cells from 1 ml of 1 $A_{600}$ culture were harvested, resuspended in 200 ml of SDS-PAGE sample buffer supplemented with 0.2 M glycine (pH 2), and boiled for 10 min. This cell extract was clarified by spinning in a microcentrifuge (13,200 rpm, 5 min.) and used directly for SDS-PAGE analysis [7]. For analysis of *S. enteritidis* strains after agfA::PT3 gene replacement, cells were scraped from TCR plates using a glass slide and resuspended in 1 ml Tris buffer (10 mM Tris, pH 7.5). Aliquots of this cell slurry were mixed with an equal volume of 2×SDS-PAGE sample buffer supplemented with 0.2 M glycine (pH 2) and boiled for 10 min. The cell extract was clarified as above and used directly for SDS-PAGE. The insoluble glycine extracted cell material was washed 3× in 0.5 ml $dH_2O$ and treated with 90% formic acid before SDS-PAGE analysis as previously described [11]. For analysis of acetone-precipitated culture supernatant proteins, 1 ml of T broth culture was clarified as above and 250 ml of culture supernatant was aliquoted and mixed with 1 ml of ice-cold acetone. The precipitated proteins were sedimented (13,200 rpm, 20 min, 4° C.), the supernatant was discarded and the protein pellet was dried for 20 min under vacuum. The pellet was resuspended and boiled for 10 min in 1×SDS-PAGE sample buffer supplemented with 0.2 M glycine (pH 2) before loading onto SDS-PAGE. SDS-PAGE was carried out according to the method of Laemmli [27] with a 5% stacking gel and 12% resolving gel. Proteins separated by SDS-PAGE were electrophoretically transferred to nitrocellulose using an LKB Multiphor II Electrophoresis System (Pharmacia Biotech) and were detected by Western blot techniques using fimbriae- or PT3-specific antisera and goat-anti-rabbit immunoglobulin G-alkaline phosphatase conjugates (Cedarlane) as described previously [11].

Results

Generation of Chimeric *S. enteritidis* Fimbrin Genes

Figure 17C:
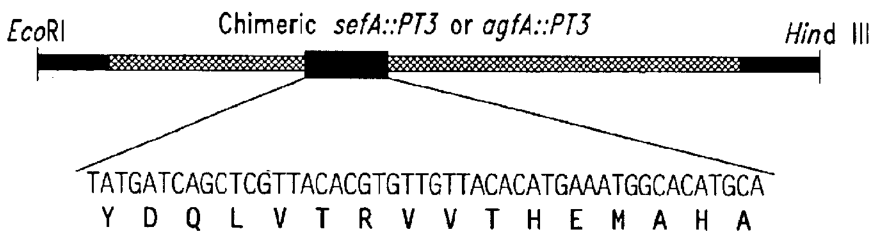
Figure 18A:
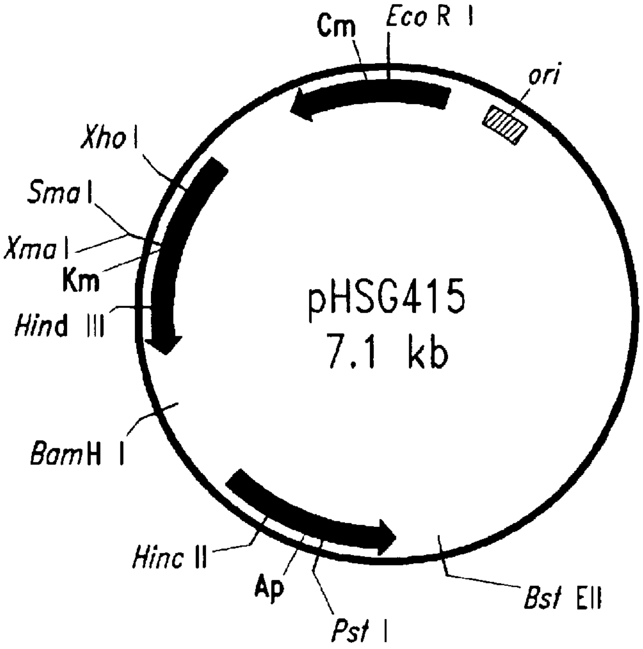
FIG. 18. Generation of *S. enteritidis* strains carrying chimeric fimbrin genes. A. Map of pHSG415 indicating positions of unique restriction endonuclease sites, antibiotic resistance genes (black arrows) and temperature-sensitive origin of replication (ori). Figure adapted from [20]. B. Gene replacement strategy (shown for sefA::PT3). Transformed *S. enteritidis* was grown at 42° C. with selection pressure to induce a single crossover event and subsequent integration of pHSSP10 into the chromosome. Plasmid cointegrates were grown at 28° C. without selection pressure to induce a second crossover event and loss of the pHSG415 sequence, resulting in one of two possibilities: 1) wild-type fimbrin gene or 2) chimeric fimbrin gene.

The *S. enteritidis* 3b fimbrin genes, sefA and agfA were chosen as target DNA sequences to receive a site-specific epitope replacement. The two-step overlap extension PCR method of Horton et al. [22] was used (FIGS. 17A, B) to replace 48 bp of the fimbrin gene with 48 bp encoding the PT3 T cell epitope from *L. major* (FIG. 17C). The PCR-generated genes encoded chimeric SefA and AgfA proteins carrying the PT3 epitope within specific regions of the mature protein (residues 18–33 in SefA and residues 111–126 in AgfA). The resultant sefA::PT3 and agfA::PT3 PCR products were sequenced to confirm the fidelity of PCR and were cloned into pHSG415 (FIG. 18A) to generate recombinant temperature-sensitive plasmids pHSSP10 and pHSAP7, respectively (Table 6).

Gene Replacement in *S. enteritidis.*

Figure 18B:
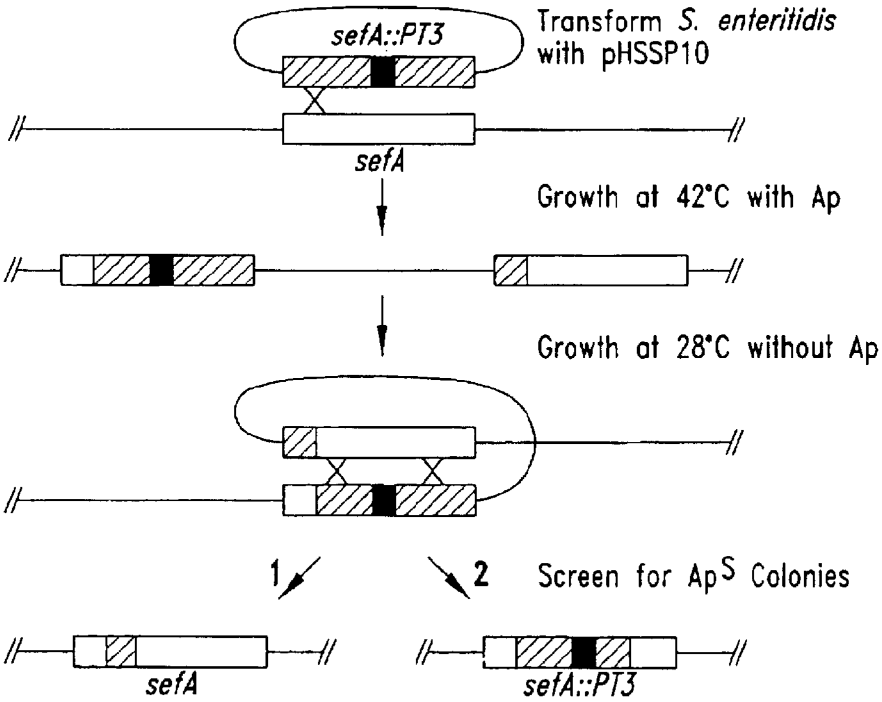

The recombinant temperature-sensitive pSC101-derivative plasmids, pHSSP10 and pHSAP7, were used to replace the native genes in *S. enteritidis* 3b (FIG. 18B). Cells were transformed with pHSSP10 or pHSAP7 and directly plated on selective media (LB/Ap) at the non-permissive temperature (42° C.), but virtually no plasmid cointegrates were obtained. Therefore, cells were grown 24 h in liquid media (TFB/Ap) and transferred five times into fresh media for a total growth period of 120 h before plating on LB/Ap. Of the 50 isolated colonies picked for both pHSSP10 and pHSAP7, 100% of colonies were identified by PCR to contain an integrated plasmid. Three pHSSP10 cointegrate colonies and four pHSAP7 cointegrate colonies were then selected and grown at the permissive temperature of 28° C. in liquid media (TFB) without Ap selection pressure for 24 h and transferred three times into fresh media for a total growth period of 72 h. Dilution plating of these final colonies resulted in the same number of CFU on both LB and LB/Ap plates, suggesting that the majority of cells were still $Ap^R$ (42° C.). However, after an additional growth period of 48 h (120 h total) at 28° C., a high percentage of $Ap^S$ colonies was obtained. 184 isolated colonies were picked from each cointegrate culture, yielding 65%, 55%, and 5% $Ap^S$ from the three pHSSP10 cointegrates, and 27%, 15%, 10% and 9% $Ap^s$ from the four pHSAP7 cointegrates (Table 8). pHSSP10 and pHSAP7 cointegrate colonies were also grown at the non-permissive temperature (42° C.) without Ap selection pressure (120 h). In contrast to the cultures grown at 28° C., no $AP^S$ colonies were obtained.

TABLE 8

| Efficiency of sefA::PT3 and agfA::PT3 gene replacement in *S. enteritidis*. | | | |
|---|---|---|---|
| Plasmid cointegrate colonies | $Ap^S$ colonies[a] # | Chimeric gene % | replacements (%) |
| pHSSP10 | | | |
| Isolate #1 | 119 | 65 | 33[b] |
| Isolate #2 | 8 | 4 | 2[b] |
| Isolate #19 | 101 | 55 | 23[b] |
| pHSAP7 | | | |
| Isolate #2 | 18 | 10 | 7[c] |
| Isolate #3 | 28 | 15 | 10[c] |
| Isolate #9 | 49 | 27 | 4[c] |
| Isolate #10 | 17 | 9 | 8[c] |

[a]184 individual colonies picked in total.
[b]Frequency of sefA::PT3 containing *S. enteritidis* estimated by preliminary PCR results.
[c]Frequency of agfA::PT3 containing *S. enteritidis* estimated by CR binding morphology (TCR).

Genetic Analysis of *S. enteritidis* Strains Containing Chimeric sefA::PT3 or agfA::PT3 Fimbrin Genes To identify *S. enteritidis* strains containing the chimeric sefA::PT3 gene, twenty-eight of the final $Ap^S$ colonies were chosen and analyzed by PCR. Sixteen colonies were identified as having the PT3 DNA sequence within sefA and all twenty-eight colonies were negative for the pSC101 ori sequence found in pHSG415. Furthermore, PCR products were the same size as PCR products of sefA from *S. enteritidis* 3b indicating that no extra plasmid sequence was inserted in this region. Four *S. enteritidis* strains were further analyzed by Southern blotting using DNA probes specific for the PT3 DNA sequence, the region within sefA replaced by the PT3 DNA sequence, the region in sefA 3' to the PT3 insertion site, or the entire EcoRI and HindIII digested pHSG415 plasmid sequence. These data confirmed the PCR results; two of the strains contained sefA::PT3, two strains contained wild-type sefA, and all four strains did not contain any pHSG415 plasmid sequence. Final confirmation of the genotype of these four strains was obtained by DNA sequencing (see Materials and Methods), proving that all four strains contained the correct, predicted gene sequences.

To identify *S. enteritidis* strain containing the chimeric agfA::PT3 gene; five of the final $Ap^S$ colonies were chosen and were analyzed by PCR. Three strains were identified as having the PT3 DNA sequence within agfA and all five strains were negative for the pSC101 ori sequence as above. PCR products from each strain were the same size as PCR products of agfA from *S. enteritidis,* indicating that there was no additional plasmid sequence inserted in this region. Final confirmation of the genotypes of these strains was obtained by DNA sequencing proving that three strains contained agfA::PT3 and two strains contained wild-type agfA. Thus, these data confirmed the creation of *S. enteritidis* strains containing chimeric sefA::PT3 or agfA::PT3 fimbrin genes by precise recombination events.

Plasmid-based Expression of sefA::PT3 and agfA::PT3 in *E. coli*

Figure 19A:
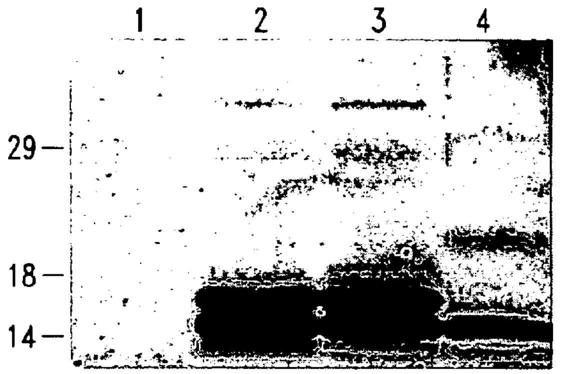
FIG. 19. Western blot analysis to detect expression of chimeric sefA::PT3 and agfA::PT3 in *E. coli*. A. Whole cell lysates of *E. coli* XL-1 Blue harboring pGP1-2 with pTZ18R (lane 1), pTZSef (lane 2), and pTZSP10 (lane 3) reacted with anti-SEF14 and -SEF21 immune serum. Purified SEF14 is represented in lane 4. B. Whole cell lysates of *E. coli* XL-1 Blue harboring pGP1-2 and pTZ18R (lanes 2 and 5), pTZAgf (lanes 3 and 6), or pTZAP7 (lanes 4 and 7) with (+FA) or without (–FA) formic acid treatment reacted with immune sera raised to SEF 17. Lane 1 contains FA treated, purified, thin aggregative fumbriae. The sizes (kDa) of the molecular mass markers are indicated on the left.

To ensure that the chimeric genes used for gene replacement in *S. enteritidis* could be readily transcribed and translated into protein, these genes were expressed in *E. coli* XL-1 Blue utilizing T7 RNA polymerase [44]. Expression of the sefA and sefA::PT3 genes from pTZSef and pTZSP10 was demonstrated by Western blot analysis (FIG. 19A). Both the recombinant SefA::PT3 proteins and wild-type SefA proteins were expressed at comparable levels (FIG. 19A, lanes 2 and 3) and two distinct immunoreactive protein bands (14 kDa and 16–17 kDa) were seen in each lane. The larger protein was thought to be unprocessed wild-type or chimeric SefA possessing the 22-amino acid signal sequence as observed previously [37]. The smaller protein was identified as the mature form of the fimbrin, since the band co-migrated with SefA from purified SEF14 (FIG. 19A, lane 4). Repeat of these blots with PT3-specific immune serum did not reveal either the 14 or 16 kDa protein band in lane 3, suggesting that the PT3 epitope was inaccessible or not exposed on the surface of the chimeric SefA::PT3 protein.

Figure 19B:
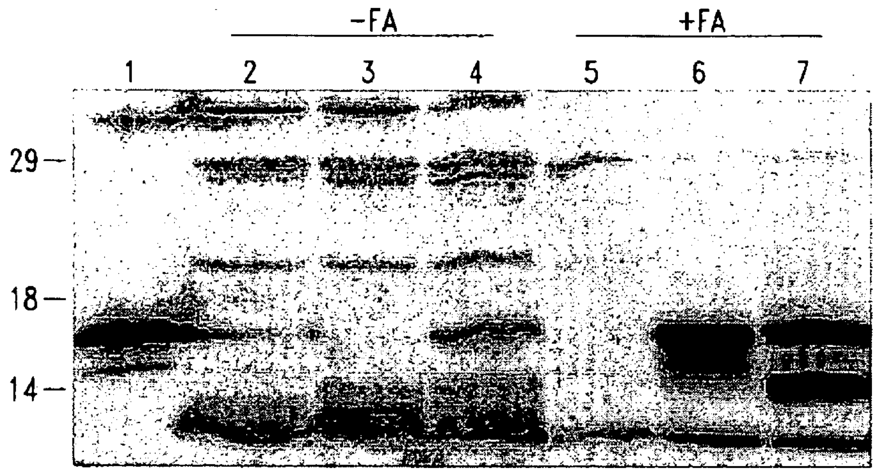

Western blotting also showed expression of the agfA and agfA::PT3 genes from pTZAgf and pTZAP7 in *E. coli* (FIG. 19B). Both the recombinant AgfA::PT3 proteins and wild-type AgfA proteins were observed in SDS-PAGE sample buffer-glycine-insoluble material from whole cells treated with formic acid (FIG. 19B, lanes 5 and 6). Both were expressed at comparable levels and were the same size as mature AgfA from purified thin aggregative fimbriae (17 kDa; FIG. 19B, lane 1), although a second 10 kDa band was seen for AgfA::PT3 (FIG. 19B, lane 6), suggesting that some degradation had occurred. AgfA was not detected in SDS-PAGE sample buffer-glycine extracts of whole cells (FIG. 19B, lane 2). In contrast, AgfA::PT3 was observed in these samples (FIG. 19B; lane 3), indicating that AgfA::PT3 was more soluble than wild-type AgfA. Repeat of these blots with PT3-specific immune serum confirmed that the bands in lanes 3 and 6 were indeed chimeric AgfA::PT3 protein.

Chromosome-based Expression of sefA::PT3 in *S. enteritidis*

Figure 20:
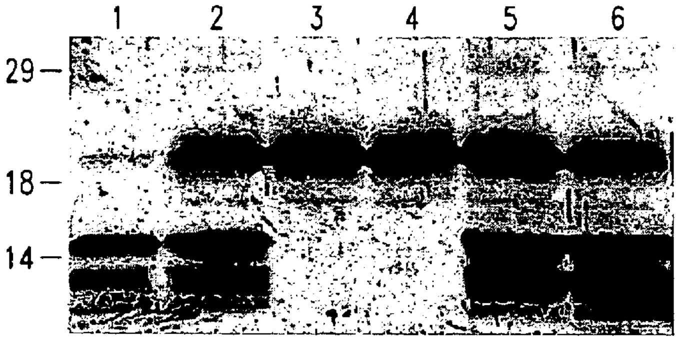
FIG. 20. Western blot analysis of $Ap^S$ *S. enteritidis* strains after sefA::PY3 gene replacement. Whole cell lysates of strains #11 (lane 2), #13 (lane 3), #192 (lane 4), #197 (lane 5), and $W^+$ 3b (lane 6) reacted with anti-SEF14 and -SEF21 immune serum. Purified SEF14 is represented in lane 1. The sizes (kDa) of the molecular mass markers are indicated on the left.

Western blot analysis of the four *S. enteritidis* strains which were shown to contain either sefA::PT3 or sefA after gene replacement is shown in FIG. 20. Strains containing sefA::PT3 (#13 and 192) were negative for the chimeric fimbrin protein SefA::PT3 (FIG. 20, lanes 3 and 4), whereas strains containing sefA (#11 and 197) were positive for the wild-type fimbrin protein SefA (FIG. 20, lanes 2 and 5). All strains were positive for the expression of FimA (21 kDa), the subunit protein of Type 1 fimbriae (FIG. 20, lanes 2–6). The predicted SefA::PT3 protein was not found when Westerns were repeated using a mixture of monoclonal antibodies against SefA. Furthermore, SefA::PT3 was not being secreted into the culture supernatant since trichloroacetic acid (TCA) precipitation of *S. enteritidis* culture supernatant followed by SDS-PAGE/Western blotting did not reveal the recombinant protein. Further Western analysis of strain #13 confirmed that the strain was not producing SefA::PT3 under 16 different growth conditions. Similar results were obtained for all recombinant *S. enteritidis* strains that were PCR-positive for the sefA::PT3 gene. These results demonstrated that *S. enteritidis* strains containing sefA::PT3 were not expressing the chimeric fimbrin protein.

Chromosome-based Expression of agfA::PT3 in *S. enteritidis*

Since *S. enteritidis* 3b forms distinct dark red, aggregative colonies when grown on T media with Congo Red (TCR) and expression of AgfA (thin aggregative fimbriae) is associated with both properties [10], all $Ap^S$ *S. enteritidis* strain obtained after agfA::PT3 gene replacement were streaked onto TCR plates. Based on previously established nomenclature [10], three distinct phenotypes were observed: a) red, aggregative (rough) (RR) colonies, b) orange, non-aggregative (smooth) (OS) colonies, and c) pink, non-aggregative (smooth) (PS) colonies; of 112 $Ap^S$ colonies obtained and characterized, 60 were RR, 39 were OS, and 13 were PS. The two *S. enteritidis* strains shown to contain wild-type agfA sequence (#91 and 104) were identified as being RR like *S. enteritidis* 3b. On the other hand, of the three *S. enteritidis* strains shown to contain agfA::PT3 sequence, two displayed the OS phenotype (#102 and 103), while the third displayed the PS phenotype (#27).

Figure 21A:
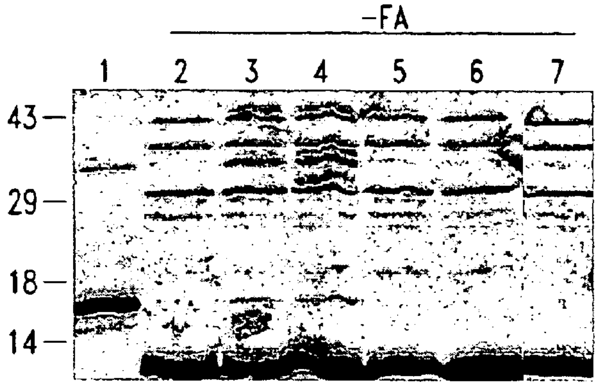
FIG. 21. Western blot analysis of $Ap^S$ *S. enteritidis* strains after agfA::PT3 gene replacement. Whole cell SDS-PAGE sample buffer-glycine extracts of *S. enteritidis* strains #91 (lane 2), #102 (lane 3), #103 (lane 4), #104 (lane 5), $W^+$ 3b (lane 6) and strain #27 (lane 7) without formic acid treatment (A; –FA), and SDS-PAGE sample buffer-glycine insoluble material with formic acid treatment (B; +FA) reacted with immune sera raised to SEF17. Purified SEF17 is represented in lane 1. The sizes (kDa) of the molecular mass markers are indicated on the left.
Figure 21B:
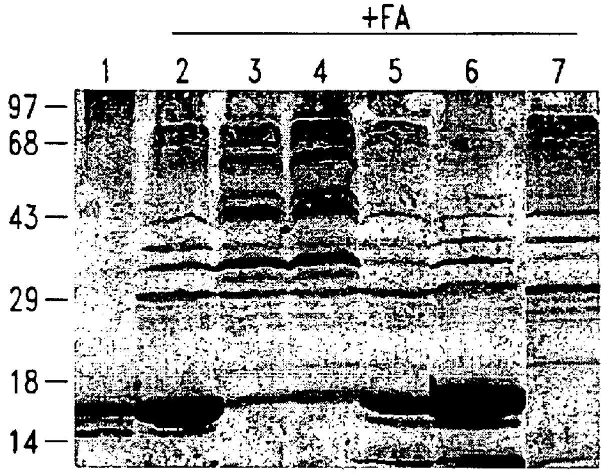

Western blot analysis of these five *S. enteritidis* strains scraped from TCR plates (see Materials and Methods) is shown in FIG. 21. As expected, the two RR strains expressed wild-type AgfA which was only present in SDS-PAGE sample buffer-glycine-insoluble material treated with 90% formic acid (FIG. 21B, lanes 2 and 5), as demonstrated for *S. enteritidis* 3b (FIG. 21B, lane 6). The two OS strains produced an immunoreactive 17 kDa protein (FIG. 21A or B, lanes 3 and 4), indicating they were producing chimeric AgfA::PT3 protein. Furthermore, the 17 kDa protein was present in both SDS-PAGE sample buffer-glycine extracts of whole cells and glycine-insoluble material treated with formic acid, confirming that AgfA::PT3 was more soluble than wild-type AgfA as previously observed in *E. coli* (above). Immunoreactive higher $M_r$ bands representing multimers of AgfA::PT3 were also observed (FIG. 21B, lanes 3 and 4), suggesting that some polymerization of AgfA::PT3 subunits had occurred. In contrast to the OS strains analyzed, the PS strain #27 was negative for AgfA::PT3 when grown on TCR plates (FIGS. 22A or B, lane 7).

Figure 22:
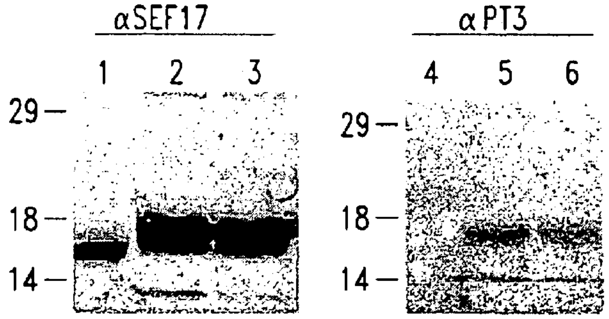
FIG. 22. Western blot analysis of T-broth culture supernatant proteins from *S. enteritidis* strains containing agfA::PT3. SDS-PAGE sample buffer-glycine extracts of acetone-precipitated culture supernatant proteins from *S. enteritidis* strains #102 (lane 2 and 5) and #103 (lane 3 and 6). Purified SEF17 is represented in lanes 1 and 4. Lanes 1–3 were reacted with immune sera raised to whole SEF 17, whereas Lanes 4–6 were reacted with immune sera raised to PT3 peptide. The sizes (kDa) of the molecular mass markers are indicated on the left.

To investigate whether the *S. enteritidis* OS strains were secreting soluble AgfA::PT3 into the media, they were grown in T broth and the culture supernatant proteins were precipitated and analyzed by SDS-PAGE and Western blotting. FIG. 22 represents replicate Western blots of these protein samples boiled in SDS-PAGE sample buffer with glycine, one reacted with immune serum generated against whole SEF17 (FIG. 22, lanes 1–3) and the other reacted with immune serum generated against the PT3 peptide (FIG. 22, lanes 4–6). Both OS strains revealed a soluble immunoreactive 18 kDa protein which was recognized by both SEF17- and PT3-specific antiserum (FIG. 22, lanes 2 and 5, 3 and 6), confirming that they were expressing chimeric AgfA::PT3 and secreting large amounts into the media. Amino-terminal sequencing of the 18-kDa protein band from OS strain #102 yielded the GVVPQ sequence of mature AgfA [11], indicating that the size difference between these protein bands and wild-type AgfA from whole SEF17 (FIG. 22A, lane 1) was not due to a failure to cleave the signal sequence. Analysis of the PS strain under the same conditions revealed a faint immunoreactive band of similar size, suggesting that this strain was also expressing AgfA::PT3, but at a much lower level than the two OS strains. Like the two OS strains, amino terminal sequencing of this protein band yielded a major signal of GVVPQ. These results demonstrated the isolation of two genetically similar *S. enteritidis* strain types containing agfA::PT3 which express the chimeric fimbrin protein at different levels.

The system for chromosomal gene replacement used for creation of *Salmonella* strains containing recombinant agfA was also used for creating *Salmonella* strains containing recombinant sefA. The sefA gene encodes SefA, the major subunit protein for SEF14 fimbriae produced by group D *Salmonella* spp. (Baumler and Heffron, 1995). SEF14 is a thin fimbriae like TAF, but unlike the TAF operon, the SEF14 operon encodes proteins which show homology to chaperone and usher proteins from other fimbrial systems (Clouthier et al., 1993). Therefore, SEF14 is proposed to assemble via the chaperone/usher pathway (Hultgren et al., 1996) and growth of the fimbrial fiber is probably achieved from the base by addition of the subunits from the periplasmic side of the outer membrane (Mol and Oudega, 1996).

SefA as a Carrier of the PT3 Epitope

Figures 23A, 23B:
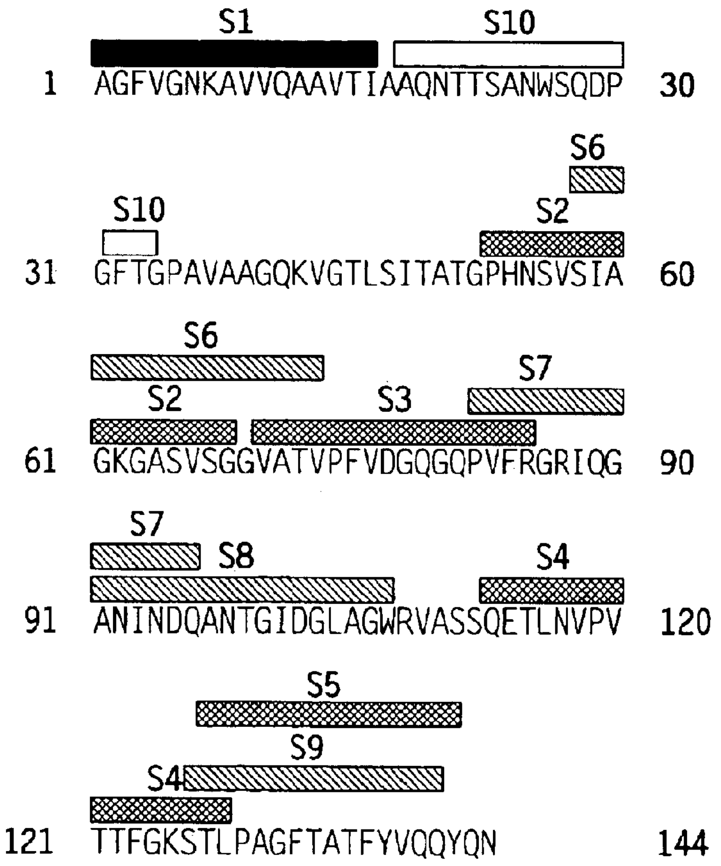
FIG. 23. PT3 epitope replacement in SefA. A. Peptide sequence of the PT3 epitope from GP63 of *Leishmania major* (SEQ ID No: 10) (Jardim et al., 1990). B. Schematic diagram of the mature SefA protein (SEQ ID NO: 46) illustrating the regions replaced by the PT3 epitope sequence; regions S1 to S10 are indicated with the colored boxes above the sequence. Color Code: Black=region S1; Orange=region S10; Blue=regions S2, S3, S4, S5; Green=regions S6, S7, S8, S9.
Figure 24A:
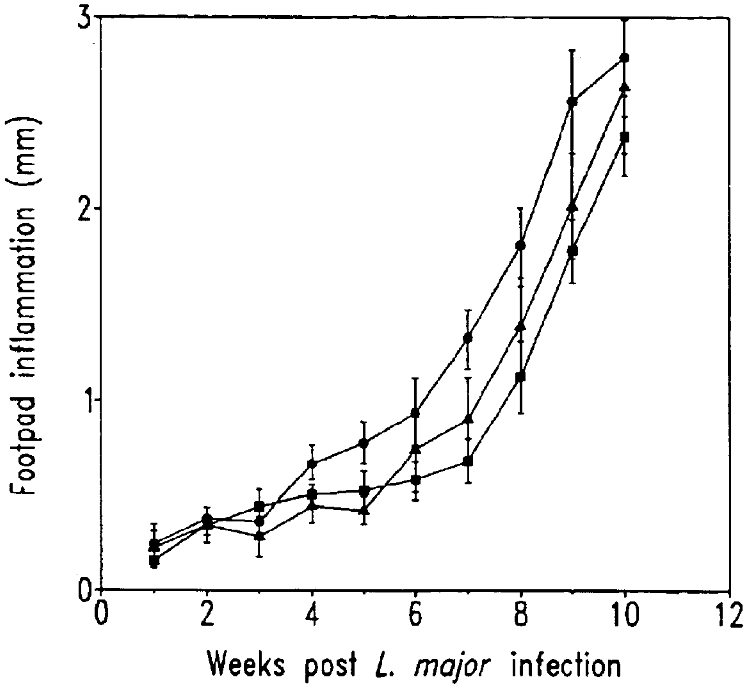
FIG. 24. Footpad inflammation of vaccinated BALB/c mice after *Leishmania major* challenge. Mice were vaccinated with a single oral dose (A, C) of *S. enteritidis* 3b or A4 ($10^5$ organisms/mouse) or PBS alone or two oral doses (B, D) of *S. enteritidis* 3b or A4 ($10^5$ and $10^3$ organisms/mouse) or PBS alone spaced 2 weeks apart. They were challenged with *L. major* in the footpad 6 weeks (A, B; $10^7$ organisms/mouse) or 8 weeks (C, D; $5\times10^6$ organisms/mouse) after first vaccination. Footpad inflammation was measured weekly as the increase in footpad thickness (subtracting the thickness of unifected footpad from that of the infected footpad). Symbols on graphs: (circle) *S. enteritidis* A4 vaccinated mice; (triangle) *S. enteritidis* 3b vaccinated mice; and (square) PBS-vaccinated control mice. Data are means +/– standard errors of the mean (n=5).
Figure 24B:
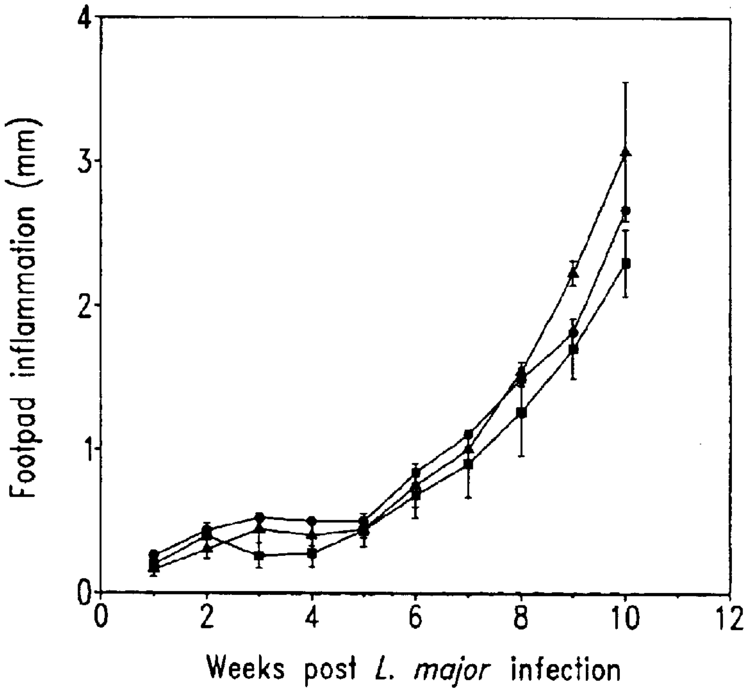
Figure 24C:
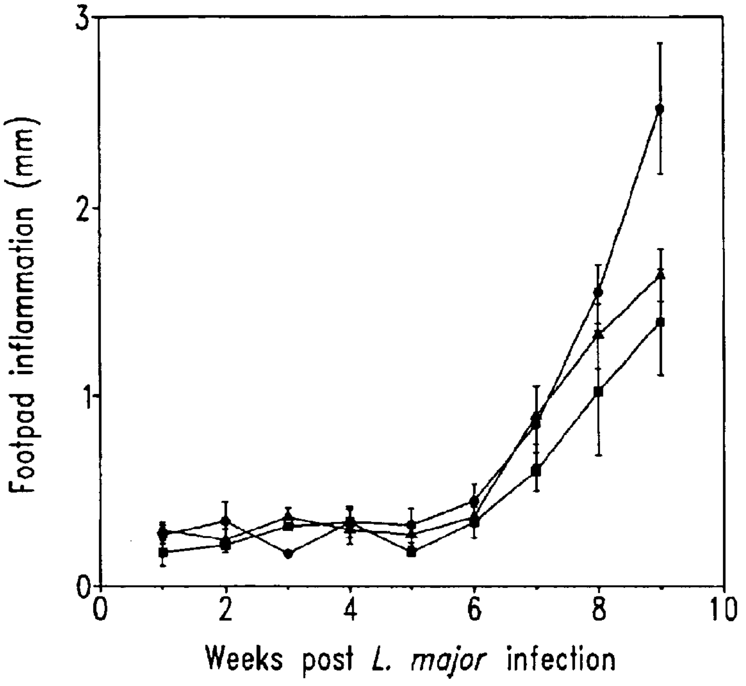
Figure 24D:
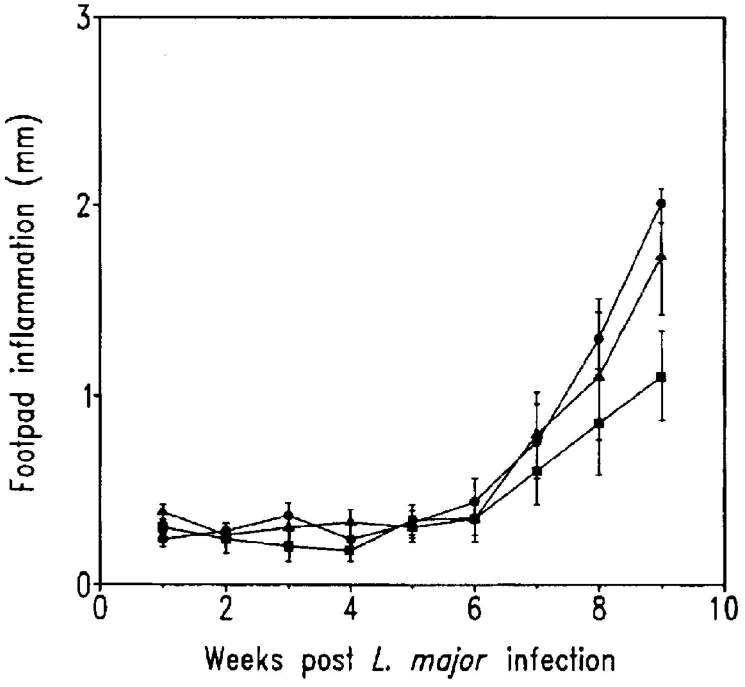

Ten different 16 amino acid segments within SefA were chosen for replacement with the PT3 epitope and are highlighted in FIG. 23. These replacement regions were chosen using several criteria: primary sequence alignment, region S1 (black); hydrophilicity, flexibility and accessibility plots, region S10 (orange); experimentally determined B-cell epitope regions, regions S2, S3, S4, and S5 (blue); and TnphoA mutagenesis data, regions S6, S7, S8 and S9 (green). In total, all 117 of 144 residues within SefA were replaced with the PT3 sequence in at least one of the chimeric fimbrin constructs.

Generation of *S. enteritidis* Strain Containing the sefA::PT3 Genes

All recombinant sefA::PT3 genes were generated by PCR, sequenced and introduced into the chromosome of *S. enteritidis,* replacing the $W^+$ sefA gene, using the procedure described for agfA.

Only *S. enteritidis* Strains Containing sefA::PT3 #1, 2, 4, 5, 6, 8, 9, 10 in the Chromosome were Obtained Western blots were used to analyze *S. enteritidis strains containing sefA::PT*3 in the chromosome. The recombinant *S. enteritidis* strains S1, S2, S4, S5, S6, S8, S9, and S10 were grown on CFA plates at 37° C. for 24 h and were analyzed for production of recombinant SefA proteins containing the PT3 epitope by SDS-PAGE and western blotting.

In contrast to the results with agfA, NO recombinant SefA fimbrin proteins could be detected in any of the recombinant *Salmonella* strains containing recombinant sefA. These data demonstrated that SefA was not a suitable carrier of heterologous (foreign) peptide sequences and could not tolerate substitution of its residues from the N- to C-terminus of the protein.

Since none of the recombinant SefA fimbrin proteins were able to be expressed in *Salmonella*, this provides evidence that fimbriae which assemble via the chaperone/usher pathway would not be good carriers of heterologous (foreign) peptide sequences. In addition, this finding further proves the utility and uniqueness of the AgfA/TAF presentation system described (i.e., the ability of agfA to accept major substitutions throughout its sequence and still have the ability to assemble into fimbrial fibers at the cell surface).

Discussion

The invention described herein provides an efficient and fascile strategy for the replacement of wild-type genes in the *S. enteritidis* chromosome with in vitro-altered versions. This gene replacement method allowed for efficient, site-specific chromosomal gene replacement without the need for selective markers in the target gene(s) or special bacterial strains for recombination, and avoided the introduction of non-target DNA sequences. The method was used to construct *S. enteritidis* strains containing chimeric sefA and agfA fimbrin genes which carry foreign DNA encoding the PT3 epitope from *L. major* . The sefA::PT3 and agfA::PT3 genes presented here represent the first chimeric fimbrin genes reported for the genus *Salmonella.*

The gene replacement method reported in this study employs pHSG415, derived from a temperature-sensitive pSC101 replicon [20]. Although other gene replacement methods using temperature-sensitive pSC101replicons [18, 30] have been reported, their results were less favorable than those reported here. The method of Hamilton et al. [18] results in final strains containing freely replicating plasmids which must be cured before selecting gene replacements, whereas the present method results in a high proportion of final strains which have lost the excised plasmid altogether and can be screened directly by PCR. The method of Link et al. [30] includes the *Bacillus subtilis* sacB system to enable direct selection for excision and loss of integrated plasmids. However, when creating deletion mutants of hdeA in *E. coli* without the use of selectable markers, these authors reported lower frequencies than are reported here (Table 8). In addition, the sacB system is complicated by the frequency of $Suc^R$ revertants [24,26].

A closer look at the properties of pHSG415 can help explain why this gene replacement method is so efficient. In contrast to pSC101, pHSG415 was shown to be extremely unstable in liquid culture in the absence of selection pressure, with as few as 60% of cells carrying the plasmid after 24 hr [5]. These authors speculated that the difference between pSC101 and pHSG415 was due to the absence of most of the par locus in pHSG415. The pSC101 par locus has been very well characterized; it has been shown to alter the binding of proteins within the origin region [23] and thus to enhance DNA replication [32]. In addition, it contains a preferential binding site for DNA gyrase [48] and alters the negative supercoiling of DNA [35]. Through a combination of these effects the par locus promotes partitioning of plasmids to daughter cells at the time of cell division [34]. Due to the deletion of the par locus, pHSG415 is proposed to have a defect in its segregating properties causing unequal partitioning of plasmid molecules to daughter cells at the time of cell division [5]. The present method uses the unstable properties of pHSG415 to advantage, and in the absence of selection pressure, integrated plasmids are lost immediately after the second crossover event or are retained for several generations and then lost. This would explain why an additional growth period of 48 hours (after the initial 72 hours) was sufficient to result in a high percentage of $Ap^S$ colonies when grown at 28° C. Thus, it is possible to replace sefA and agfA in the chromosome of a wild-type strain of *S. enteritidis* without any antibiotic resistance markers in the target genes at an efficiency of 30% and 10%, respectively.

It is possible that the high gene replacement frequencies observed simply reflect the relative ease of sefA or agfA replacement. However, a recent study by Edwards et al. [14] reported the replacement of sefA or agfA within *S. enteritidis* at lower frequencies than reported here, even with the use of a $Km^R$ marker in the recombinant genes. This supports the utility of the present method and demonstrates that the high replacement frequencies reported here are not simply due to the ease of sefA or agfA replacement. Therefore, this method has broad application and appeal for gene replacement in *Salmonella* and other enteric bacteria capable of supporting the replication of pSC101-derived plasmids. In addition, these results suggest that the use of similar "unstable" plasmids in other organisms could represent a more generalized mutagenesis strategy.

The sefA::PT3 and agfA::PT3 genes presented here both carry a foreign DNA segment encoding PT3, a $Th_1$-restricted T cell epitope comprising residues 154–168 from the GP63 protein of *L. major* [25]. This epitope was chosen because it was shown to be immunoprotective in Balb/c mice [41] and because studies with *Salmonella* vaccine strains expressing GP63 have demonstrated that oral vaccination against *Leishmania* infection is possible [33]. Therefore, PT3 is a good candidate for developing and testing a heterologous fimbrial vaccine system in *Salmonella*. The subunit proteins of SEF14 and SEF17 fimbriae, SefA and AgfA, respectively, were chosen as the carriers of PT3 because they can be expressed at high levels and are surface-exposed [8,11], properties proven to be advantageous for other heterologous epitope presentation systems [28]. Moreover, SEF14 and SEF17 represent distinct classes of fimbriae in *S. enteritidis* 3b [31] and differ in their primary fimbrin sequence, probable tertiary structure, expression patterns, mode of assembly, and biochemical properties.

Two *S. enteritidis* strains that contained sefA::PT3 were identified, genetically characterized and analyzed for expression of the chimeric fimbrin proteins. While SefA::PT3 protein was produced in *E. coli*, indicating that the sefA::PT3 gene construct had the correct coding sequence, the chimeric protein could not be detected in *S. enteritidis*. This could be due to a number of factors: alteration in the DNA topology of the chromosome effecting transcription initiation; production of an unstable RNA transcript; or expression of a significantly misfolded and rapidly degraded protein, due to the positioning of PT3 in the N-terminal region of SefA, a region important for dimerization of wild-type SefA subunits [6]. Experiments to identify more permissible sites for foreign epitope replacement within SefA are currently underway.

Three *S. enteritidis* strain that contained agfA::PT3 were identified, genetically characterized and analyzed for expression of the chimeric fimbrin proteins. In contrast to the sefA::PT3 mutants, two of these strains were shown to produce the chimeric fimbrin protein at high levels. These strains displayed a distinct orange, non-aggregative (smooth) (OS) phenotype when plated on TCR medium, in contrast to the red, aggregative (rough) (RR) phenotype displayed by *S. enteritidis* 3b. Closer analysis of the AgfA::PT3 protein demonstrated that it had unexpected properties; whereas wild-type AgfA required pre-treatment in 90% formic acid to enter polyacrylamide gels, the chimeric AgfA::PT3 protein was readily seen by SDS-PAGE without formic acid treatment. The third strain containing AgfA::PT3 had properties quite different than the other two. It produced much lower levels of chimeric agfA::PT3 protein under the growth conditions tested and gave a third distinct phenotype when plated on TCR medium, displaying pink, non-aggregative (smooth) (PS) colonies. This PS strain was shown to contain no sequence errors within agfA::PT3 and surrounding region (950 bp), thereby suggesting that gene replacement within the agfBAC operon of *S. enteritidis* can somehow affect fimbriae biosynthesis. The PS phenotype was similar to that previously reported for SEF17-deficient TnphoA mutants of *S. enteritidis* 3b [10]. Römling et al. [38] observed similar pink, smooth colonies for *S. typhimurium* on CR media and showed that a single base pair change in the agfD promoter sequence was responsible for the mutant phenotype and lack of AgfA production. Allen-Vercoe et al. [1] have also recently described AgfA *S. enteritidis* mutants with a pink, smooth phenotype on CR media and have characterized these strains as expressing a new, as yet undetermined fimbrial type. In light of these recent findings, the nature of the differences between the OS and PS agfA::PT3 strains are currently under investigation.

SefA::PT3 and agfA::PT3 represent the first chimeric fimbrin genes reported for the genus *Salmonella*. These genes were replaced at the sites in the chromosome originally occupied by the wild-type fimbrin genes so as to maintain the appropriate relationship with any potential upstream regulatory sequences. Thus, the recombinant *S. enteritidis* strains that have been created are genetically identical to the $W^+$ strain with the exception of the 48 bp foreign DNA sequence. The gene replacement strategy presented allows for the rapid generation of similar *S. enteritidis* vaccine strains without the need for antibiotic resistance markers and/or the screening of thousands of colonies for a "rare" double crossover event. Strains created in this manner can then be used in future vaccine studies without the complications associated with extraneous DNA elements.

References Cited in Example 2

Bäumler A. J. et al. (1995). *J. Bacteriol.,* 177, 2087–2097.

Clouthier S. C. et al. (1993). *J. Bacteriol.,* 175, 2523–2533.

[1] Allen-Vercoe E., Dibβ-Fuller M., Thorns C. J., Woodward M. J. SEF17 fimbriae are essential for the convoluted colonial morphology of *Salmonella enteritidis. FEMS Microbiol. Lett.* 1997, 153, 33–42.

[2] Bakker D., van Zijderveld F. G., van der Veen S., Oudega B., de Graaf F. K. K88 fimbriae as carriers of heterologous antigenic determinants. *Microb. Pathog.* 1990, 8, 343–352.

[3] Bäumler A. J., Heffron F. Identification and sequence analysis of lpfABCDE, a putative fimbrial operon of *Salmonella typhimurium. J. Bacteriol.* 1995, 177, 2087–2097.

[4] Cárdenas L., Clements J. D. Stability, immunogenicity and expression of foreign antigens in bacterial vaccine vectors. *Vaccine* 1993, 11, 126–135.

[5] Caulcott C. A., Dunn A., Robertson H. A., Cooper N. S., Brown M. E., Rhodes P. M. Investigation of the effect of growth environment on the stability of low-copy-number plasmids in *Escherichia coli. J. Gen. Microbiol.* 1987, 133, 1881–1889.

[6] Clouthier S. C., Collinson S. K., Lippert D., Ausio J., White A. P., Kay W. W. Periplasmic and fimbrial SefA from *Salmonella enteritidis. Biochem. Biophys. Acta* 1998, 1387, 355–368.

[7] Clouthier S. C., Collinson S. K., White A. P., Banser P. A., Kay W. W. tRNA$^{Arg}$ (fimU) and Expression of SEF14 and SEF21 in *Salmonella enteritidis. J. Bacteriol.* 1998, 180, 840–845.

[8] Clouthier S. C., Müller K.-H., Doran J. L., Collinson S. K., Kay W. W. Characterization of three fimbrial genes, sefABC, of *Salmonella enteritidis. J. Bacteriol.* 1993, 175, 2523–2533.

[9] Collinson S. K., Clouthier S. C., Doran J. L., Banser P. A., Kay W. W. *Salmonella enteritidis* agfBAC operon encoding thin, aggregative fimbriae. *J. Bacteriol.* 1996, 178, 662–667.

[10]Collinson S. K., Doig P. C., Doran J. L., Clouthier S., Trust T. J., Kay W. W. Thin, aggregative fimbriae mediate binding of *Salmonella enteritidis* to fibronectin. *J. Bacteriol.* 1993, 175, 12–18.

[11]Collinson S. K., Emödy L., Müller K.-H., Trust T. J., Kay W. W. Purification and characterization of thin, aggregative fimbriae from *Salmonella enteritidis. J. Bacteriol.* 1991, 173, 4773–4781.

[12]Coulson N. M., Fulop M., Titball R. W. Effect of different plasmids on colonization of mouse tissues by the aromatic amino acid dependent *Salmonella typhimurium* SL 3261. *Microb. Pathog.* 1994, 16, 305–311.

[13]Curtiss III R., Kelly S. M., Tinge S. A., Tacket C. O., Levine M. M., Srinivasan J., Koopman M. Recombinant *Salmonella* vectors in vaccine development. *Dev. Biol. Stand.* 1994, 82, 23–33.

[14]Edwards R. A., Keller L. H., Schifferli D. M. Improved allelic exchange vectors and their use to analyze 987P fimbria gene expression. *Gene* 1998, 207, 149–157.

[15]Evans D. G., Evans D. J. J., Tjoa W. Hemagglutination of human group A erythrocytes by enterotoxigenic *Escherichia coli* isolated from adults with diarrhea: correlation with colonization factor. *Infect. Immun.* 1977, 18, 330–337.

[16]Feutrier J., Kay W. W., Trust T. J. Purification and characterization of fimbriae from *Salmonella enteritidis. J. Bacteriol.* 1986, 168, 221–227.

[17]Flynn J. L., Weiss W. R., Norris K. A., Seifert H. S., Kumar S., So M. Generation of a cytotoxic T-lymphocyte response using a *Salmonella* antigen-delivery system. *Mol. Microbiol.* 1990, 4, 2111–2118.

[18]Hamilton C. M., Aldea M., Washburn B. K., Babitzke P., Kushner S. R. New method for generating deletions and gene replacements in *Escherichia coli. J. Bacteriol.* 1989, 171, 4617–4622.

[19]Harlow E., Lane D. Antibodies: a laboratory manual. Cold Spring Harbor, N.Y.: Cold Spring Harbor Laboratory, 1988.

[20]Hashimoto-Gotoh T., Franklin F. C. H., Nordheim A., Timmis K. N. Specific-purpose plasmid cloning vectors: I. Low copy number, temperature-sensitive, mobilization defective pSC101-derived containment vectors. Gene 1981, 16, 227–235.

[21]Hone D., Attridge S., van den Bosch L., Hackett J. A chromosomal integration system for stabilization of heterologous genes in *Salmonella* based vaccine strains. *Microb. Pathog.* 1988, 5, 407–418.

[22]Horton R. M., Hunt H. D., Ho S. N., Pullen J. K., Pease L. R. Engineering hybrid genes without the use of restriction enzymes: gene splicing by overlap extension. *Gene* 1989, 77, 61–68.

[23]Ingmer H., Cohen S. N. The pSC101 par locus alters protein-DNA interactions in vivo at the plasmid replication origin. *J. Bacteriol.* 1993, 175, 6046–6048.

[24]Jäger W., Schäfer A., Pühler A., Labes G., Wohlleben W. Expression of the *Bacillus subtilis* sacB gene leads to sucrose sensitivity in the gram-positive positive bacterium *Corynebacterium glutamicum* but not in *Streptomyces lividans. J. Bacteriol.* 1992, 174, 5462–5465.

[25]Jardim A., Alexander J., Teh H. S., Ou D., Olafson R. W. Immunoprotective *Leishmania major* synthetic T cell epitopes. *J. Exp. Med.* 1990, 172, 645–648.

[26]Kaniga K., Delor I., Cornelis G. R. A wide-host-range suicide vector for improving reverse genetics in Gram-negative bacteria: inactivation of the blaA gene of *Yersinia enterocolitica. Gene* 1991, 109, 137–141.

[27]Laemmli U. K. Cleavage of structural proteins during the assembly of the head of bacteriophage T4. *Nature* (London) 1970, 227, 680–685.

[28]Levi R., Arnon R. Synthetic recombinant influenza vaccine induces efficient long-term immunity and cross-strain protection. *Vaccine* 1996, 14, 85–92.

[29]Levine M. M., Galen J., Barry E., Noriega F., Chatfield S., Sztein M., Dougan G., Tacket C. Attenuated *Salmonella* as live oral vaccines against typhoid fever and as live vectors. *J. Biotech.* 1996, 44, 193–196.

[30]Link A. J., Phillips D., Church G. M. Methods for generating precise deletions and insertions in the genome of wild-type *Escherichia coli*: application to open reading frame characterization. *J. Bacteriol.* 1997, 179, 6228–6237.

[31]Low D., Braaten B., van der Woude M. Fimbriae. In: *Escherichia coli and Salmonella.* (Ed Neidhardt, F. C.). American Society for Microbiology, Washington D.C., 1996, pp. 146–157.

[32]Manen D., Goebel T., Caro L. The par region of pSC101 affects plasmid copy number as well as stability. *Mol. Microbiol.* 1990, 4, 1839–1846.

[33]McSorley S. J., Xu D., Liew F. Y. Vaccine efficacy of *Salmonella strains expressing glycoprotein* 63 with different promoters. Infect. Immun. 1997, 65, 171–178.

[34]Meacock P. A., Cohen S. N. Partitioning of bacterial plasmids during cell division: a cis-acting locus that accomplishes stable plasmid inheritance. *Cell* 1980, 20, 529–542.

[35]Miller C. A., Beaucage S. L., Cohen S. N. Role of DNA superhelicity in partitioning of the pSC101 plasmid. *Cell* 1990, 62, 127–133.

[36]Mol O., Oudega B. Molecular and structural aspects of fimbriae biosynthesis and assembly in *Escherichia coli. FEMS Microbiol. Rev.* 1996, 19, 25–52.

[37]Müller K.-H., Trust T. J., Kay W. W. Fimbriation genes in *Salmonella enteritidis. J. Bacteriol.* 1989, 171, 4648–4654.

[38]Römling U., Sierralta W. D., Eriksson K., Normark S. Multicellular and aggregative behaviour of *Salmonella typhimurium* strains is controlled by mutations in the agfD promoter. *Mol. Microbiol.* 1998, 28, 249–264.

[39]Rosner J. L. Formation, induction and curing of bacteriophage P1 lysogens. *Virology* 1972, 48, 679.

[40]Sambrook J., Fritsch E. F., Maniatis T. Molecular Cloning: A Laboratory Manual. Cold Spring Harbor, N.Y., Cold Spring Harbor Laboratory, 1989.

[41]Spitzer N., Jardim A., Lippert D., Olafson R. W. Long term protection of mice against *Leishmania major* with a synthetic peptide vaccine. Vaccine 1998, In press.

[42]Stentebjerg-Olesen B., Pallesen L., Jensen L. B., Christiansen G., Klemm P. Authentic display of a cholera toxin epitope by chimeric type 1 fimbriae: effects of insert position and host background. *Microbiology* 1997, 143, 2027–2038.

[43]Strugnell R. A., Maskell D., Fairweather N., Pickard D., Cockayne A., Penn C., Dougan G. Stable expression of foreign antigens from the chromosome of *Salmonella typhimurium* vaccine strains. *Gene* 1990, 88, 57–63.

[44]Tabor S., Richardson C. C. A bacteriophage T7 RNA polymerase/promoter system for controlled exclusive expression of specific genes. *Proc. Natl. Acad. Sci. USA* 1985, 82, 1074–1078.

[45]van Die I., van Oosterhout J., van Megan I., Bergmans H., Hoekstra W., Enger-Valk B., Barteling S., Mooi F. Expression of foreign epitopes in P-fimbriae of *Escherichia coli. Mol. Gen. Genet.* 1990, 222, 297–303.

[46]Verma N. K., Ziegler H. K., Stocker B. A. D., Schoolnik G. K. Induction of a cellular immune response to a defined T-cell epitope as an insert in the flagellin of a live vaccine strain of *Salmonella. Vaccine* 1995, 13, 235–244.

[47]Verma N. K., Ziegler H. K., Wilson M., Khan M., Safley S., Stocker B. A. D., Schoolnik G. K. Delivery of class I and class II MHC-restricted Tell epitopes of listeriolysin of *Listeria monocytogenes* by attenuated *Salmonella. Vaccine* 1995, 13, 142–150.

[48]Wahle E., Kornberg A. The partition locus of plasmid pSC101 is a specific binding site for DNA gyrase. *EMBO J.* 1988, 7, 1889–1895.

[49]Xu D., McSorley S. J., Chatfield S. N., Dougan G., Liew F. Y. Protection against *Leishmania major* infection in genetically susceptible Balb/c mice by GP63 delivered orally in attenuated *Salmonella typhimurium* ($AroA^-$ $AroD^-$). *Immunology* 1995, 85, 1–7.

EXAMPLE 3

Demonstration of the Vaccine Potential of *S. enteritidis* Displaying Chimeric Fimbrins Containing a T Cell Epitope from *Leishmania major*

Introduction

Several strains of *S. enteritidis* carrying chromosomal chimeric fimbrin genes (agfA::PT3, above) were developed. The corresponding chimeric AgfA::PT3 proteins were expressed and assembled into SEF17 fimbriae as described above. These strains display the PT3 T cell epitope from the gp63 protein of *L. major* in large quantities at the *S. enteritidis* cell surface. Recent work with the PT3 epitope proved that a single immunization of peptide in adjuvant was able to protect BALB/c mice against challenge with *L. major* (Spitzer et al., 1998). Thus, the *S. enteritidis* strains containing agfA::PT3 genes are promising candidates for the protection of BALB/c mice against *L. major* infection.

Infection of BALB/c mice with *L. major* has been very well studied. The immune response generated in BALB/c mice in response to *L. major* infection is reviewed in Locksley et al. (1999). To summarize, BALB/c mice are highly susceptible to *L. major* infection, whereas most other inbred mouse strains develop immunity and are able to control infection. Upon infection of BALB/c mice with *L. major* the majority of parasite-specific CD4 T cells (T helper cells or Th) generated are of the type 2 variety (Th2 cells) which push the immune response toward phagocyte-independent immunity and antibody production. In contrast, mice that resist *L. major* infection generate a majority of Th1 cells which are required for activation of phagocyte-dependent immunity or cell-mediated immunity. The balance between susceptibility and resistance to *L. major* infection seems to rely on the relative numbers of these two Th subspecies. It should be noted that the PT3 epitope was demonstrated to specifically induce proliferation of CD4 T cells of the Th1 subset (Jardim, 1994).

Materials and Methods

Animals

Inbred BALB/c mice were initially obtained from The Jackson Laboratory (Bar Harbor, Me.) and bred at the McGill Research Institute (Montréal, Québec). Mice used for *L. major* vaccine trial were 8–10 weeks of age.

Bacterial Strains, Parasites, Media and Growth Conditions

*S. enteritidis* 27655 strain 3b has been previously described (Feutrier et al., 1986). *S. enteritidis* strains A4, A5, and A8 were described above. *Leishmania major* carrying a reporter gene (Ha et al., 1996) to simplify measurement of parasite number was used as the virulent challenge strain.

For analysis of fimbrial production, *S. enteritidis* A4, A5, and A8 were grown in 10 ml T broth (Collinson et al., 1991) or trypticase soy broth (TSB; Becton-Dickinson) statically or 200 rpm for 6, 24 or 48 h at 37 C. To prepare *S. enteritidis* for immunization of BALB/c mice, cells were grown in 5 ml TSB for 6 h at 37° C., 250 rpm and 100 μl used to inoculate 100 ml T broth and incubated for a further 48 h at 37° C. and 200 rpm. Cell density was determined by dilution plating onto trypticase soy agar (TSA). Subsequently, cultures were diluted to appropriate cell density in phosphate. buffered saline (PBS) and used for immunization of BALB/c mice.

*L. major* was grown in SDM-79 medium (Brun and Sch önenberger, 1979) supplemented with 10% fetal bovine serum and 5 μg/mL hemin.

Preparation of Protein Samples For SDS-PAGE

*S. enteritidis* A4, A5, A8 and 3b broth cultures were normalized to 1 $A_{600}$ and 1 ml cells were harvested, resuspended in 200 μl of SDS-PAGE sample buffer supplemented with 0.2 M glycine (pH 2), and boiled for 10 min. This cell extract was clarified by spinning in a microcentrifuge (13,200 rpm, 5 min.) and used directly for SDS-PAGE analysis. The insoluble glycine-extracted cell material recovered by centrifugation was washed with $dH_2O$ and treated with 90% formic acid (Collinson, 1991; Collinson, 1993) before analysis by SDS-PAGE.

Gel Electrophoresis and Immunoblotting Procedures

SDS-PAGE was carried out according to the method of Laemmli (1970) with a 5% stacking gel and 12% resolving gel. Proteins separated by SDS-PAGE were electrophoretically transferred to nitrocellulose using an LKB Multiphor II Electrophoresis System (Pharmacia Biotech). Proteins were detected by Western blot techniques using SEF17-specific immune serum and goat-anti-rabbit immunoglobulin G-alkaline phosphatase conjugates (Cedarlane) as described previously (Collinson et al., 1991).

Vaccination of Mice with *S. enteritidis*

BALB/c mice were deprived of food 16–18 h and water 1 h before vaccination. Immediately before administration of *Salmonella* or PBS, mice were administered 50 $\mu$l of 1% sodium bicarbonate orally. Two groups of 15 mice (males and females) were each then immunized orally with $10^5$ CFU of *S. enteritidis* A4 or 3b in 200 $\mu$l PBS. Two groups of control animals received 200 $\mu$l PBS only. Two weeks after the first vaccination, one *S. enteritidis* 3b group received a second dose of $10^3$ *S. enteritidis* 3b whole cells in 200 $\mu$l PBS, one *S. enteritidis* A4 group received a second dose of $10^3$ *S. enteritidis* A4 whole cells in 200 $\mu$l PBS, and one control group received 200 $\mu$l PBS only. All oral inoculations were carried out with a stainless steel gavage needle without an anaesthetic. Mice were monitored daily for signs of infection.

Challenge with *L. major*

5 vaccinated mice from each of the six vaccinated groups were challenged with $10^7$ live *L. major* in 50 $\mu$l of PBS four or six weeks after the first vaccination or with $5\times10^6$ live *L. major* in 50 $\mu$l of PBS eight weeks after first vaccination by subcutaneous injection in the right hind footpad. Infected footpad and noninfected footpad sizes were measured each week after *L. major* infection until the end of the experiment using DigiMax electronic calipers. The net value for footpad inflammation (in millimeters) was calculated by subtracting the diameter of the noninfected footpad from the diameter of the infected footpad. Ulceration of infected footpads was also noted.

At the end of the experiment, all mice were sacrificed by overexposure to $CO_2$. Blood was collected by cardiac puncture and the spleen was removed. In addition, the popliteal ganglion from the right leg, the large lobe of the liver, the infected and noninfected hind paws were removed, frozen in liquid nitrogen and stored at $^-80°$ C. until further analysis. The mouse blood samples were stored at 4° C. for 24 h, clotted material was spun down for 20 min at 13,200 rpm, and the immune serum was removed and stored at $^-20°$ C. until use.

Estimation of Total Numbers of *L. major* in Infected Mouse Tissue

Estimation of total numbers of *L. major* in the infected popliteal ganglion was performed by a limiting dilution assay (Titus, R. G. et al. 1985) and measurement of reporter gene activity following the procedure outlined by Bérubé et al. (1996).

Measurement of Antibody

PT3- or AgfA-specific antibodies were measured by the ELISA method (Engvall and Carlsson, 1976) involving 96-well DNA-bind plates (Corning-Costar) coated with either PT3 peptide, polymerized SEF17 or depolymerized SEF17 pre-treated with 90% formic acid at a concentration of 1 $\mu$g/well. Immune serum from each BALB/c mouse was tested in triplicate at a dilution of 1 in 100.

Statistics

Statistical significance was analyzed by determining the standard error of the mean (n=5). If the mean values +/− standard error for different groups of mice did not overlap, the results were considered significant (Duncan et al., 1977).

Results

Optimizing Expression of SEF17 Fimbrial Fibers Displaying the PT3 Epitope

To determine the optimal conditions for expression of chimeric SEF17 fibers, *S. enteritidis* strains A4, A5, A8 were grown in TSB and T broth for 6, 24 or 48 h, static or shaking at 200 rpm. The cell pellets were harvested and the amount of cell-associated fimbrial material was determined by SDS-PAGE and immunoblotting. Strains A4, A5 and A8 all produced maximal amounts of cell-associated AgfA::PT3 when grown for 48 h in T broth, shaking at 200 rpm (Table 9). The *S. enteritidis* 3b parental strain produced large amounts of cell-associated AgfA under most T broth conditions and was generally less variable in the amount detected with the cell pellet (Table 9). Cell-associated AgfA or AgfA::PT3 were not detected when strains were grown in TSB (data not shown).

Strain A4 has been characterized further than other strains containing agfA::PT3 (data not shown). Therefore, *S. enteritidis* A4 was chosen to be tested as a vaccine against *L. major*.

TABLE 9

Expression of cell-associated chimeric SEF17 under different growth conditions.

| | Production of cell-associated SEF17[b] | | | | | |
|---|---|---|---|---|---|---|
| | 6 h | | 24 h | | 48 h | |
| Strain[a] | 0 rpm[c] | 200 rpm | 0 rpm | 200 rpm | 0 rpm | 200 rpm |
| 3b | – | – | +++ | +++ | +++ | +++ |
| A4 | – | – | + | ++ | + | ++ |
| A5 | – | – | ++ | + | ++ | +++ |
| A8 | – | – | + | + | + | +++ |

[a]*S. enteritidis* 27655-3b strains: parental strain 3b; agfA::PT3 (A4, A5, A8).
[b]*S. enteritidis* strains were assessed for production of cell-associated chimeric SEF17 production after growth in T broth by SDS-PAGE and immunoblotting as described in Materials and Methods. Presence of AgfA::PT3 on immunoblots was scored as follows: equal to parental 3b AgfA levels (+++); slightly reduced levels (++); significantly reduced levels (+); not detectable (–)
[c]0 rpm refers to static growth and 200 rpm refers to shaken cultures.

Vaccine Dosage and Route of Delivery

Preliminary experiments to test the virulence of *S. enteritidis* 3b in BALB/c mice showed that a safe oral vaccination dose was $10^5$ organisms/mouse. After administration of this dose to BALB/c mice, no deaths were recorded after 10 days and no CFUs of *S. enteritidis* were detected in the spleens and livers of mice after 28 days of infection (data not shown).

Vaccination of BALB/c Mice and Subsequent Challenge With *L. major*

The experimental outline for *S. enteritidis* vaccination and *L. major* challenge is shown in Table 10. BALB/c mice were vaccinated once with $10^5$ cells of *S. enteritidis* A4 or 3b. Control mice were administered an equal volume of PBS orally. Two weeks later, selected groups of mice received a second oral dose of $10^3$ cells of *S. enteritidis* A4 or 3b.

Vaccinated mice were challenged in the footpad with *L. major* either 4, 6 or 8 weeks after the first vaccination and footpad swelling was monitored. Four weeks after *L. major* challenge, group 1 mice (challenged 4 weeks after first vaccination) were sacrificed; there were no major differences in footpad inflammation between any of the mice (data not shown). There was notable increase in footpad inflammation with group 2 and 3 mice vaccinated with *S. enteritidis* A4 as compared to PBS-vaccinated control mice (FIG. 24 A-D). The largest difference between these two groups was observed in general, footpad inflammation in mice vaccinated with *S. enteritidis* 3b or A4 was very similar.

TABLE 10

*S. enteritidis* vaccination of BALB/c mice and challenge with *L. major.*

| | Vaccination[b] | | *Leishmania major* challenge[c] | | |
|---|---|---|---|---|---|
| Inoculum[a] | Day 0 | Day 14 | Week 4 | Week 6 | Week 8 |
| PBS | 15[d] | – | 5 | 5 | 5 |
| 3b | 15 | – | 5 | 5 | 5 |
| A4 | 15 | – | 5 | 5 | 5 |
| PBS | 15 | 15 | 5 | 5 | 5 |
| 3b | 15 | 15 | 5 | 5 | 5 |
| A4 | 15 | 15 | 5 | 5 | 5 |

[a]*S. enteritidis* 27655-3b strains: parental strain 3b; A4 (agfA::PT3#4).
[b]Oral immunizations of BALB/c mice with *S. enteritidis* 3b or A4 by gavage: $10^5$ CFU in 200 μl PBS administered at Day 0, $10^3$ CFU in 200 μl PBS administered at Day 14.
[c]Subcutaneous injection of live *L. major* into the right hind footpad of vaccinated BALB/c mice: $10^7$ parasites in 50 μl PBS administered at Week 4 or 6, $5 \times 10^6$ parasites in 50 μl PBS administered at Week 8.
[d]Numbers listed in table refer to numbers of BALB/c mice in each group.

Parasite Load in the Popliteal Lymph Nodes

Figure 25A:
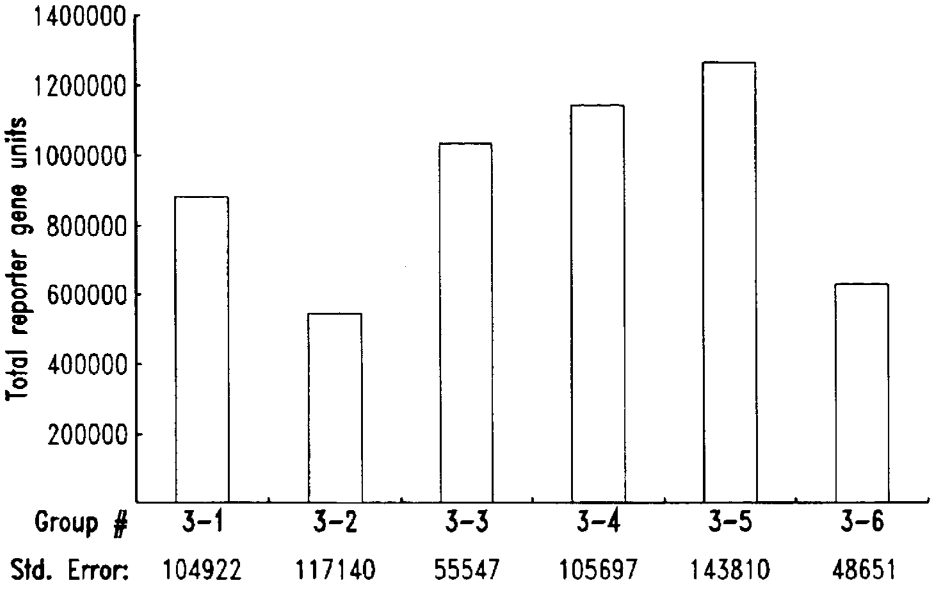
FIG. 25. Quantification of *Leishmania major* parasites in popliteal ganglions from infected BALB/c mice. *L. major* carrying a reporter gene was quantified by measuring reporter gene activity after performing a limiting dilution assay (Titus et al., 1985). Columns represent total reporter gene units (A) and reporter gene units per mg of organ (B) as the mean values from each group: 3-1, one dose of PBS only; 3-2 and 3-3, one vaccination with $10^5$ *S. enteritidis* 3b or A4, respectively; 3-4, two doses of PBS only; 3-5 and 3-6, two vaccinations with $10^5$ and $10^3$ *S. enteritidis* 3b or A4, respectively. All groups of mice were challenged in the footpad with $5\times10^6$ live *L. major* eight weeks after first vaccination. Standard errors of the mean for each group are listed below the appropriate columns at the bottom of each graph.
Figure 25B:
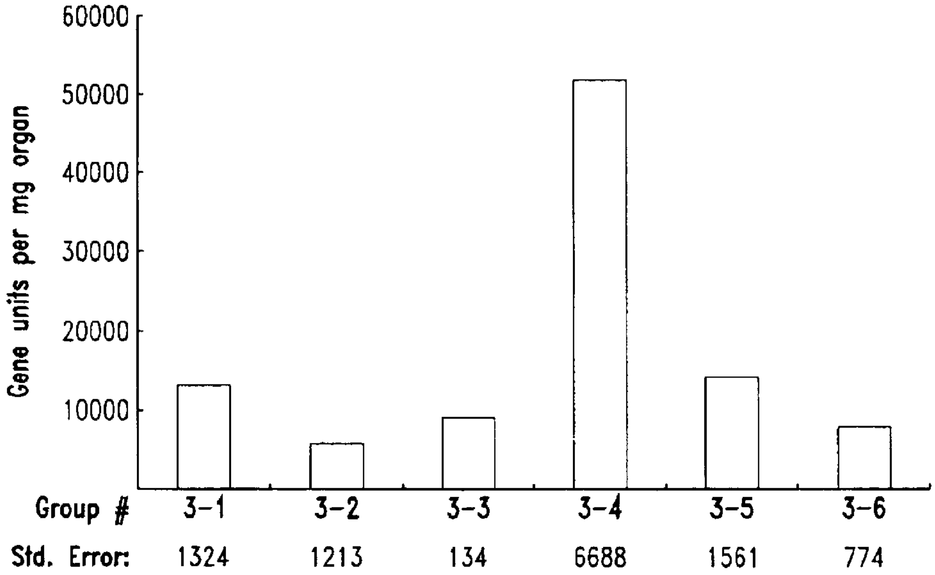

At the end of the *L. major* challenge experiment, mice were sacrificed and the right popliteal lymph nodes removed. Lymph node cells were homogenized and parasite load was evaluated by limited dilution assay (Titus et al., 1985) and measurement of reporter gene activity. Total reporter gene units and reporter gene units per mg of organ are represented for the 30 group 3 BALB/c mice challenged with *L. major* 8 weeks after vaccination (FIG. 25A, B). Popliteal lymph nodes from mice vaccinated once with *S. enteritidis* A4 had significantly lower reporter gene activity than the PBS-vaccinated control mice (FIG. 25B; group 3-3 versus 3-1). However, reporter gene activity levels for group 3-3 were higher than mice from control group 3-2, which received one dose of wild-type *S. enteritidis* 3b. More promising results were obtained for mice from group 3-6, which received two doses of the vaccine strain, *S. enteritidis* A4. Reporter gene activity levels in the lymph node tissue from these mice were significantly lower than both the PBS-vaccinated and *S. enteritidis* 3b-vaccinated groups of mice (FIG. 25B, groups 3-4, 3-5). This indicated that two vaccinations of BALB/c mice with *S. enteritidis* A4, which displays the *L. major* PT3 epitope at the cell surface, was enough to reduce the overall numbers of parasites.

Measurement of Antibody Levels in Mouse Serum

Figure 26A:
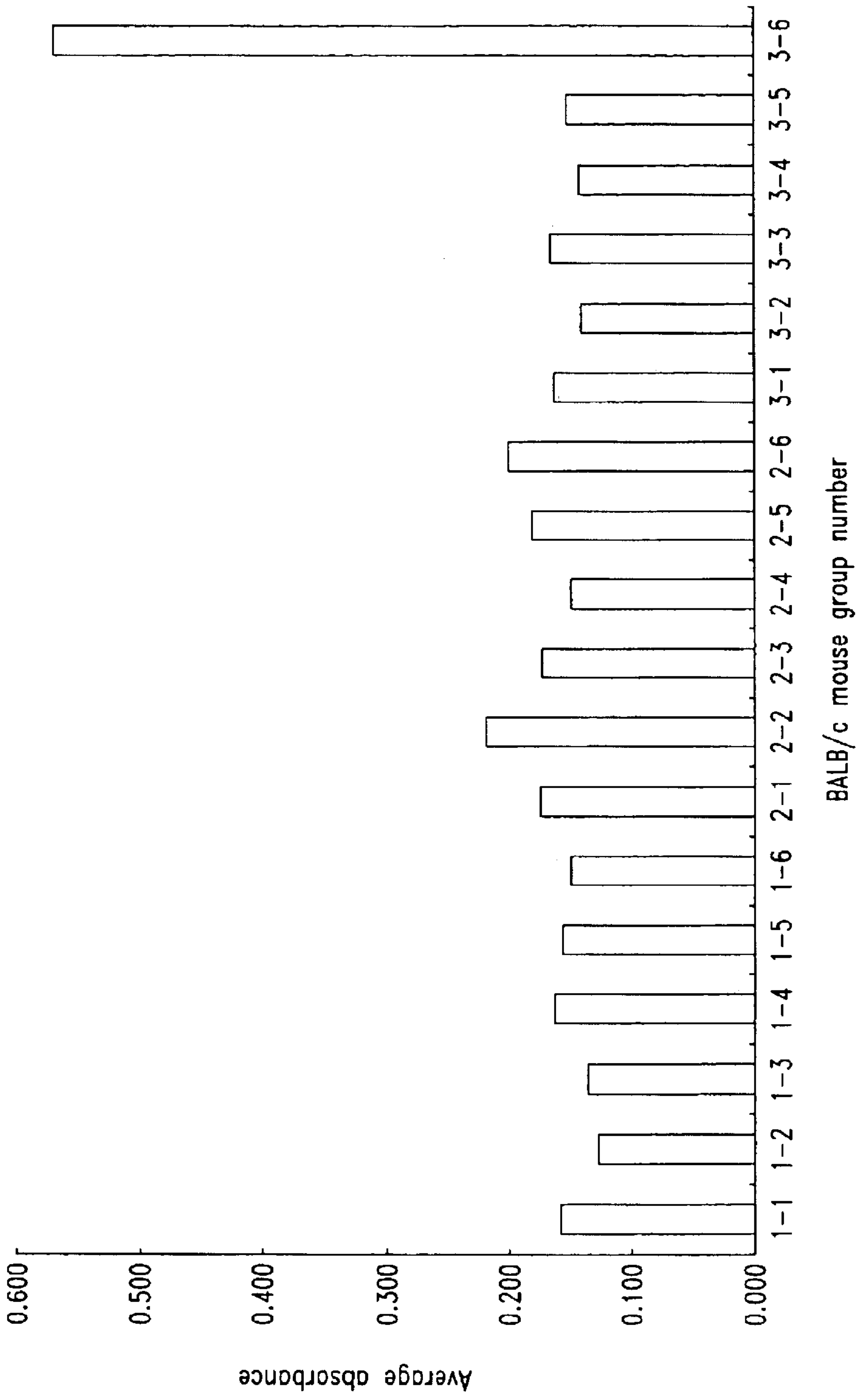
FIG. 26. Measurement of serum antibodies against PT3 peptide, SEF17 and AgfA. BALB/c mouse serum was tested in triplicate (1 in 100 dilution) by ELISA against 1 μg/well of PT3 peptide (A), polymerized SEF17 (B), or depolymerized SEF17 pre-treated with 90% formic acid (C; Collinson et al., 1991). Results shown are the mean absorbance values from each group of mice: 1-1, 2-1, 3-1, one dose of PBS only; 1-2, 2-2, 3-2, one vaccination with $10^5$ *S. enteritidis* 3b; 1-3, 2-3, 3-3, one vaccination with $10^5$ *S. enteritidis* A4; 1-4, 2-4, 3-4, two doses of PBS only; 1-5, 2-5, 3-5, two vaccinations with $10^5$ and $10^3$ *S. enteritidis* 3b; 1-6, 2-6, 3-6, two vaccinations with $10^5$ and $10^3$ *S. enteritidis* A4. Groups 1-1 to 1-6 and 2-1 to 2-6 were challenged in the footpad with $10^7$ live *L. major* four and six weeks after first vaccination, respectively, and groups 3-1 to 3-6 were challenged in the footpad with $5\times10^6$ live *L. major* eight weeks after first vaccination.
Figure 26B:
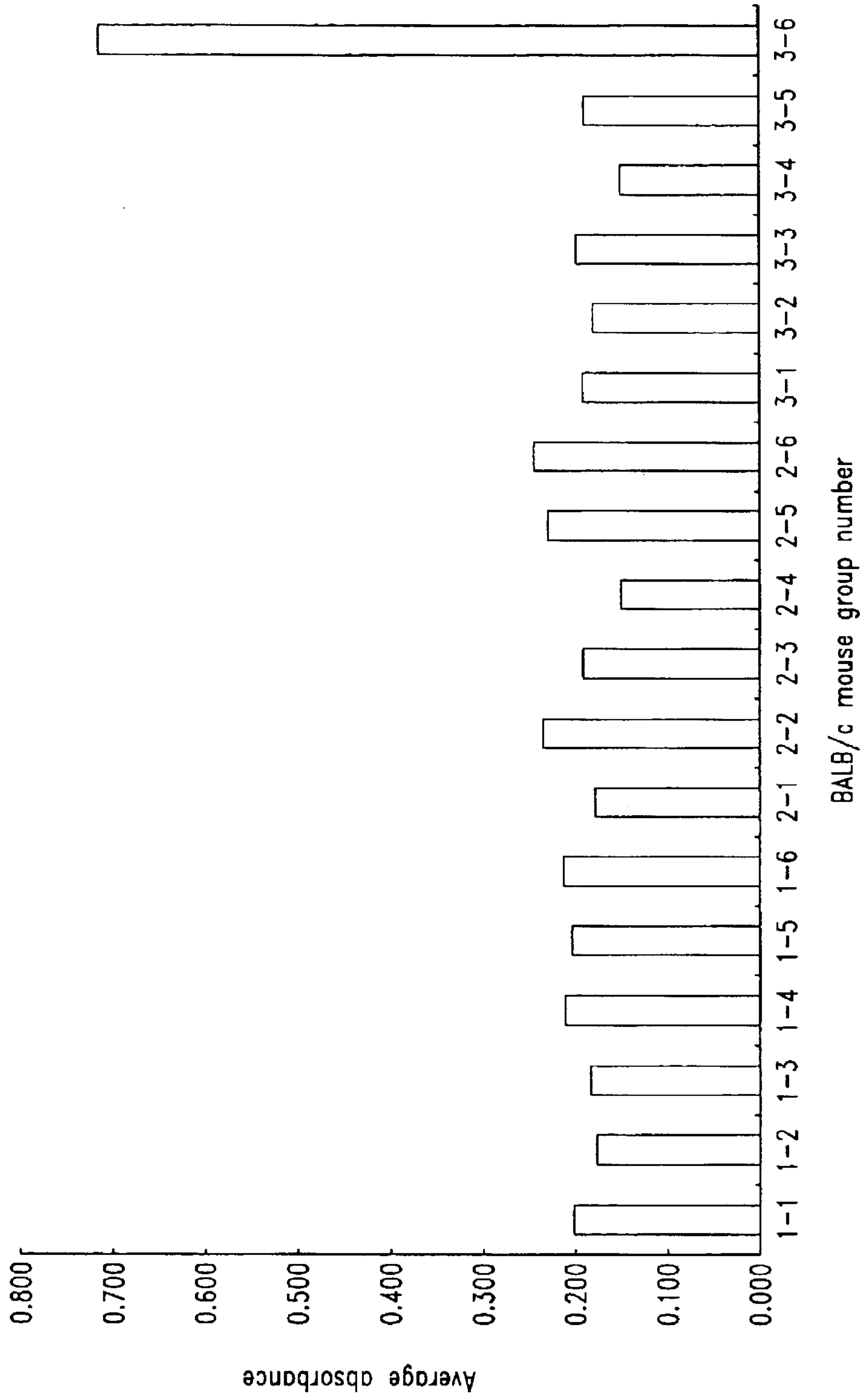
Figure 26C:
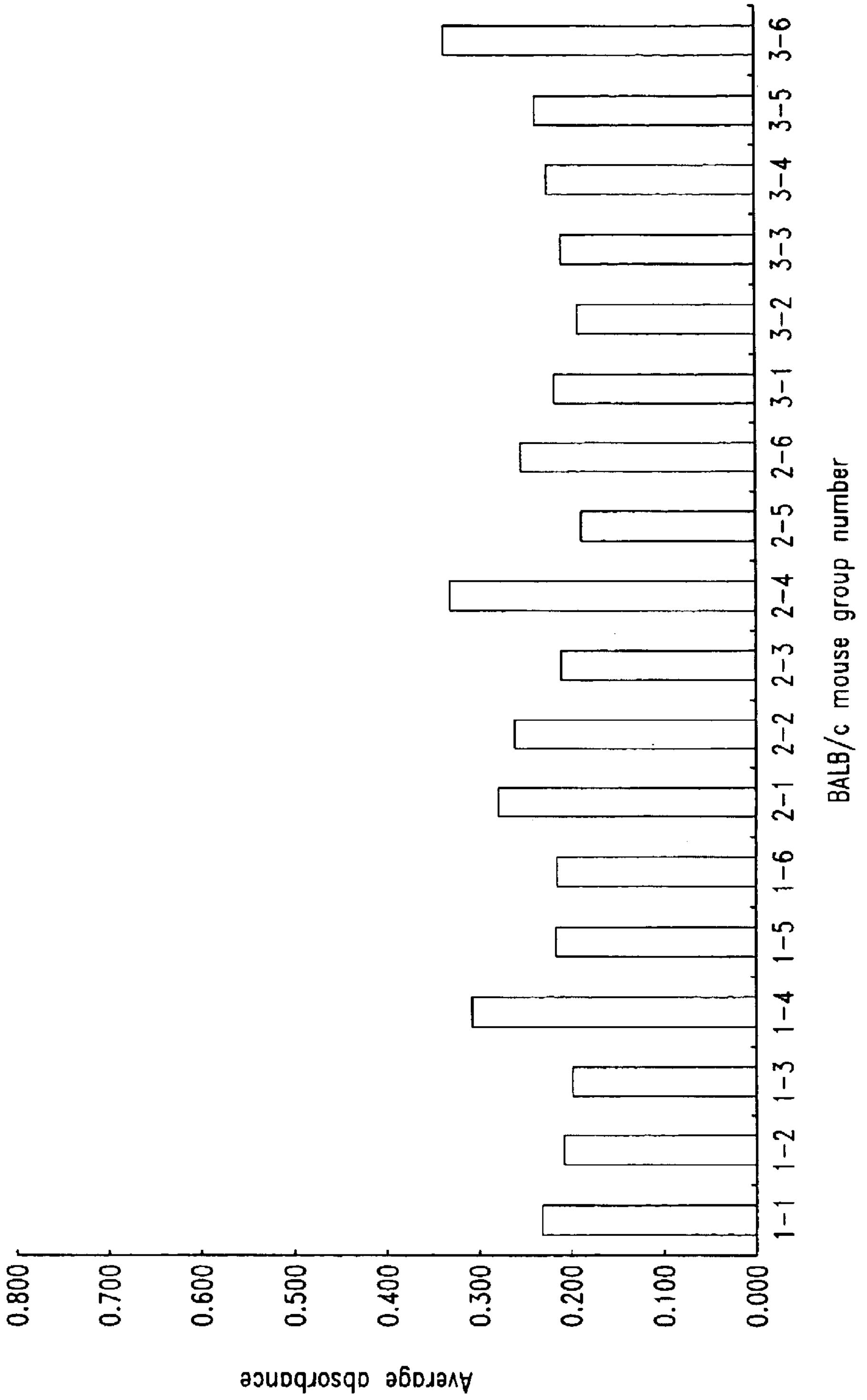

Immune sera from infected BALB/c mice were screened by ELISA for recognition of antigens carried by the *S. enteritidis* vaccine strain A4, specifically PT3 peptide and SEF17/AgfA (FIG. 26A-C). The strongest antibody response against PT3 (FIG. 26A) and polymerized SEF17 (FIG. 26B) was observed in mice from group 3-6, the group which received two vaccinations of *S. enteritidis* A4. These mean values were boosted by the strong response of one individual mouse in this group (data not shown). When immune sera were tested against SEF17 fimbriae which had been depolymerized into AgfA monomers by treatment with 90% formic acid (FIG. 26C), group 3-6 again had a strong antibody response. These results indicated that several mice vaccinated with *S. enteritidis* A4 had produced antibodies specific for chimeric SEF17 fimbriae carrying the PT3 eptiope.

Discussion

In summary, two oral vaccinations with *S. enteritidis* A4, displaying chimeric fimbriae containing the PT3 epitope from *L. major* gp63, caused a reduction in overall numbers of *L. major* in the popliteal lymph nodes with respect to *S. enteritidis* 3b- or PBS-vaccinated control mice. This was recorded even though footpad inflammation had significantly increased in the *S. enteritidis* A4 vaccinated mice with respect to control mice. Also, mice from the *S. enteritidis* A4 vaccinated group developed a significant humoral immune response against both the PT3 epitope as well as the AgfA protein which was carrying it. Therefore, there is clear evidence that presentation of the PT3 epitope in the context of SEF17 by *S. enteritidis* A4 was successful.

Several studies have reported vaccination of BALB/c mice against *Leishmania* by administering recombinant *Salmonella* vaccine strains producing the gp63 protein from *L. major* (González et al., 1998; McSorley et al., 1997; Xu et al., 1995). The authors correlate a decrease in footpad inflammation after *L. major* challenge with decreased parasite loads and protection against *L. major* infection. Olivier et al. (1998) correlated decreased footpad inflammation in vaccinated BALB/c mice with a drop in parasite load in the popliteal lymph nodes. Here a similar drop in parasite load in the popliteal ganglion of vaccinated mice occurred, but footpad inflammation had increased.

These differences may be due to the use of *S. enteritidis* as the carrier vaccine strain. *S. enteritidis* has been widely studied as a vaccine candidate chiefly to immunize poultry in a effort to reduce *Salmonella* load in chicken and egg products destined for human consumption. *S. enteritidis* can produce a sublethal, chronic infection in mice that is cleared over time (unpublished data), however, this *Salmonella* serotype is not normally studied as a carrier of heterologous antigens for vaccine efficacy trials in mice. It is not well characterized whether *S. enteritidis* will reach the appropriate mouse tissues to achieve optimum immune response against foreign epitopes which it is carrying. Hence, it is unknown what effect oral vaccination with *S. enteritidis* has on the BALB/c mice prior to challenge with *L. major* . In addition, *S. enteritidis* 3b has not been specifically attenuated for vaccine purposes.

Of all the *Salmonella* serovars available, *S. typhimurium,* the causative agent of murine typhoid, and *S. typhi*, the causative agent of human typhoid are the most well characterized with respect to vaccine development (Chatfield et al., 1992; Chatfield et al., 1993; Curtiss et al., 1994; Roberts et al., 1994; Levine et al., 1996). Presentation of our chimeric fimbriae in the context of one of these well-characterized vaccine strains may lead to even greater success with the epitope delivery system described herein. Assembly of chimeric SEF17 fimbriae in these strains would also occur since the agfA operon and assembly systems are highly conserved among the *Salmonellae* (Römling et al., 1998; Baumler et al., 1997; Collinson et al., 1996). Nevertheless, vaccination of BALB/c mice with *S. enteritidis* presenting the *Leishmania* PT3 epitope resulted in generation of a specific immune response against the heterologous epitope and an overall reduction of *L. major* cell numbers in the vaccinated host.

References Cited in Example 3

Bäumler, A J, et al. (1997). *Journal of Bacteriology,* 179: 317–322.

Berube, P, et al. (1996). *J Virol,* 70: 4009–4016.

Brun, R and M Schönenberger (1979). *Acta. Trop.,* 36: 289–292.

Chatfield, S, et al. (1993). *FEMS Immunol Med Microbiol,* 7: 1–7.

Chatfield, S N, et al. (1992). *Microb Pathog,* 12: 145–151.

Collinson, S K, et al. (1996). *J. Bacteriol.,* 178: 662–667.

Collinson, S K, et al. (1993). *J. Bacteriol.,* 175: 12–18.

Collinson, S K, et al. (1991). *J. Bacteriol,* 173: 4773–4781.

Curtiss III, R, et al. (1994). *Dev. Biol. Stand.,* 82: 23–33.

Duncan, R C, et al. (1977). *Introductory biostatistics for the health sciences,* John Wiley & Sons.

Engvall, E and H E Carlsson (1976). In: Feldmann C, et al., ed *Immunoenzymatic techniques.* Amsterdam, North-Holland.

Feutrier, J, et al. (1986). *J. Bacteriol.,* 168: 221–227.

Gonzalez, C R, et al. (1998). *Vaccine,* 16: 1043–1052.

Ha, D S, et al. (1996). *Mol Biochem Parasitol,* 77: 57–64.

Jardim, A J (1994). Immunological and biochemical characterization of the major surface membrane proteins: gp63 and the lipophosphoglycan associated protein of *Leishmania,* University of Victoria.

Laemmli, U K (1970). *Nature* (London), 227: 680–685.

Levine, M M, et al. (1996). *J. Biotech.,* 44: 193–196.

Locksley, R M, et al. (1999). *J Infect Dis,* 179 Suppl 2: S305–308.

McSorley, S J, et al. (1997). *Infect. Immun.,* 65: 171–178.

Olivier, M, et al. (1998). *J Biol Chem,* 273: 13944–13949.

Roberts, M, et al. (1994). *Salmonella as carriers of heterologous antigens. Novel Delivery Systems for Oral Vaccines,* CRC Press Inc.

Römling, U, et al. (1998). *Journal of Bacteriology,* 180: 722–731.

Spitzer, N, et al. (1999). *Vaccine,* 17: 1298–1300.

Titus, R G, et al. (1985). *Parasite Immunol,* 7: 545–555.

Xu, D, et al. (1995). *Immunology,* 85: 1–7.

What is claimed is:

1. A recombinant nucleic acid molecule that encodes a chimeric agfA fimbrin polypeptide comprising at least one heterologous antigen, wherein said nucleic acid molecule encodes a chimeric polypeptide selected from the group consisting of SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, and SEQ ID NO:30.

2. The recombinant nucleic acid molecule according to claim 1 wherein said recombinant nucleic acid molecule is present in an expression vector, said expression vector producing the chimeric polypeptide when expressed in a host cell.

3. A host cell comprising the recombinant nucleic acid molecule according to claim 5 wherein said host cell produces the chimeric polypeptide.

4. The host cell according to claim 3 wherein said host cell produces stable fimbriae comprising the chimeric polypeptide.

5. The host cell according to claim 3 or claim 4 wherein said host cell is selected from the group consisting of a strain of *Enterobacteriaceae, Escherichia coli,* and *Salmonella.*

6. The recombinant nucleic acid molecule according to claim 1 wherein said recombinant nucleic acid molecule is in the chromosome of a host cell.

7. The recombinant nucleic acid molecule according to claim 6 wherein said host cell produces the chimeric polypeptide.

8. The recombinant nucleic acid molecule according to claim 6 wherein said host cell produces stable fimbriae comprising the chimeric polypeptide.

9. The recombinant nucleic acid molecule according to any one of claims 6–8 wherein said host cell is selected from the group consisting of a strain of *Enterobacteriaceae, Escherichia coli,* and *Salmonella.*

* * * * *

UNITED STATES PATENT AND TRADEMARK OFFICE

CERTIFICATE OF CORRECTION

PATENT NO. : 6,864,365 B1
DATED : March 8, 2005
INVENTOR(S) : Aaron P. White et al.

It is certified that error appears in the above-identified patent and that said Letters Patent is hereby corrected as shown below:

Column 95,
Line 14, "agfA" should read as -- AgfA --.
Line 27, "claim 5 wherein" should read as -- claim 2 wherein --.

Signed and Sealed this

Eleventh Day of October, 2005

JON W. DUDAS
*Director of the United States Patent and Trademark Office*

SEQUENCE LISTING

```
<160> NUMBER OF SEQ ID NOS: 59

<210> SEQ ID NO 1
<211> LENGTH: 456
<212> TYPE: DNA
<213> ORGANISM: Salmonella enteritidis

<400> SEQUENCE: 1

atgaaacttt taaaagtggc agcattcgca gcaatcgtag tttctggcag tgctctggct     60

ggcgtcgttc cacaatgggg cggcggcggt aatcataacg gcggcggcaa tagttccggc    120

ccggactcaa cgttgagcat ttatcagtac ggttccgcta acgctgcgct tgctctgcaa    180

agcgatgccc gtaaatctga aacgaccatt acccagagcg gttatggtaa cggcgccgat    240

gtaggccagg gtgcggataa tagtactatt gaactgactc agaatggttt cagaaataat    300

gccaccatcg accagtggaa cgctaaaaac tccgatatta ctgtcggcca atacggcggt    360

aataacgccg cgctggttaa tcagaccgca tctgattcca gcgtaatggt gcgtcaggtt    420

ggttttggca acaacgccac ggctaaccag tattaa                              456

<210> SEQ ID NO 2
<211> LENGTH: 456
<212> TYPE: DNA
<213> ORGANISM: Salmonella enteritidis

<400> SEQUENCE: 2

atgaaaaaca aattgttatt tatgatgttg acaatactgg gtgcgcctgg gattgcaacc     60

gcgacaaatt atgatctggc tcgttcagaa tataattttg cggtaaatga attaagcaag    120

tcttcattta atcaggcggc cattattggt caagtcggca cggataatag tgccagagta    180

cgccaggaag gatcaaaact attgtccgtt atttcacaag aaggaggaaa taatcgggcg    240

aaagtcgacc aggcagggaa ttataacttt gcgtatattg agcaaacggg caatgccaac    300

gatgccagta tatcgcaaag cgcttacggt aatagtgcag ctattatcca gaaaggttct    360

ggaaataagg ccaatattac ccagtacggt acgcagaaaa cagcagttgt agtgcagaaa    420
```

-continued cagtcgcata tggctattcg cgtcacccaa cgctaa 456

<210> SEQ ID NO 3
<211> LENGTH: 456
<212> TYPE: DNA
<213> ORGANISM: E. Coli

<400> SEQUENCE: 3
atgaaacttt taaaagtaga agcaattgca gcaatcgtat tctccggtag cgctctggca 60
ggtgttgttc ctcagtacgg cggcggcggt aaccacggtg gtggcggtaa taatagcggc 120
ccaaattctg agctgaacat ttaccagtac ggtggcggta actctgcact tgctctgcaa 180
actgatgccc gtaactctga cttgactatt acccagcatg gcggcggtaa tggtgcagat 240
gttggtcagg gctcagatga cagctcaatc gatctgaccc aacgtggctt cggtaacagc 300
gctactcttg atcagtggaa cggcaaaaat tctgaaatga cggttaaaca gttcggtggt 360
ggcaacggtg ctgcagttga ccagactgca tctaactcct ccgtcaacgt gactcaggtt 420
ggctttggta acaacgcgac cgctcatcag tactaa 456

<210> SEQ ID NO 4
<211> LENGTH: 456
<212> TYPE: DNA
<213> ORGANISM: E. Coli

<400> SEQUENCE: 4
atgaaaaaca aattgttatt tatgatgtta acaatactgg gtgcgcctgg gattgcagcc 60
gcagcaggtt atgatttagc taattcagaa tataacttcg cggtaaatga attgagtaag 120
tcttcattta atcaggcagc cataattggt caagctggga ctaataatag tgctcagtta 180
cggcagggag gctcaaaact tttggcggtt gttgcgcaag aaggtagtag caaccgggca 240
aagattgacc agacaggaga ttataacctt gcatatattg atcaggcggg cagtgccaac 300
gatgccagta tttcgcaagg tgcttatggt aatactgcga tgattatcca gaaaggttct 360
ggtaataaag caaatattac acagtatggt actcaaaaaa cggcaattgt agtgcagaga 420
cagtcgcaaa tggctattcg cgtgacacaa cgttaa 456

<210> SEQ ID NO 5
<211> LENGTH: 151
<212> TYPE: PRT
<213> ORGANISM: Salmonella enteritidis

<400> SEQUENCE: 5

Met Lys Leu Leu Lys Val Ala Ala Phe Ala Ala Ile Val Val Ser Gly
1 5 10 15

Ser Ala Leu Ala Gly Val Val Pro Gln Trp Gly Gly Gly Gly Asn His
20 25 30

Asn Gly Gly Gly Asn Ser Ser Gly Pro Asp Ser Thr Leu Ser Ile Tyr
35 40 45

Gln Tyr Gly Ser Ala Asn Ala Ala Leu Ala Leu Gln Ser Asp Ala Arg
50 55 60

Lys Ser Glu Thr Thr Ile Thr Gln Ser Gly Tyr Gly Asn Gly Ala Asp
65 70 75 80

Val Gly Gln Gly Ala Asp Asn Ser Thr Ile Glu Leu Thr Gln Asn Gly
85 90 95

Phe Arg Asn Asn Ala Thr Ile Asp Gln Trp Asn Ala Lys Asn Ser Asp
100 105 110

-continued

```
Ile Thr Val Gly Gln Tyr Gly Gly Asn Asn Ala Ala Leu Val Asn Gln
        115                 120                 125

Thr Ala Ser Asp Ser Ser Val Met Val Arg Gln Val Gly Phe Gly Asn
    130                 135                 140

Asn Ala Thr Ala Asn Gln Tyr
145                 150


<210> SEQ ID NO 6
<211> LENGTH: 151
<212> TYPE: PRT
<213> ORGANISM: Salmonella enteritidis

<400> SEQUENCE: 6

Met Lys Asn Lys Leu Leu Phe Met Met Leu Thr Ile Leu Gly Ala Pro
 1               5                  10                  15

Gly Ile Ala Thr Ala Thr Asn Tyr Asp Leu Ala Arg Ser Glu Tyr Asn
            20                  25                  30

Phe Ala Val Asn Glu Leu Ser Lys Ser Ser Phe Asn Gln Ala Ala Ile
        35                  40                  45

Ile Gly Gln Val Gly Thr Asp Asn Ser Ala Arg Val Arg Gln Glu Gly
    50                  55                  60

Ser Lys Leu Leu Ser Val Ile Ser Gln Glu Gly Gly Asn Asn Arg Ala
65                  70                  75                  80

Lys Val Asp Gln Ala Gly Asn Tyr Asn Phe Ala Tyr Ile Glu Gln Thr
                85                  90                  95

Gly Asn Ala Asn Asp Ala Ser Ile Ser Gln Ser Ala Tyr Gly Asn Ser
            100                 105                 110

Ala Ala Ile Ile Gln Lys Gly Ser Gly Asn Lys Ala Asn Ile Thr Gln
        115                 120                 125

Tyr Gly Thr Gln Lys Thr Ala Val Val Val Gln Lys Gln Ser His Met
    130                 135                 140

Ala Ile Arg Val Thr Gln Arg
145                 150


<210> SEQ ID NO 7
<211> LENGTH: 151
<212> TYPE: PRT
<213> ORGANISM: Escherichia coli

<400> SEQUENCE: 7

Met Lys Leu Leu Lys Val Ala Ala Ile Ala Ala Ile Val Phe Ser Gly
 1               5                  10                  15

Ser Ala Leu Ala Gly Val Val Pro Gln Tyr Gly Gly Gly Gly Asn His
            20                  25                  30

Gly Gly Gly Gly Asn Asn Ser Gly Pro Asn Ser Glu Leu Asn Ile Tyr
        35                  40                  45

Gln Tyr Gly Gly Gly Asn Ser Ala Leu Ala Leu Gln Thr Asp Ala Arg
    50                  55                  60

Asn Ser Asp Leu Thr Ile Thr Gln His Gly Gly Gly Asn Gly Ala Asp
65                  70                  75                  80

Val Gly Gln Gly Ser Asp Asp Ser Ser Ile Asp Leu Thr Gln Arg Gly
                85                  90                  95

Phe Gly Asn Ser Ala Thr Leu Asp Gln Trp Asn Gly Lys Asn Ser Glu
            100                 105                 110

Met Thr Val Lys Gln Phe Gly Gly Gly Asn Gly Ala Ala Val Asp Gln
        115                 120                 125
```

```
Thr Ala Ser Asn Ser Ser Val Asn Val Thr Gln Val Gly Phe Gly Asn
    130                 135                 140

Asn Ala Thr Ala His Gln Tyr
145                 150


<210> SEQ ID NO 8
<211> LENGTH: 151
<212> TYPE: PRT
<213> ORGANISM: Escherichia coli

<400> SEQUENCE: 8

Met Lys Asn Lys Leu Leu Phe Met Met Leu Thr Ile Leu Gly Ala Pro
 1               5                  10                  15

Gly Ile Ala Ala Ala Ala Gly Tyr Asp Leu Ala Asn Ser Glu Tyr Asn
            20                  25                  30

Phe Ala Val Asn Glu Leu Ser Lys Ser Ser Phe Asn Gln Ala Ala Ile
        35                  40                  45

Ile Gly Gln Ala Gly Thr Asn Asn Ser Ala Gln Leu Arg Gln Gly Gly
    50                  55                  60

Ser Lys Leu Leu Ala Val Val Ala Gln Glu Gly Ser Ser Asn Arg Ala
65                  70                  75                  80

Lys Ile Asp Gln Thr Gly Asp Tyr Asn Leu Ala Tyr Ile Asp Gln Ala
                85                  90                  95

Gly Ser Ala Asn Asp Ala Ser Ile Ser Gln Gly Ala Tyr Gly Asn Thr
            100                 105                 110

Ala Met Ile Ile Gln Lys Gly Ser Gly Asn Lys Ala Asn Ile Thr Gln
        115                 120                 125

Tyr Gly Thr Gln Lys Thr Ala Ile Val Val Gln Arg Gln Ser Gln Met
    130                 135                 140

Ala Ile Arg Val Thr Gln Arg
145                 150


<210> SEQ ID NO 9
<211> LENGTH: 48
<212> TYPE: DNA
<213> ORGANISM: Leishmania  major

<400> SEQUENCE: 9

tatgatcagc tggttacccg tgttgttacc catgaaatgg cacatgca                  48


<210> SEQ ID NO 10
<211> LENGTH: 16
<212> TYPE: PRT
<213> ORGANISM: Leishmania major

<400> SEQUENCE: 10

Tyr Asp Gln Leu Val Thr Arg Val Val Thr His Glu Met Ala His Ala
 1               5                  10                  15


<210> SEQ ID NO 11
<211> LENGTH: 456
<212> TYPE: DNA
<213> ORGANISM: Artificial Sequence
<220> FEATURE:
<223> OTHER INFORMATION: Recombinant Salmonella enteritidis 3b afgA
      sequence containing the replacement fragment
      encoding PT3 from GP63 of Leishmania major.

<400> SEQUENCE: 11

atgaaacttt taaaagtggc agcattcgca gcaatcgtag tttctggcag tgctctggct     60
```

-continued

```
ggcgtcgttc cacaatgggg cggcggcggt aatcataacg gcggcggcaa tagttccggc    120

ccggactcaa cgttgagcat ttatcagtac ggttccgcta acgctgcgct tgctctgcaa    180

agcgatgccc gtaaatctga aacgaccatt acccagagcg gttatggtaa cggcgccgat    240

gtaggccagg gtgcggataa tagtactatt gaactgactc agaatggttt cagaaataat    300

gccaccatcg accagtggaa cgctaaaaac tccgatatta ctgtcggcca atacggcggt    360

aataacgccg cgctggttaa ttatgatcag ctggttaccc gtgttgttac ccatgaaatg    420

gcacatgcaa acaacgccac ggctaaccag tattaa                              456
```

<210> SEQ ID NO 12
<211> LENGTH: 151
<212> TYPE: PRT
<213> ORGANISM: Artificial Sequence
<220> FEATURE:
<223> OTHER INFORMATION: Recombinant Salmonella enteritidis 3b afgA sequence containing the replacement fragment encoding PT3 from GP63 of Leishmania major.

<400> SEQUENCE: 12

```
Met Lys Leu Leu Lys Val Ala Ala Phe Ala Ala Ile Val Val Ser Gly
 1               5                  10                  15

Ser Ala Leu Ala Gly Val Val Pro Gln Trp Gly Gly Gly Gly Asn His
            20                  25                  30

Asn Gly Gly Gly Asn Ser Ser Gly Pro Asp Ser Thr Leu Ser Ile Tyr
        35                  40                  45

Gln Tyr Gly Ser Ala Asn Ala Ala Leu Ala Leu Gln Ser Asp Ala Arg
    50                  55                  60

Lys Ser Glu Thr Thr Ile Thr Gln Ser Gly Tyr Gly Asn Gly Ala Asp
65                  70                  75                  80

Val Gly Gln Gly Ala Asp Asn Ser Thr Ile Glu Leu Thr Gln Asn Gly
                85                  90                  95

Phe Arg Asn Asn Ala Thr Ile Asp Gln Trp Asn Ala Lys Asn Ser Asp
            100                 105                 110

Ile Thr Val Gly Gln Tyr Gly Gly Asn Asn Ala Ala Leu Val Asn Tyr
        115                 120                 125

Asp Gln Leu Val Thr Arg Val Val Thr His Glu Met Ala His Ala Asn
    130                 135                 140

Asn Ala Thr Ala Asn Gln Tyr
145                 150
```

<210> SEQ ID NO 13
<211> LENGTH: 456
<212> TYPE: DNA
<213> ORGANISM: Artificial Sequence
<220> FEATURE:
<223> OTHER INFORMATION: Recombinant Salmonella enteritidis 3b afgA sequence containing the replacement fragment encoding PT3 from GP63 of Leishmania major.

<400> SEQUENCE: 13

```
atgaaacttt taaaagtggc agcattcgca gcaatcgtag tttctggcag tgctctggct     60

ggcgtcgttc cacaatgggg cggcggcggt aatcataacg gcggcggcaa tagttccggc    120

ccggactcaa cgttgagcat ttatcagtac ggttccgcta acgctgcgct tgctctgcaa    180

agcgatgccc gtaaatctga aacgaccatt acccagagcg gttatggtaa cggcgccgat    240

gtaggccagg gtgcggataa tagtactatt gaactgactc agaatggttt cagaaataat    300
```

-continued

```
gccaccatcg accagtggaa cgctaaaaac tccgatatta ctgtcggcca atatgatcag    360

ctggttaccc gtgttgttac ccatgaaatg gcacatgcaa gcgtaatggt gcgtcaggtt    420

ggttttggca acaacgccac ggctaaccag tattaa                              456


<210> SEQ ID NO 14
<211> LENGTH: 151
<212> TYPE: PRT
<213> ORGANISM: Artificial Sequence
<220> FEATURE:
<223> OTHER INFORMATION: Recombinant Salmonella enteritidis 3b afgA
      sequence containing the replacement fragment
      encoding PT3 from GP63 of Leishmania major.

<400> SEQUENCE: 14

Met Lys Leu Leu Lys Val Ala Ala Phe Ala Ala Ile Val Val Ser Gly
 1               5                  10                  15

Ser Ala Leu Ala Gly Val Val Pro Gln Trp Gly Gly Gly Gly Asn His
            20                  25                  30

Asn Gly Gly Gly Asn Ser Ser Gly Pro Asp Ser Thr Leu Ser Ile Tyr
        35                  40                  45

Gln Tyr Gly Ser Ala Asn Ala Ala Leu Ala Leu Gln Ser Asp Ala Arg
    50                  55                  60

Lys Ser Glu Thr Thr Ile Thr Gln Ser Gly Tyr Gly Asn Gly Ala Asp
65                  70                  75                  80

Val Gly Gln Gly Ala Asp Asn Ser Thr Ile Glu Leu Thr Gln Asn Gly
                85                  90                  95

Phe Arg Asn Asn Ala Thr Ile Asp Gln Trp Asn Ala Lys Asn Ser Asp
            100                 105                 110

Ile Thr Val Gly Gln Tyr Asp Gln Leu Val Thr Arg Val Val Thr His
        115                 120                 125

Glu Met Ala His Ala Ser Val Met Val Arg Gln Val Gly Phe Gly Asn
    130                 135                 140

Asn Ala Thr Ala Asn Gln Tyr
145                 150


<210> SEQ ID NO 15
<211> LENGTH: 456
<212> TYPE: DNA
<213> ORGANISM: Artificial Sequence
<220> FEATURE:
<223> OTHER INFORMATION: Recombinant Salmonella enteritidis 3b afgA
      sequence containing the replacement fragment
      encoding PT3 from GP63 of Leishmania major.

<400> SEQUENCE: 15

atgaaacttt taaaagtggc agcattcgca gcaatcgtag tttctggcag tgctctggct     60

ggcgtctatg atcagctggt tacccgtgtt gttacccatg aaatggcaca tgcatccggc    120

ccggactcaa cgttgagcat ttatcagtac ggttccgcta acgctgcgct tgctctgcaa    180

agcgatgccc gtaaatctga aacgaccatt acccagagcg gttatggtaa cggcgccgat    240

gtaggccagg gtgcggataa tagtactatt gaactgactc agaatggttt cagaaataat    300

gccaccatcg accagtggaa cgctaaaaac tccgatatta ctgtcggcca atacggcggt    360

aataacgccg cgctggttaa tcagaccgca tctgattcca gcgtaatggt gcgtcaggtt    420

ggttttggca acaacgccac ggctaaccag tattaa                              456


<210> SEQ ID NO 16
<211> LENGTH: 151
```

-continued

<212> TYPE: PRT
<213> ORGANISM: Artificial Sequence
<220> FEATURE:
<223> OTHER INFORMATION: Recombinant Salmonella enteritidis 3b afgA
sequence containing the replacement fragment
encoding PT3 from GP63 of Leishmania major.

<400> SEQUENCE: 16

```
Met Lys Leu Leu Lys Val Ala Ala Phe Ala Ala Ile Val Val Ser Gly
 1               5                  10                  15

Ser Ala Leu Ala Gly Val Tyr Asp Gln Leu Val Thr Arg Val Val Thr
            20                  25                  30

His Glu Met Ala His Ala Ser Gly Pro Asp Ser Thr Leu Ser Ile Tyr
        35                  40                  45

Gln Tyr Gly Ser Ala Asn Ala Ala Leu Ala Leu Gln Ser Asp Ala Arg
    50                  55                  60

Lys Ser Glu Thr Thr Ile Thr Gln Ser Gly Tyr Gly Asn Gly Ala Asp
65                  70                  75                  80

Val Gly Gln Gly Ala Asp Asn Ser Thr Ile Glu Leu Thr Gln Asn Gly
                85                  90                  95

Phe Arg Asn Asn Ala Thr Ile Asp Gln Trp Asn Ala Lys Asn Ser Asp
            100                 105                 110

Ile Thr Val Gly Gln Tyr Gly Gly Asn Asn Ala Ala Leu Val Asn Gln
        115                 120                 125

Thr Ala Ser Asp Ser Ser Val Met Val Arg Gln Val Gly Phe Gly Asn
    130                 135                 140

Asn Ala Thr Ala Asn Gln Tyr
145                 150
```

<210> SEQ ID NO 17
<211> LENGTH: 456
<212> TYPE: DNA
<213> ORGANISM: Artificial Sequence
<220> FEATURE:
<223> OTHER INFORMATION: Recombinant Salmonella enteritidis 3b afgA
sequence containing the replacement fragment
encoding PT3 from GP63 of Leishmania major.

<400> SEQUENCE: 17

```
atgaaacttt taaaagtggc agcattcgca gcaatcgtag tttctggcag tgctctggct     60

ggcgtcgttc cacaatgggg cggcggcggt aatcataacg gcggcggcaa tagttccggc    120

ccggactatg atcagctggt tacccgtgtt gttacccatg aaatggcaca tgcactgcaa    180

agcgatgccc gtaaatctga aacgaccatt acccagagcg gttatggtaa cggcgccgat    240

gtaggccagg gtgcggataa tagtactatt gaactgactc agaatggttt cagaaataat    300

gccaccatcg accagtggaa cgctaaaaac tccgatatta ctgtcggcca atacggcggt    360

aataacgccg cgctggttaa tcagaccgca tctgattcca gcgtaatggt gcgtcaggtt    420

ggttttggca acaacgccac ggctaaccag tattaa                              456
```

<210> SEQ ID NO 18
<211> LENGTH: 151
<212> TYPE: PRT
<213> ORGANISM: Artificial Sequence
<220> FEATURE:
<223> OTHER INFORMATION: Recombinant Salmonella enteritidis 3b afgA
sequence containing the replacement fragment
encoding PT3 from GP63 of Leishmania major.

<400> SEQUENCE: 18

-continued

```
Met Lys Leu Leu Lys Val Ala Ala Phe Ala Ala Ile Val Val Ser Gly
 1               5                  10                  15

Ser Ala Leu Ala Gly Val Val Pro Gln Trp Gly Gly Gly Gly Asn His
            20                  25                  30

Asn Gly Gly Gly Asn Ser Ser Gly Pro Asp Tyr Asp Gln Leu Val Thr
        35                  40                  45

Arg Val Val Thr His Glu Met Ala His Ala Leu Gln Ser Asp Ala Arg
    50                  55                  60

Lys Ser Glu Thr Thr Ile Thr Gln Ser Gly Tyr Gly Asn Gly Ala Asp
65                  70                  75                  80

Val Gly Gln Gly Ala Asp Asn Ser Thr Ile Glu Leu Thr Gln Asn Gly
                85                  90                  95

Phe Arg Asn Asn Ala Thr Ile Asp Gln Trp Asn Ala Lys Asn Ser Asp
            100                 105                 110

Ile Thr Val Gly Gln Tyr Gly Gly Asn Asn Ala Ala Leu Val Asn Gln
        115                 120                 125

Thr Ala Ser Asp Ser Ser Val Met Val Arg Gln Val Gly Phe Gly Asn
    130                 135                 140

Asn Ala Thr Ala Asn Gln Tyr
145                 150
```

<210> SEQ ID NO 19
<211> LENGTH: 456
<212> TYPE: DNA
<213> ORGANISM: Artificial Sequence
<220> FEATURE:
<223> OTHER INFORMATION: Recombinant Salmonella enteritidis 3b afgA sequence containing the replacement fragment encoding PT3 from GP63 of Leishmania major.

<400> SEQUENCE: 19

```
atgaaacttt taaaagtggc agcattcgca gcaatcgtag tttctggcag tgctctggct     60

ggcgtcgttc cacaatgggg cggcggcggt aatcataacg gcggcggcaa tagttccggc    120

ccggactcaa cgttgagcat ttatcagtac ggttccgcta acgctgcgct tgctctgcaa    180

agcgatgccc gtaaatatga tcagctggtt acccgtgttg ttacccatga aatggcacat    240

gcaggccagg gtgcggataa tagtactatt gaactgactc agaatggttt cagaaataat    300

gccaccatcg accagtggaa cgctaaaaac tccgatatta ctgtcggcca atacggcggt    360

aataacgccg cgctggttaa tcagaccgca tctgattcca gcgtaatggt gcgtcaggtt    420

ggttttggca acaacgccac ggctaaccag tattaa                              456
```

<210> SEQ ID NO 20
<211> LENGTH: 151
<212> TYPE: PRT
<213> ORGANISM: Artificial Sequence
<220> FEATURE:
<223> OTHER INFORMATION: Recombinant Salmonella enteritidis 3b afgA sequence containing the replacement fragment encoding PT3 from GP63 of Leishmania major.

<400> SEQUENCE: 20

```
Met Lys Leu Leu Lys Val Ala Ala Phe Ala Ala Ile Val Val Ser Gly
 1               5                  10                  15

Ser Ala Leu Ala Gly Val Val Pro Gln Trp Gly Gly Gly Gly Asn His
            20                  25                  30

Asn Gly Gly Gly Asn Ser Ser Gly Pro Asp Ser Thr Leu Ser Ile Tyr
        35                  40                  45
```

-continued

```
Gln Tyr Gly Ser Ala Asn Ala Ala Leu Ala Leu Gln Ser Asp Ala Arg
    50                  55                  60

Lys Tyr Asp Gln Leu Val Thr Arg Val Val Thr His Glu Met Ala His
65                  70                  75                  80

Ala Gly Gln Gly Ala Asp Asn Ser Thr Ile Glu Leu Thr Gln Asn Gly
                85                  90                  95

Phe Arg Asn Asn Ala Thr Ile Asp Gln Trp Asn Ala Lys Asn Ser Asp
            100                 105                 110

Ile Thr Val Gly Gln Tyr Gly Gly Asn Asn Ala Ala Leu Val Asn Gln
        115                 120                 125

Thr Ala Ser Asp Ser Ser Val Met Val Arg Gln Val Gly Phe Gly Asn
    130                 135                 140

Asn Ala Thr Ala Asn Gln Tyr
145                 150
```

<210> SEQ ID NO 21
<211> LENGTH: 456
<212> TYPE: DNA
<213> ORGANISM: Artificial Sequence
<220> FEATURE:
<223> OTHER INFORMATION: Recombinant Salmonella enteritidis 3b afgA sequence containing the replacement fragment encoding PT3 from GP63 of Leishmania major.

<400> SEQUENCE: 21

```
atgaaacttt taaaagtggc agcattcgca gcaatcgtag tttctggcag tgctctggct      60

ggcgtcgttc cacaatgggg cggcggcggt aatcataacg gcggcggcaa tagttccggc     120

ccggactcaa cgttgagcat ttatcagtac ggttccgcta acgctgcgct tgctctgcaa     180

agcgatgccc gtaaatctga aacgaccatt acccagagcg gttatggtaa cggcgccgat     240

gtaggccagg gtgcggataa ttatgatcag ctggttaccc gtgttgttac ccatgaaatg     300

gcacatgcag accagtggaa cgctaaaaac tccgatatta ctgtcggcca atacggcggt     360

aataacgccg cgctggttaa tcagaccgca tctgattcca gcgtaatggt gcgtcaggtt     420

ggttttggca acaacgccac ggctaaccag tattaa                               456
```

<210> SEQ ID NO 22
<211> LENGTH: 151
<212> TYPE: PRT
<213> ORGANISM: Artificial Sequence
<220> FEATURE:
<223> OTHER INFORMATION: Recombinant Salmonella enteritidis 3b afgA sequence containing the replacement fragment encoding PT3 from GP63 of Leishmania major.

<400> SEQUENCE: 22

```
Met Lys Leu Leu Lys Val Ala Ala Phe Ala Ala Ile Val Val Ser Gly
 1               5                  10                  15

Ser Ala Leu Ala Gly Val Val Pro Gln Trp Gly Gly Gly Gly Asn His
            20                  25                  30

Asn Gly Gly Gly Asn Ser Ser Gly Pro Asp Ser Thr Leu Ser Ile Tyr
        35                  40                  45

Gln Tyr Gly Ser Ala Asn Ala Ala Leu Ala Leu Gln Ser Asp Ala Arg
    50                  55                  60

Lys Ser Glu Thr Thr Ile Thr Gln Ser Gly Tyr Gly Asn Gly Ala Asp
65                  70                  75                  80

Val Gly Gln Gly Ala Asp Asn Tyr Asp Gln Leu Val Thr Arg Val Val
                85                  90                  95
```

-continued

```
Thr His Glu Met Ala His Ala Asp Gln Trp Asn Ala Lys Asn Ser Asp
            100                 105                 110

Ile Thr Val Gly Gln Tyr Gly Gly Asn Asn Ala Ala Leu Val Asn Gln
        115                 120                 125

Thr Ala Ser Asp Ser Ser Val Met Val Arg Gln Val Gly Phe Gly Asn
    130                 135                 140

Asn Ala Thr Ala Asn Gln Tyr
145                 150


<210> SEQ ID NO 23
<211> LENGTH: 456
<212> TYPE: DNA
<213> ORGANISM: Artificial Sequence
<220> FEATURE:
<223> OTHER INFORMATION: Recombinant Salmonella enteritidis 3b afgA
      sequence containing the replacement fragment
      encoding PT3 from GP63 of Leishmania major.

<400> SEQUENCE: 23

atgaaacttt taaaagtggc agcattcgca gcaatcgtag tttctggcag tgctctggct     60

ggcgtcgttc cacaatgggg cggcggcggt aatcataacg gcggcggcaa tagttccggc    120

ccggactcaa cgttgagcat ttatcagtac ggttccgcta acgctgcgct tgctctgcaa    180

agcgatgccc gtaaatctga aacgaccatt acccagagcg gttatggtaa cggcgccgat    240

gtaggccagg gtgcggataa tagtactatt gaactgactc agaatggttt cagaaataat    300

gccaccatcg accagtggaa cgctaaaaac tatgatcagc tggttacccg tgttgttacc    360

catgaaatgg cacatgcaaa tcagaccgca tctgattcca gcgtaatggt gcgtcaggtt    420

ggttttggca acaacgccac ggctaaccag tattaa                              456


<210> SEQ ID NO 24
<211> LENGTH: 151
<212> TYPE: PRT
<213> ORGANISM: Artificial Sequence
<220> FEATURE:
<223> OTHER INFORMATION: Recombinant Salmonella enteritidis 3b afgA
      sequence containing the replacement fragment
      encoding PT3 from GP63 of Leishmania major.

<400> SEQUENCE: 24

Met Lys Leu Leu Lys Val Ala Ala Phe Ala Ala Ile Val Val Ser Gly
 1               5                  10                  15

Ser Ala Leu Ala Gly Val Val Pro Gln Trp Gly Gly Gly Gly Asn His
            20                  25                  30

Asn Gly Gly Gly Asn Ser Ser Gly Pro Asp Ser Thr Leu Ser Ile Tyr
        35                  40                  45

Gln Tyr Gly Ser Ala Asn Ala Ala Leu Ala Leu Gln Ser Asp Ala Arg
    50                  55                  60

Lys Ser Glu Thr Thr Ile Thr Gln Ser Gly Tyr Gly Asn Gly Ala Asp
65                  70                  75                  80

Val Gly Gln Gly Ala Asp Asn Ser Thr Ile Glu Leu Thr Gln Asn Gly
                85                  90                  95

Phe Arg Asn Asn Ala Thr Ile Asp Gln Trp Asn Ala Lys Asn Tyr Asp
            100                 105                 110

Gln Leu Val Thr Arg Val Val Thr His Glu Met Ala His Ala Asn Gln
        115                 120                 125

Thr Ala Ser Asp Ser Ser Val Met Val Arg Gln Val Gly Phe Gly Asn
    130                 135                 140
```

-continued

```
Asn Ala Thr Ala Asn Gln Tyr
145                 150


<210> SEQ ID NO 25
<211> LENGTH: 456
<212> TYPE: DNA
<213> ORGANISM: Artificial Sequence
<220> FEATURE:
<223> OTHER INFORMATION: Recombinant Salmonella enteritidis 3b afgA
      sequence containing the replacement fragment
      encoding PT3 from GP63 of Leishmania major.

<400> SEQUENCE: 25

atgaaacttt taaaagtggc agcattcgca gcaatcgtag tttctggcag tgctctggct      60

ggcgtcgttc cacaatgggg cggcggcggt aatcataacg gcggcggcaa tagttccggc     120

ccggactcaa cgttgagcat ttatcagtac ggttccgcta acgctgcgct ttatgatcag     180

ctggttaccc gtgttgttac ccatgaaatg gcacatgcag gttatggtaa cggcgccgat     240

gtaggccagg gtgcggataa tagtactatt gaactgactc agaatggttt cagaaataat     300

gccaccatcg accagtggaa cgctaaaaac tccgatatta ctgtcggcca atacggcggt     360

aataacgccg cgctggttaa tcagaccgca tctgattcca gcgtaatggt gcgtcaggtt     420

ggttttggca acaacgccac ggctaaccag tattaa                               456


<210> SEQ ID NO 26
<211> LENGTH: 151
<212> TYPE: PRT
<213> ORGANISM: Artificial Sequence
<220> FEATURE:
<223> OTHER INFORMATION: Recombinant Salmonella enteritidis 3b afgA
      sequence containing the replacement fragment
      encoding PT3 from GP63 of Leishmania major.

<400> SEQUENCE: 26

Met Lys Leu Leu Lys Val Ala Ala Phe Ala Ala Ile Val Val Ser Gly
 1               5                  10                  15

Ser Ala Leu Ala Gly Val Val Pro Gln Trp Gly Gly Gly Gly Asn His
            20                  25                  30

Asn Gly Gly Gly Asn Ser Ser Gly Pro Asp Ser Thr Leu Ser Ile Tyr
        35                  40                  45

Gln Tyr Gly Ser Ala Asn Ala Ala Leu Tyr Asp Gln Leu Val Thr Arg
    50                  55                  60

Val Val Thr His Glu Met Ala His Ala Gly Tyr Gly Asn Gly Ala Asp
65                  70                  75                  80

Val Gly Gln Gly Ala Asp Asn Ser Thr Ile Glu Leu Thr Gln Asn Gly
                85                  90                  95

Phe Arg Asn Asn Ala Thr Ile Asp Gln Trp Asn Ala Lys Asn Ser Asp
            100                 105                 110

Ile Thr Val Gly Gln Tyr Gly Gly Asn Asn Ala Ala Leu Val Asn Gln
        115                 120                 125

Thr Ala Ser Asp Ser Ser Val Met Val Arg Gln Val Gly Phe Gly Asn
    130                 135                 140

Asn Ala Thr Ala Asn Gln Tyr
145                 150


<210> SEQ ID NO 27
<211> LENGTH: 456
<212> TYPE: DNA
<213> ORGANISM: Artificial Sequence
<220> FEATURE:
```

-continued

<223> OTHER INFORMATION: Recombinant Salmonella enteritidis 3b afgA
      sequence containing the replacement fragment
      encoding PT3 from GP63 of Leishmania major.

<400> SEQUENCE: 27

```
atgaaacttt taaaagtggc agcattcgca gcaatcgtag tttctggcag tgctctggct     60

ggcgtcgttc cacaatgggg cggcggcggt aatcataacg gcggcggcaa tagttccggc    120

ccggactcaa cgttgagcat ttatcagtac ggttccgcta acgctgcgct tgctctgcaa    180

agcgatgccc gtaaatctga aacgaccatt acccagagcg gttatggtaa cggcgccgat    240

tatgatcagc tggttacccg tgttgttacc catgaaatgg cacatgcatt cagaaataat    300

gccaccatcg accagtggaa cgctaaaaac tccgatatta ctgtcggcca atacggcggt    360

aataacgccg cgctggttaa tcagaccgca tctgattcca gcgtaatggt gcgtcaggtt    420

ggttttggca acaacgccac ggctaaccag tattaa                              456
```

<210> SEQ ID NO 28
<211> LENGTH: 151
<212> TYPE: PRT
<213> ORGANISM: Artificial Sequence
<220> FEATURE:
<223> OTHER INFORMATION: Recombinant Salmonella enteritidis 3b afgA
      sequence containing the replacement fragment
      encoding PT3 from GP63 of Leishmania major.

<400> SEQUENCE: 28

```
Met Lys Leu Leu Lys Val Ala Ala Phe Ala Ala Ile Val Val Ser Gly
 1               5                  10                  15

Ser Ala Leu Ala Gly Val Val Pro Gln Trp Gly Gly Gly Gly Asn His
            20                  25                  30

Asn Gly Gly Gly Asn Ser Ser Gly Pro Asp Ser Thr Leu Ser Ile Tyr
        35                  40                  45

Gln Tyr Gly Ser Ala Asn Ala Ala Leu Ala Leu Gln Ser Asp Ala Arg
    50                  55                  60

Lys Ser Glu Thr Thr Ile Thr Gln Ser Gly Tyr Gly Asn Gly Ala Asp
65                  70                  75                  80

Tyr Asp Gln Leu Val Thr Arg Val Val Thr His Glu Met Ala His Ala
                85                  90                  95

Phe Arg Asn Asn Ala Thr Ile Asp Gln Trp Asn Ala Lys Asn Ser Asp
            100                 105                 110

Ile Thr Val Gly Gln Tyr Gly Gly Asn Asn Ala Ala Leu Val Asn Gln
        115                 120                 125

Thr Ala Ser Asp Ser Ser Val Met Val Arg Gln Val Gly Phe Gly Asn
    130                 135                 140

Asn Ala Thr Ala Asn Gln Tyr
145                 150
```

<210> SEQ ID NO 29
<211> LENGTH: 456
<212> TYPE: DNA
<213> ORGANISM: Artificial Sequence
<220> FEATURE:
<223> OTHER INFORMATION: Recombinant Salmonella enteritidis 3b afgA
      sequence containing the replacement fragment
      encoding PT3 from GP63 of Leishmania major.

<400> SEQUENCE: 29

```
atgaaacttt taaaagtggc agcattcgca gcaatcgtag tttctggcag tgctctggct     60

ggcgtcgttc cacaatgggg cggcggcggt aatcataacg gcggcggcaa tagttccggc    120
```

-continued

```
ccggactcaa cgttgagcat ttatcagtac ggttccgcta acgctgcgct tgctctgcaa    180

agcgatgccc gtaaatctga aacgaccatt acccagagcg gttatggtaa cggcgccgat    240

gtaggccagg gtgcggataa tagtactatt gaactgactc agaatggttt cagaaataat    300

gccacctatg atcagctggt tacccgtgtt gttacccatg aaatggcaca tgcaggcggt    360

aataacgccg cgctggttaa tcagaccgca tctgattcca gcgtaatggt gcgtcaggtt    420

ggttttggca acaacgccac ggctaaccag tattaa                              456


<210> SEQ ID NO 30
<211> LENGTH: 151
<212> TYPE: PRT
<213> ORGANISM: Artificial Sequence
<220> FEATURE:
<223> OTHER INFORMATION: Recombinant Salmonella enteritidis 3b afgA
      sequence containing the replacement fragment
      encoding PT3 from GP63 of Leishmania major.

<400> SEQUENCE: 30

Met Lys Leu Leu Lys Val Ala Ala Phe Ala Ala Ile Val Val Ser Gly
 1               5                  10                  15

Ser Ala Leu Ala Gly Val Val Pro Gln Trp Gly Gly Gly Gly Asn His
            20                  25                  30

Asn Gly Gly Gly Asn Ser Ser Gly Pro Asp Ser Thr Leu Ser Ile Tyr
        35                  40                  45

Gln Tyr Gly Ser Ala Asn Ala Ala Leu Ala Leu Gln Ser Asp Ala Arg
    50                  55                  60

Lys Ser Glu Thr Thr Ile Thr Gln Ser Gly Tyr Gly Asn Gly Ala Asp
65                  70                  75                  80

Val Gly Gln Gly Ala Asp Asn Ser Thr Ile Glu Leu Thr Gln Asn Gly
                85                  90                  95

Phe Arg Asn Asn Ala Thr Tyr Asp Gln Leu Val Thr Arg Val Val Thr
            100                 105                 110

His Glu Met Ala His Ala Gly Gly Asn Asn Ala Ala Leu Val Asn Gln
        115                 120                 125

Thr Ala Ser Asp Ser Ser Val Met Val Arg Gln Val Gly Phe Gly Asn
    130                 135                 140

Asn Ala Thr Ala Asn Gln Tyr
145                 150


<210> SEQ ID NO 31
<211> LENGTH: 131
<212> TYPE: PRT
<213> ORGANISM: Salmonella enteritidis

<400> SEQUENCE: 31

Gly Val Val Pro Gln Trp Gly Gly Gly Gly Asn His Asn Gly Gly Gly
 1               5                  10                  15

Asn Ser Ser Gly Pro Asp Ser Thr Leu Ser Ile Tyr Gln Tyr Gly Ser
            20                  25                  30

Ala Asn Ala Ala Leu Ala Leu Gln Ser Asp Ala Arg Lys Ser Glu Thr
        35                  40                  45

Thr Ile Thr Gln Ser Gly Tyr Gly Asn Gly Ala Asp Val Gly Gln Gly
    50                  55                  60

Ala Asp Asn Ser Thr Ile Glu Leu Thr Gln Asn Gly Phe Arg Asn Asn
65                  70                  75                  80

Ala Thr Ile Asp Gln Trp Asn Ala Lys Asn Ser Asp Ile Thr Val Gly
```

-continued

```
                85                  90                  95

Gln Tyr Gly Gly Asn Asn Ala Ala Leu Val Asn Gln Thr Ala Ser Asp
            100                 105                 110

Ser Ser Val Met Val Arg Gln Val Gly Phe Gly Asn Asn Ala Thr Ala
        115                 120                 125

Asn Gln Tyr
    130


<210> SEQ ID NO 32
<211> LENGTH: 70
<212> TYPE: PRT
<213> ORGANISM: Salmonella enteritidis

<400> SEQUENCE: 32

Ala Arg Lys Ser Glu Thr Thr Ile Thr Gln Ser Gly Tyr Gly Asn Gly
 1               5                  10                  15

Ala Asp Val Gly Gln Gly Ala Asp Asn Ser Thr Ile Glu Leu Thr Gln
            20                  25                  30

Asn Gly Phe Arg Asn Asn Ala Thr Ile Asp Gln Trp Asn Lys Asn Asp
        35                  40                  45

Ile Val Gly Tyr Gly Asn Ala Leu Asn Thr Ser Asp Ser Val Met Val
    50                  55                  60

Arg Val Gly Ala Asn Tyr
65                  70


<210> SEQ ID NO 33
<211> LENGTH: 23
<212> TYPE: PRT
<213> ORGANISM: Artificial Sequence
<220> FEATURE:
<223> OTHER INFORMATION: Consensus sequence of the five internal repeats
      of AgfA.
<221> NAME/KEY: VARIANT
<222> LOCATION: (1)...(23)
<223> OTHER INFORMATION: Xaa = Any Amino Acid

<400> SEQUENCE: 33

Ser Xaa Xaa Xaa Xaa Xaa Gln Xaa Gly Xaa Xaa Asn Xaa Ala Xaa Xaa
 1               5                  10                  15

Xaa Gln Xaa Xaa Ala Xaa Xaa
            20


<210> SEQ ID NO 34
<211> LENGTH: 109
<212> TYPE: PRT
<213> ORGANISM: Salmonella enteritidis

<400> SEQUENCE: 34

Ser Thr Leu Ser Ile Tyr Gln Tyr Gly Ser Ala Asn Ala Ala Leu Ala
 1               5                  10                  15

Leu Gln Ser Asp Ala Arg Lys Ser Glu Thr Thr Ile Thr Gln Ser Gly
            20                  25                  30

Tyr Gly Asn Gly Ala Asp Val Gly Gln Gly Ala Asp Asn Ser Thr Ile
        35                  40                  45

Glu Leu Thr Gln Asn Gly Phe Arg Asn Asn Ala Thr Ile Asp Gln Trp
    50                  55                  60

Asn Ala Lys Asn Ser Asp Ile Thr Val Gly Gln Tyr Gly Gly Asn Asn
65                  70                  75                  80

Ala Ala Leu Val Asn Gln Thr Ala Ser Asp Ser Ser Val Met Val Arg
                85                  90                  95
```

-continued

```
Gln Val Gly Phe Gly Asn Asn Ala Thr Ala Asn Gln Tyr
            100                 105


<210> SEQ ID NO 35
<211> LENGTH: 109
<212> TYPE: PRT
<213> ORGANISM: Escherichia coli

<400> SEQUENCE: 35

Ser Glu Leu Asn Ile Tyr Gln Tyr Gly Gly Gly Asn Ser Ala Leu Ala
 1               5                  10                  15

Leu Gln Thr Asp Ala Arg Asn Ser Asp Leu Thr Ile Thr Gln His Gly
            20                  25                  30

Gly Gly Asn Gly Ala Asp Val Gly Gln Gly Ser Asp Asp Ser Ser Ile
        35                  40                  45

Asp Leu Thr Gln Arg Gly Phe Gly Asn Ser Ala Thr Leu Asp Gln Trp
    50                  55                  60

Asn Gly Lys Asn Ser Glu Met Thr Val Lys Gln Phe Gly Gly Gly Asn
65                  70                  75                  80

Gly Ala Ala Val Asp Gln Thr Ala Ser Asn Ser Ser Val Asn Val Thr
                85                  90                  95

Gln Val Gly Phe Gly Asn Asn Ala Thr Ala His Gln Tyr
            100                 105


<210> SEQ ID NO 36
<211> LENGTH: 56
<212> TYPE: PRT
<213> ORGANISM: Serratia marcescens

<400> SEQUENCE: 36

Ile Glu Asn Ala Ile Gly Gly Ser Gly Asn Asp Val Ile Val Gly Asn
 1               5                  10                  15

Ala Ala Asn Asn Val Leu Lys Gly Gly Ala Gly Asn Asp Val Leu Phe
             20                  25                  30

Gly Gly Gly Gly Ala Asp Glu Leu Trp Gly Gly Ala Gly Lys Asp Ile
         35                  40                  45

Phe Val Phe Ser Ala Ala Ser Asp
     50                  55


<210> SEQ ID NO 37
<211> LENGTH: 68
<212> TYPE: PRT
<213> ORGANISM: Salmonella enteritidis

<400> SEQUENCE: 37

Ser Thr Leu Ser Ile Tyr Gln Tyr Gly Ser Ala Asn Ala Ala Leu Ala
 1               5                  10                  15

Leu Gln Ser Asp Ala Arg Lys Ser Glu Thr Thr Ile Thr Gln Ser Gly
            20                  25                  30

Tyr Gly Asn Gly Ala Asp Val Gly Gln Gly Ala Asp Asn Ser Thr Ile
        35                  40                  45

Glu Leu Thr Gln Asn Gly Phe Arg Asn Asn Ala Thr Ile Asp Gln Trp
    50                  55                  60

Asn Ala Lys Asn
65


<210> SEQ ID NO 38
<211> LENGTH: 47
```

-continued

<212> TYPE: PRT
<213> ORGANISM: bovine

<400> SEQUENCE: 38

```
Val Ile Ile Ser Lys Lys Gly Asp Ile Ile Thr Ile Arg Thr Glu Ser
 1               5                  10                  15

Pro Phe Lys Asn Thr Glu Ile Ser Phe Lys Leu Gly Gln Glu Phe Glu
            20                  25                  30

Glu Thr Thr Ala Asp Asn Arg Lys Thr Lys Ser Thr Val Thr Leu
        35                  40                  45
```

<210> SEQ ID NO 39
<211> LENGTH: 48
<212> TYPE: PRT
<213> ORGANISM: Salmonella enteritidis

<400> SEQUENCE: 39

```
Leu Ser Ile Tyr Gln Tyr Gly Ser Ala Asn Ala Ala Leu Ala Leu Gln
 1               5                  10                  15

Ser Asp Ala Arg Lys Ser Glu Thr Thr Ile Thr Gln Ser Gly Tyr Gly
            20                  25                  30

Asn Gly Ala Asp Val Gly Gln Gly Ala Asp Asn Ser Thr Ile Glu Leu
        35                  40                  45
```

<210> SEQ ID NO 40
<211> LENGTH: 19
<212> TYPE: PRT
<213> ORGANISM: Unknown
<220> FEATURE:
<223> OTHER INFORMATION: Beta-prism motif of the vitelline membrane
      outer layer protein I (VMO-I)

<400> SEQUENCE: 40

```
Phe Ala Leu Lys Val Glu Pro Ser Gln Phe Gly Arg Asp Asp Thr Ala
 1               5                  10                  15

Leu Asn Gly
```

<210> SEQ ID NO 41
<211> LENGTH: 19
<212> TYPE: PRT
<213> ORGANISM: Unknown
<220> FEATURE:
<223> OTHER INFORMATION: Beta-prism motif of the vitelline membrane
      outer layer protein I (VMO-I)

<400> SEQUENCE: 41

```
Phe Ser Leu Arg Ser Glu Lys Ser Gln Gly Gly Gly Asp Asp Thr Ala
 1               5                  10                  15

Ala Asn Asn
```

<210> SEQ ID NO 42
<211> LENGTH: 19
<212> TYPE: PRT
<213> ORGANISM: Unknown
<220> FEATURE:
<223> OTHER INFORMATION: Beta-prism motif of the vitelline membrane
      outer layer protein I (VMO-I)

<400> SEQUENCE: 42

```
Leu Gln Thr Lys Val Glu Ser Pro Gln Gly Leu Arg Asp Asp Thr Ala
 1               5                  10                  15

Leu Asn Asn
```

-continued

<210> SEQ ID NO 43
<211> LENGTH: 16
<212> TYPE: PRT
<213> ORGANISM: Unknown
<220> FEATURE:
<223> OTHER INFORMATION: Beta-prism motif of the vitelline membrane outer layer protein I (VMO-I)

<400> SEQUENCE: 43

```
Leu Ser Ile Tyr Gln Tyr Gly Ser Ala Asn Ala Ala Leu Ala Leu Gln
 1               5                  10                  15
```

<210> SEQ ID NO 44
<211> LENGTH: 16
<212> TYPE: PRT
<213> ORGANISM: Unknown
<220> FEATURE:
<223> OTHER INFORMATION: Beta-prism motif of the vitelline membrane outer layer protein I (VMO-I)

<400> SEQUENCE: 44

```
Ile Glu Leu Thr Gln Asn Gly Phe Arg Asn Asn Ala Thr Ile Asp Gln
 1               5                  10                  15
```

<210> SEQ ID NO 45
<211> LENGTH: 16
<212> TYPE: PRT
<213> ORGANISM: Unknown
<220> FEATURE:
<223> OTHER INFORMATION: Beta-prism motif of the vitelline membrane outer layer protein I (VMO-I)

<400> SEQUENCE: 45

```
Val Met Val Arg Gln Val Gly Phe Gly Asn Asn Ala Thr Ala Asn Gln
 1               5                  10                  15
```

<210> SEQ ID NO 46
<211> LENGTH: 143
<212> TYPE: PRT
<213> ORGANISM: Salmonella enteritidis

<400> SEQUENCE: 46

```
Ala Gly Phe Val Gly Asn Lys Ala Val Val Gln Ala Ala Val Thr Ile
 1               5                  10                  15

Ala Ala Gln Asn Thr Thr Ser Ala Asn Trp Ser Gln Asp Pro Gly Phe
             20                  25                  30

Thr Gly Pro Ala Val Ala Ala Gly Gln Lys Val Gly Thr Leu Ser Ile
         35                  40                  45

Thr Ala Thr Gly Pro His Asn Ser Val Ser Ile Ala Gly Lys Gly Ala
    50                  55                  60

Ser Val Ser Gly Gly Val Ala Thr Val Pro Phe Val Asp Gly Gln Gly
65                  70                  75                  80

Gln Pro Val Phe Arg Gly Arg Ile Gln Gly Ala Asn Ile Asn Asp Gln
                85                  90                  95

Ala Asn Thr Gly Ile Asp Gly Leu Ala Gly Trp Arg Val Ala Ser Ser
            100                 105                 110

Gln Glu Thr Leu Asn Val Pro Val Thr Thr Phe Gly Lys Ser Thr Leu
        115                 120                 125

Pro Ala Gly Phe Thr Ala Thr Phe Tyr Val Gln Gln Tyr Gln Asn
    130                 135                 140
```

<210> SEQ ID NO 47

-continued

<211> LENGTH: 39
<212> TYPE: DNA
<213> ORGANISM: Artificial Sequence
<220> FEATURE:
<223> OTHER INFORMATION: PCR primer

<400> SEQUENCE: 47
ttggaattct tcttaaattt ttaaaatggc gttgagtat 39

<210> SEQ ID NO 48
<211> LENGTH: 78
<212> TYPE: DNA
<213> ORGANISM: Artificial Sequence
<220> FEATURE:
<223> OTHER INFORMATION: PCR primer

<400> SEQUENCE: 48
agcatgagcc atttcatgtg taacaacacg tgtaacgagc tgatcatatg caatagtaac 60
cgctgcctga accactgc 78

<210> SEQ ID NO 49
<211> LENGTH: 78
<212> TYPE: DNA
<213> ORGANISM: Artificial Sequence
<220> FEATURE:
<223> OTHER INFORMATION: PCR primer

<400> SEQUENCE: 49
tatgatcagc tcgttacacg tgttgttaca catgaaatgg ctcatgctgg gcctgctgtt 60
gctgctggtc agaaagtt 78

<210> SEQ ID NO 50
<211> LENGTH: 39
<212> TYPE: DNA
<213> ORGANISM: Artificial Sequence
<220> FEATURE:
<223> OTHER INFORMATION: PCR primer

<400> SEQUENCE: 50
attaagctta tacataatcc ctctttaagt ttttgcatg 39

<210> SEQ ID NO 51
<211> LENGTH: 39
<212> TYPE: DNA
<213> ORGANISM: Artificial Sequence
<220> FEATURE:
<223> OTHER INFORMATION: PCR primer

<400> SEQUENCE: 51
gcagaattca gcagttgtag tgcagaaaca gtcgcatat 39

<210> SEQ ID NO 52
<211> LENGTH: 78
<212> TYPE: DNA
<213> ORGANISM: Artificial Sequence
<220> FEATURE:
<223> OTHER INFORMATION: PCR primer

<400> SEQUENCE: 52
tgcatgtgcc atttcatggg taacaacacg ggtaaccagc tgatcatagt ttttagcgtt 60
ccactggtcg atggtggc 78

<210> SEQ ID NO 53
<211> LENGTH: 78

-continued

<212> TYPE: DNA
<213> ORGANISM: Artificial Sequence
<220> FEATURE:
<223> OTHER INFORMATION: PCR primer

<400> SEQUENCE: 53
tatgatcagc tggttacccg tgttgttacc catgaaatgg cacatgcaaa tcagaccgca 60
tctgattcca gcgtaatg 78

<210> SEQ ID NO 54
<211> LENGTH: 39
<212> TYPE: DNA
<213> ORGANISM: Artificial Sequence
<220> FEATURE:
<223> OTHER INFORMATION: PCR primer

<400> SEQUENCE: 54
agacgcaagc ttcgtttaat gtgacctgag ggatcaccg 39

<210> SEQ ID NO 55
<211> LENGTH: 30
<212> TYPE: DNA
<213> ORGANISM: Artificial Sequence
<220> FEATURE:
<223> OTHER INFORMATION: PCR primer

<400> SEQUENCE: 55
gggatgttgt gtaaagataa aaaaatagtg 30

<210> SEQ ID NO 56
<211> LENGTH: 30
<212> TYPE: DNA
<213> ORGANISM: Artificial Sequence
<220> FEATURE:
<223> OTHER INFORMATION: PCR primer

<400> SEQUENCE: 56
tgcccaatct taggccataa tatttttgtg 30

<210> SEQ ID NO 57
<211> LENGTH: 33
<212> TYPE: DNA
<213> ORGANISM: Artificial Sequence
<220> FEATURE:
<223> OTHER INFORMATION: PCR primer

<400> SEQUENCE: 57
aggaaggatc aaaactattg tccgttattt cac 33

<210> SEQ ID NO 58
<211> LENGTH: 33
<212> TYPE: DNA
<213> ORGANISM: Artificial Sequence
<220> FEATURE:
<223> OTHER INFORMATION: PCR primer

<400> SEQUENCE: 58
tatatttaca ctaagacgag acaactcaat cgg 33

<210> SEQ ID NO 59
<211> LENGTH: 18
<212> TYPE: PRT
<213> ORGANISM: Artificial Sequence
<220> FEATURE:
<223> OTHER INFORMATION: Consensus sequence
<221> NAME/KEY: VARIANT
<222> LOCATION: (1)...(18)

-continued

```
<223> OTHER INFORMATION: Xaa = Any Amino Acid

<400> SEQUENCE: 59

Ser Xaa Xaa Xaa Xaa Xaa Gln Xaa Gly Xaa Xaa Asn Xaa Ala Xaa Xaa
 1               5                  10                  15

Xaa Gln
```